US009132110B2

(12) United States Patent
Singh et al.

(10) Patent No.: US 9,132,110 B2
(45) Date of Patent: *Sep. 15, 2015

(54) TREATMENT OF PAIN WITH TOPICAL DICLOFENAC

(71) Applicant: NUVO RESEARCH INC., Mississauga (CA)

(72) Inventors: Jagat Singh, Scarborough (CA); Joseph Zev Shainhouse, North York (CA); Bradley S. Galer, West Chester, PA (US); Robert Dominic King-Smith, San Diego, CA (US); Lisa Marie Grierson, Richmond Hill (CA); Maria Burian, Stolberg (DE); Jonathan Wilkin, Columbus, OH (US); Edward Kisak, San Diego, CA (US); John M. Newsam, La Jolla, CA (US)

(73) Assignee: HZNP LIMITED, Pembroke (BM)

( * ) Notice: Subject to any disclaimer, the term of this patent is extended or adjusted under 35 U.S.C. 154(b) by 284 days.

This patent is subject to a terminal disclaimer.

(21) Appl. No.: 13/665,790

(22) Filed: Oct. 31, 2012

(65) Prior Publication Data

US 2013/0065870 A1  Mar. 14, 2013

Related U.S. Application Data

(63) Continuation of application No. 12/660,865, filed on Mar. 4, 2010, which is a continuation-in-part of application No. 12/459,998, filed on Jul. 10, 2009.

(60) Provisional application No. 61/211,600, filed on Mar. 31, 2009.

(51) Int. Cl.
*A61K 31/10* (2006.01)
*A61K 31/196* (2006.01)
*A61K 45/06* (2006.01)

(52) U.S. Cl.
CPC .............. *A61K 31/196* (2013.01); *A61K 31/10* (2013.01); *A61K 45/06* (2013.01)

(58) Field of Classification Search
CPC ... A61K 31/10; A61K 31/136; A61K 31/196; A61K 2300/00; A61K 45/06; C07C 15/04; C07C 317/04
See application file for complete search history.

(56) References Cited

U.S. PATENT DOCUMENTS

| | | | |
|---|---|---|---|
| 3,711,602 A | 1/1973 | Herschler | |
| 3,740,421 A | 6/1973 | Schmolka | |
| 4,309,414 A | 1/1982 | Inagi et al. | |
| 4,342,784 A | 8/1982 | Havemeyer et al. | |
| 4,441,739 A | 4/1984 | Cluff et al. | |
| 4,543,251 A | 9/1985 | Kamishita | |
| 4,575,515 A | 3/1986 | Sandborn | |
| 4,652,557 A | 3/1987 | Sandborn | |
| 4,670,254 A | 6/1987 | Kamishita | |
| 4,707,354 A | 11/1987 | Garlen et al. | |
| 4,855,294 A | 8/1989 | Patel et al. | |
| 4,871,767 A | 10/1989 | Beckermann et al. | |
| 5,350,769 A | 9/1994 | Kasai et al. | |
| 5,374,661 A | 12/1994 | Betlach, II | |
| 5,422,102 A | 6/1995 | Ikeda et al. | |
| 5,674,912 A | 10/1997 | Martin | |
| 5,874,479 A | 2/1999 | Martin | |
| 6,387,383 B1 | 5/2002 | Dow et al. | |
| 6,399,093 B1 | 6/2002 | Petrus | |
| 6,750,291 B2 | 6/2004 | Kim et al. | |
| 8,217,078 B1 | 7/2012 | Singh et al. | |
| 2002/0012695 A1 | 1/2002 | Lee et al. | |
| 2002/0197292 A1 | 12/2002 | Fowler | |
| 2003/0082226 A1 | 5/2003 | Samour et al. | |
| 2003/0161867 A1 | 8/2003 | Lu et al. | |
| 2004/0175415 A1 | 9/2004 | Chan et al. | |
| 2004/0213744 A1 | 10/2004 | Lulla et al. | |
| 2004/0222123 A1 | 11/2004 | Niemann | |
| 2005/0239894 A1 | 10/2005 | Steiger | |
| 2006/0148903 A1 | 7/2006 | Burch et al. | |
| 2007/0141182 A1 | 6/2007 | Niazi | |
| 2008/0300311 A1 | 12/2008 | Kisak et al. | |
| 2009/0131447 A1 | 5/2009 | Kamboj et al. | |
| 2013/0041034 A1 | 2/2013 | Singh et al. | |

FOREIGN PATENT DOCUMENTS

| | | |
|---|---|---|
| EP | 0 245 126 | 11/1987 |
| EP | 0 450 123 | 10/1991 |
| JP | 61-254519 | 11/1986 |
| JP | 61-277613 | 12/1986 |
| JP | 62-263122 | 11/1987 |
| JP | 63-83023 | 4/1988 |
| JP | 3-291222 | 12/1991 |
| JP | 2001-513543 | 9/2001 |
| WO | 97/13528 | 4/1997 |

(Continued)

OTHER PUBLICATIONS

Popovich, Remington: The Science and Practice of Pharmacy, Lippincott Williams & Wilkins, 21$^{st}$ ed., part 8B, p. 2033.*
Anchordoguy, T.J., "Temperature-dependent perturbation of phospholipid bilayers by dimethylsulfoxide," Biochimica et Biophysica Acta, 1104:117-122, 1992.
Anigbogu, A.N.C. et al., "Fourier transform Raman spectroscopy of interactions between the penetration enhancer dimethyl sulfoxide and human stratum corneum," International Journal of Pharmaceutics, 125:265-282, 1995.
Barry, B.W., "Mode of action of penetration enhancers in human skin," Journal of Controlled Release, 6:85-97, 1987.
Baynes, R.E. and Riviere, J.E., "Influence of inert ingredients in pesticide formulations on dermal absorption of carbaryl," Am. J. Vet. Res., 59:168-175, 1998.

(Continued)

*Primary Examiner* — Sarah Pihonak

(57) ABSTRACT

The field involves compositions useful for pain relief, including diclofenac solution and gel formulations, in particular methods of use thereof, articles of manufacture and kits that provide novel preclinical, clinical and other information to users.

28 Claims, 10 Drawing Sheets

(56) References Cited

FOREIGN PATENT DOCUMENTS

| WO | 99/09954 | 3/1999 |
|---|---|---|
| WO | 03/094905 A1 | 11/2003 |
| WO | WO2004/017998 | 3/2004 |
| WO | 2005/009510 | 2/2005 |
| WO | 2006/096360 | 9/2006 |
| WO | 2007/010559 A2 | 1/2007 |
| WO | 2007/016766 A1 | 2/2007 |
| WO | 2007/089617 A2 | 8/2007 |
| WO | 2008/049020 A2 | 4/2008 |
| WO | 2008/088827 A2 | 7/2008 |
| WO | WO 2010/060798 A1 | 6/2010 |

OTHER PUBLICATIONS

Baynes, R.E. et al., "The influence of diethyl-*m*-toluamide (DEET) on the percutaneous absorption of permethrin and carbaryl," Toxicology and Applied Pharmacology, 144:332-339, 1997.

Büyüktimkin, N. et al., "Chemical means of transdermal drug permeation enhancement," Chapter 11 of Transdermal and Topical Drug Delivery Systems, Tapash K. Ghosh et al., eds., pp. 357 and 404-407, 1997.

Carter-Horner Corp., "Kemsol® , Dimethylsulfoxide, Scleroderma Therapy," in 2000 Compendium of Pharmaceuticals and Specialties (CPS), Louise Wellbanks et al., eds., Canadian Pharmacists Association, Ontario, Canada, p. 804, 2000.

Dimethaid Research Inc., Product Monograph: $^{Pr}$Pennsaid® (1.5% w/w disclofenac sodium solution), 41 pages, Dimethaid Health Care Ltd., Ontario, Canada, 2003.

Drug and Therapeutic Information, Inc., "A further warning on DMSO," The Medical Letter on Drugs and Therapeutics, vol. 7, No. 20, Issue 175, p. 80, 1965.

Drug and Therapeutic Information, Inc., "Dimethyl Sulfoxide (DMSO)," The Medical Letter on Drugs and Therapeutics, vol. 7, No. 11, Issue 166, pp. 42-44, 1965.

FDA's guidelines for inactive ingredients for Jan. 2010, 1 page, 2010.

FDA's guidelines for inactive ingredients for Jun. 2010, 1 page, 2010.

Fluhr, J.W. et al. "Transepidermal water loss reflects permeability barrier status: validation in human and rodent in vivo and ex vivo models," Experimental Dermatology, 15:483-492, 2006.

G.D. Searle & Co., Celebrex® (Celecoxib) Capsules | Safety Information, Revised label based on FDA letter Feb. 23, 2000, 21 pages, G.D. Searle & Co, IL, USA and Pfizer Inc., NY, USA, Apr. 24, 2000.

G.D. Searle & Co., Celebrex® (Celecoxib) Capsules, NDA 20-998/S-018, NDA 20-998/S-019, Revised: Jul. 2005, 25 pages (pp. 3-27), G.D. Searle LLC, Division of Pfizer Inc., NY, USA, 2005.

Greve, T.M. et al., "Penetration mechanism of dimethyl sulfoxide in human and pig ear skin: An ATR-FTIR and near-FT Raman spectroscopic in vivo and in vitro study," Spectroscopy, 22:405-417, 2008.

Hadgraft, J., "Mini review: Passive enhancement strategies in topical and transdermal drug delivery," International Journal of Pharmaceutics, 184:1-6, 1999.

Henderson, T.R. and Henderson, R.F., "Effects of dimethyl sulfoxide on subunit proteins," Ann. N Y Acad. Sci., 243:38-53, 1975.

Hsu, L.R. et al., "The effect of pretreatment by penetration enhancers on the in vivo percutaneous absorption of piroxicam from its gel form in rabbits," International Journal of Pharmaceutics, 71:193-200, 1991.

Kanikkannan, N. et al., "Structure-activity relationship of chemical penetration enhancers in transdermal drug delivery," Current Medicinal Chemistry, 6(7):593-608, 1999.

Kemppainen, B.W. et al., "Comparison of penetration and metabolism of [$^3$H]Diacetoxyscirpenol, [$^3$H]Verrucarin A and [$^3$H]T-2 toxin in skin," Fd Chem. Toxic., 25(5):379-386, 1987.

Kemppainen, B.W. et al., "Evaluation of monkey skin as a model for in vitro percutaneous penetration and metabolism of [$^3$H]T-2 Toxin in Human Skin," Fundamental and Applied Toxicology, 7:367-375, 1986.

Kemppainen, B.W. et al., "In vitro percutaneous penetration and metabolism of [$^3$h]t-2 toxin: comparison of human, rabbit, guinea pig and rat," Toxicon, 25(2):185-194, 1987.

Kligman, A.M., "Topical pharmacology and toxicology of dimethyl sulfoxide—Part 1," JAMA, 193(10):140-148, 1965.

Lin, S.Y., "Direct or indirect skin lipid-ordering effect of pyrrolidone carboxylate sodium after topical treatment with penetration enhancers," Bio-Medical Materials and Engineering, 5(1):9-20, 1995.

Malten, K.E. and Arend, J.D., "Topical toxicity of various concentrations of DMSO recorded with impedance measurements and water vapour loss measurements," Contact Dermatitis, 4:80-92, 1978.

Notman, R. et al., "The permeability enhancing mechanism of DMSO in ceramide bilayers simulated by molecular dynamics," Biophysical Journal, 93:2056-2068, 2007.

Oertel, R.P., "Protein conformational changes induced in human stratum corneum by organic sulfoxides: An infrared spectroscopic investigation," Biopolymers, 16:2329-2345, 1977.

Pharmacia, Product Label: Rogaine® Extra Strength Topical Solution, Pharmacia Consumer Healthcare, Peapack, NJ, USA, 2002.

Physicians Total Care, Inc., Retin-A—tretinoin cream/tretinoin gel product insert, 6 pages, Ortho Dermatological, Division of Ortho-McNeil Pharmaceutical, Inc., Skillman, New Jersey, USA, 2001.

Rodgers, K. and Xiong, S., "Effect of acute administration of malathion by oral and dermal routes on serum histamine levels," Int. J. Immunopharmac., 19(8):437-441, 1997.

Walker, R.B. and Smith E.W., "The role of percutaneous penetration enhancers," Advanced Drug Delivery Reviews, 18:295-301, 1996.

Waller, J.M. et al., "'Keratolytic' properties of benzoyl peroxide and retinoic acid resemble salicylic acid in man," Skin Pharmacol Physiol, 19:283-289, 2006.

Williams, A.C. and Barry, B.W., "Penetration enhancers," Advanced Drug Delivery Reviews, 56:603-618, 2004.

S. Baboota, et al.; *Formulation and Evaluation of Once-a-Day Transdermal Gels of Diclofenac Diethylamine*; Methods and Findings in Experimental and Clinical Pharmacology; 2006; 109-114; Thomson Reuters, New York.

Bookman et al.; An article entitled "Effect of a topical diclofenac solution for relieving symptoms of primary osteoarthritis of the knee: a randomized controlled trial." Canadian Medical Journal 2004; 171(4), 333-338. Retrieved from the Internet: http://canadianmedicaljournal.ca/cgi/reprint/171/4/333.

Towheed; An article entitled "Pennsaid® Therapy for Osteoarthritis of the Knee: A Systematic Review and Metaanalysis of Randomized Controlled Trials." The Journal of Rheumatology 2006, 33(3), 567-573.

Towheed; An article entitled "Published meta-analyses of pharmacological therapies for osteoarthritis". Osteoarthritis and Cartilage 2002, 10, 836-837.

Tugwell et al.; An article entitled "Equivalence Study of a Topical Diclofenac Solution (Pennsaid®) Compared with Oral Diclofenac in Symptomatic Treatment of Osteoarthritis of the Knee: A Randomized Controlled Trial." The Journal of Rheumatology 2004; 31(10), 2002-2012.

Roth et al.; An article entitled "Efficacy and Safety of a Topical Diclofenac Solution (Pennsaid) in the Treatment of Primary Osteoarthritis of the Knee." Arch Intern Med. 2004, 164, 2017-2023.

Hui et al.; An article entitled "In Vivo Bioavailability and Metabolism of Topical Diclofenac Lotion in Human Volunteers." Pharmaceutical Research 1998, 15(10), 1589-1595.

Hewitt et al.; An article entitled "In Vitro Cutaneous Disposition of a Topical Diclofenac Lotion in Human Skin: Effect of a Multi-Dose Regimen." Pharmaceutical Research 1998, 15(7), 988-992.

Shainhouse; An article entitled "OARSI guidelines for hip and knee OA: deciphering the topical drug mélange." Osteoarthritis Cartilage, 2008, 16(12), 1586-7.

An article entitled "Other articles noted" by Evidence-Based Medicine, 2005, 10, 63-64.

Shainhouse et al.; An article entitled "A Long-Term, Open-Label Study to Confirm the Safety of Topical Diclofenac Solution Containing Dimethyl Sulfoxide in the Treatment of the Osteoarthritic Knee." American Journal of Therapeutics 0, 000-000 (2010).

Simon et al.; An article entitled "Efficacy and safety of topical diclofenac containing dimethyl sulfoxide (DMSO) compared with those of topical placebo, DMSO, vehicle and oral diclofenac for knee osteoarthritis." Pain, 2009, 143(3), 238-45.

(56) References Cited

OTHER PUBLICATIONS

Lin et al.; An article entitled "Efficacy of topical non-steroidal anti-inflammatory drugs in the treatment of osteoarthritis: meta-analysis of randomized controlled trials." BMJ 2004, 329(7461), ff.
Ozguney; An article entitled "An alternative topical treatment of osteoarthritis of the knee with cutaneous diclofenac solution." Expert Opinion on Pharmacotherapy 2008, 9(10), 1805-1816.
Baer et al.; An article entitled "Treatment of osteoarthritis of the knee with a topical diclofenac solution: a randomized controlled, 6-wee trial [ISRCTN53366886]" BMC Musculoskeletal Disorders, 2005, 6:44, Aug. 8, 2005. Retrieved from the internet: http://www.ncbi.nlm.nih.gov/pmc/articles/PMC1201146/pdf/1471-2474-6-44.pdf.
Galer et al.; An article entitled "Use of Topiceuticals (Topically Applied, Peripherally Acting Drugs) in the Treatment of Chronic Pain." Current Drug Therapy 2006, 1(3), 273-282.
Moen; An article entitled "Topical Diclofenac Solution." Drugs, 2009, 69(18), 2621-32. Retrieved from the Internet: http://www.ncbi.nlm.nih.gov/pubmed/19943711.
Nelson et al.; an article entitled "Phase IV, open-label assessment of the treatment of actinic keratosis with 3.0% diclofenac sodium topical gel (Solaraze™)." Journal of Drugs in Dermatology 2004,3(4), 401ff.
Novartis Consumer Health, Inc.; Prescribing Information of Voltaren® Gel; pp. 1-23; revised Jul. 2009.
Bellamy, N. et al., "Recommendations for a core set of outcome measures for future phase III clinical trials in knee, hip, and hand osteoarthritis," J Rheumatol, 24:799-802, 1997.
Browning, R. et al., "Reducing the dose of oral NSAIDs by use of feldene gel: an open study in elderly patients with osteoarthritis," Advances in Therapy, 11(4):198-207, 1994.
Dua, K. et al., "Formulation and evaluation of topical bases of aceclofenac," The Indian Pharmacist, Prabha Schroff, 5(45):73-75, 2006.
Franz, T. "Percutaneous absorption: on the relevance of in vitro data," J. Invest Derm, 64(3):190-195, 1975.
Heyneman, C.A. et al., "Oral versus topical NSAIDs in rheumatic diseases," Drugs, Adis International Limited, vol. 60, Issue 3, pp. 555-574, 2000.
Ho, H. et al., "The influence of cosolvents on the in-vitro percutaneous penetration of diclofenac sodium from a gel system," J Pharm Pharmacol, 46:636-642, 1994.
ICIS News 1999-2011 (http://www.chemindustry.com/chemicals/0197997.html), Jul. 28, 2011.
Kantarci, G. et al., "In vitro permeation of diclofenac sodium from novel microemulsion formulations through rabbit skin," Drug Development Research, 65:17-25, 2005.
Karande, P. et al., "Insights into synergistic interactions in binary mixtures of chemical permeation enhancers for transdermal drug delivery," J. Controlled Release, 115:85-93, 2006.
Karande, P. et al,. "High throughput screening of transdermal formulations," Pharm. Res., 19(5):655-660, 2002.
Laba, D., "Ch. 4. Rheological additives. Rheological properties of cosmetics and toiletries," Cosmetic Science and Technology Series, 13:55-152, 1993.
Mehta, R., "Topical and transdermal drug delivery: What a pharmacist needs to know," Inet Continuing education, InetCE.com, pp. 1-10, 2004.
Miao et al. "Preparation and Clinical Application of Diclofenac Sodium Gel," Railway Medical Journal, 28(1):14-15, 2000.
Minghetti, P. et al., "Ex vivo study of transdermal permeation of four diclofenac salts from different vehicles," J. of Pharm. Sci., 96(4):1-10, 2007.
Morison, W., "Photosensitivity," The New England Journal of Medicine, Mass. Med. Soc., 350:1111-17, 2004.
Naito, S. et al., Percutaneous absorption of diclofenac sodium ointment, Int. J. of Pharmaceutics, 24:115-124, 1985.
Nishihata, T. et al., "Percutaneous absorption of diclofenac in rats and humans: aqueous gel formulation," International Journal of Pharmaceutics, 46:1-7, 1988.

Obata, Y et al., "Effect of ethanol on skin permeation of nonionized and ionized diclofenac," Int. J. of Pharmaceutics, 89:191-198, 1993.
Ostrenga, J. et al., "Significance of vehicle composition I: Relationship between topical vehicle composition, skin penetrability, and clinical efficacy," J. Pharm Sciences, 60(8):1175-79, 1971.
Ozguney, I. et al., "Transdermal delivery of diclofenac sodium through rat skin from various formulations," AAPS PharmSciTech, 7(4) Article 88 E1-E7, 2006.
Prausnitz, M., "Current status and future potential of transdermal drug delivery," Nature Reviews, 3:115-124, 2004.
"Product Monograph, PR Pennsaide®"; Dimethaid Health Care Ltd, Oct. 20, 2003. Retrieved from the Internet: http://www.osteo-arthritis.org/downloads/Pennsaid_HCP_Mono.pdf.
Rosenstein, E., "Topical agents in the treatment of rheumatic disorders," Rheum. Dis. Clin North Am., 25(4): 899-918, 1999.
Cevc, Gregor et al., "New, highly efficient formulation of diclofenac for the topical, transdermal administration in ultradeformable drug carriers, Transfersomes," Biochimica et Biophysica Acta, 2001, Elsevier, vol. 1514, pp. 191-205.
Alberti, I., et al. "Pharmaceutical development and clinical effectiveness of a novel gel technology for transdermal drug delivery," Expert Opin. Drug Deliv. 2005, 2(5), 935-950.
ANDA Notice Letter, Watson Laboratories, Inc. to Mallinckrodt Inc. and HZNP Limited. Re: Notification of Certification for U.S. Pat. Nos. 8,217,078, 8,252,838, 8,546,450, 8,563,613, 8,618,164 and 8,741,956 Pursuant to § 505G)(2)(B)(iv) of the Federal Food, Drug, and Cosmetic Act. Nov. 12, 2014.
ANDA Notice Letter, Paddock Laboratories, LLC to Mallinckrodt Inc. and HZNP Limited. Re: Notification of Certification of Invalidity, Unenforceability, and/or NonInfringement for U.S. Pat. No. 8,217,078, 8,252,838, 8,546,450, 8,563,613, 8,618,164, and 8,741,956 Pursuant to § 505(j)(2)(B)(iv) of the Federal Food, Drug, and Cosmetic Act. Dec. 1, 2014.
ANDA Notice Letter, Taro Pharmaceuticals, USA, Inc. and Taro Pharmaceutical Industries, Ltd. to Mallinckrodt Inc. and HZNP Limited. Re: Notification Pursuant to the Federal Food, Drug, and Cosmetic Act (21 U.S.C. 355(j)(2)(B)(ii) and 21 C.F.R. § 314.95): ANDA No. 208098, U.S. Pat. No. 8,217,078, 8,252,838, 8,546,450, 8,563,613, 8,618,164, 8,741,956, and 8,871,809; PENNSAID (Diclofenac Sodium 2.0%). Jan. 30, 2015.
Bayer Aspirin Label, downloaded from Drugs.com on Jan. 19, 2015.
Bommannan, D., et al., "Examination of the effect of ethanol on human stratum corneum in vivo using infrared spectroscopy," J. of Controlled Release, 1991, 16, 299-304.
Carbopol Ultrez 10 Technical Data Sheet, Jan. 2002.
Complaint, *Horizon Pharma Ireland Limited, et al.* v- *Watson Laboratories, Inc., et al.* U.S. District Court for the District of New Jersey. Civ. Action No. 2:14-cv-07992 (Dec. 23, 2014); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Complaint, *Horizon Pharma Ireland Limited, et al.* v- *Paddock Laboratories, LLC, et al.* U.S. District Court for the District of New Jersey. Civ. Action No. 1:15-cv-00368 (Jan. 13, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Complaint, *Horizon Pharma Ireland Limited, et al.* v- *Paddock Laboratories, LLC et al.* U.S. District Court for the District of Delaware. Civ. Action No. 1:15-cv-00043 (Jan. 14, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Dachir, S., et al., "Amelioration of Sulfur Mustard Skin Injury Following a Topical Treatment with a Mixture of a Steroid and a NSAID," J. of App. Toxicology, 2004, 24, 107-113.

(56) References Cited

OTHER PUBLICATIONS

DeNoble, "Enhanced skin permeability by ethanol: Mechanistic studies of human stratum corneum measured by DSC and FTIR,"*Pharmaceutical Research*, vol. 4(2), p. S-59 (Apr. 1987 (Supplement)).
Dimethaid Research Inc. 2004 Annual Report (Aug. 26, 2004).
Dimethaid Research Inc. 2005 Annual Report (Aug. 29, 2005).
Dimethaid Research Inc. Press Release Entitled "Dimethaid Develops "PENNSAID® PLUS": An Innovative New Formulation for PENNSAID®" (Jul. 7, 2005).
Hoover, J.E. editor, *Dispensing of Medication: A Practical Manual on the Formulation and Dispensing of Pharmaceutical Products*. vol. 789. Mack Publishing Company, 1976. p. 147-8.
Kai, T., et al., "Mechanism of percutaneous penetration enhancement: effect of n-alkanols on the permeability barrier of hairless mouse skin,"J. of Controlled Release, 1990, 12, 103-112.
McEwan, L.E., et al., "Topical diclofenac/hyaluronic acid gel in the treatment of solar keratoses,"Aus. J. of Dermatology, 1997, 58, 187-189.
Ortonne, J.-P., et al., "3% diclofenac in 2.5% hyaluronic acid (Solaraze™) does not induce photosensitivity or phototoxicity alone or in combination with sunscreens,"Eur. J. Dermatol., 2006, 16(4), 385-390.
Ott, et al., *Exposure Analysis*, CRC Press, p. 271, 2006.
Pont, A.R., et al., "Effects of active sunscreen ingredient combinations on the topical penetration of the herbicide 2,4-dichlorophenoxyacetic acid," Toxicology and Industrial Health, 2003, 19, 1-8.
Retin-A Prescribing Information, Downloaded from Drugs.com on Jan. 19, 2015.
Solaraze® Gel (Diclofenac Sodium 3%) Prescribing Information.
Vivian, J.C., et al., "Remington: The Science and Practice of Pharmacy, 21st ed." 2005, p. 2015-2054.
Wolf, J.E. Jr., et al. "Topical 3.0% diclofenac in 2.5% hyaluronan gel in the treatment of actinic keratosis," Int. J. Dermatology, 2001, 40, 709-713.

* cited by examiner

MEAN PLASMA CONCENTRATION – TIME PROFILE FOR DIMETHYL SULFOXIDE ($\mu g/mL$)

ANALYTE = DIMETHYL SULFOXIDE

MEAN PLASMA CONCENTRATION – TIME PROFILE FOR DICLOFENAC SODIUM (ng/mL)

ANALYTE = DICLOFENAC SODIUM

LOG DICLOFENAC PLASMA CONCENTRATION VERSUS TIME AFTER SINGLE AND MULTIPLE DOSE APPLICATION OF A TOPICAL SOLUTION CONTAINING 1.5% w/w DICLOFENAC SODIUM AND 45.5% DMSO

ANALYSIS OF ELIMINATION RATE CONSTANT ($K_{el}$) SINGLE AND MULTI DOSE APPLICATION OF A TOPICAL SOLUTION CONTAINING 1.5% w/w DICLOFENAC SODIUM AND 45.5% DMSO

Figure 1. Dispense 10 drops of PENNSAID® at a time

Figure 2. Spread PENNSAID® evenly on the front, and sides of your knee

Figure 3. Spread PENNSAID® evenly on the back of your knee

TREATMENT OF PAIN WITH TOPICAL DICLOFENAC

CROSS-REFERENCE TO RELATED APPLICATIONS

This application is a continuation of U.S. patent application Ser. No. 12/660,865, filed Mar. 4, 2010, which application is a continuation-in-part (CIP) of U.S. patent application Ser. No. 12/459,998, filed Jul. 10, 2009, which in turn claims priority to U.S. Provisional Patent Application 61/211,600 filed Mar. 31, 2009, the disclosures of which are herein incorporated by reference in their entireties.

FIELD

The field involves the delivery of compounds useful for pain relief, including diclofenac formulations, methods of use thereof, articles of manufacture and kits that include providing novel preclinical, clinical and other information to users.

BACKGROUND

The following includes information that may be useful in understanding the present invention. It is not an admission that any of the information provided herein is prior art, or relevant, to the presently described or claimed inventions, or that any publication or document that is specifically or implicitly referenced is prior art.

Today, pain has become the universal disorder, a serious and costly public health issue, and a challenge for family, friends, and health care providers who must give support to the individual suffering from the physical as well as the emotional consequences of pain. In general, there are two basic types of pain, acute and chronic. Acute pain, for the most part, results from disease, inflammation, or injury to tissues. This type of pain generally comes on suddenly, for example, after trauma or surgery. In some instances, it can become chronic. Chronic pain is widely believed to represent disease itself. Chronic pain persists over a longer period of time than acute pain and is resistant to most medical treatments. It can, and often does, cause severe problems for patients.

Arthritis is considered to be one of the most pervasive diseases in the United States and a leading cause of disability. According to the Centers for Disease Control and Prevention, it is estimated that 1 of every 3 Americans is affected by one or more of the more than 100 types of arthritis. Pain, particularly of the joints throughout the body, characterizes arthritis. Psoriasis, primarily a skin disorder, can progress to psoriatic arthritis if left untreated. Rheumatoid arthritis, osteoarthritis, and ankylosing spondylitis are all examples of degenerative arthritic diseases.

In addition to, for example, arthritic causes, normal function of a joint and its movement, and other portions of the body, can be severely impaired as a result of trauma or following orthopedic and other surgical procedures. This may result in tenderness, aching, pain, and lengthy recovery times, as well as loss of joint mobility or reduced range of motion, tonicity, or elasticity of the joint/articular structures, such as for example, muscle, tendon, capsule, bone, or ligament. Reduced joint mobility may also involve permanently altered or shortened joint or tissue architecture. Altered or abnormal joint mobility or joint architecture may also be associated with or caused by a variety of injuries and conditions such as, for example, metabolic disorders, ischemia, injury to joint, capsule, bone, cartilage, tendon, ligament or muscle, fractures, subluxation, dislocation, crush injuries, prolonged immobilization (e.g., immobilization of a joint in a cast or splint), and paralysis.

When non-pharmacological measures are not sufficient to control the symptoms of osteoarthritis, current evidence-based guidelines support pharmacological treatment with acetaminophen or oral nonsteroidal anti-inflammatory drugs ("NSAID"s) (American College of Rheumatology Subcommittee on Osteoarthritis Guidelines. Recommendations for the medical management of osteoarthritis of the hip and knee: 2000 update. *Arthritis Rheum.* 2000; 43:1905-15; National Collaborating Centre for Chronic Conditions. Osteoarthritis: National clinical guideline for care and management in adults. London: Royal College Physicians, 2008. Zhang W, et al., *Osteoarthritis Cartilage* 2007; 15:981-1000; Zhang W, et al., *Osteoarthritis Cartilage* 2008; 16:137-62. Acetaminophen has been linked with an increased risk of hepatic, hypertensive and cardiovascular adverse effects (e.g., Chan A T, et al., *Circulation*. 2006; 113:1578-87. Epub 2006 Mar. 13; Pincus T, et al., *Ann Rheum Dis*. 2004; 63:931-9).

NSAIDs are more effective (Towheed T E, *J Rheumatol*. 2006; 33:567-73) and carry more well-known gastrointestinal and cardiovascular risk (e.g., Antman E M, et al. Use of nonsteroidal anti-inflammatory drugs: an update for Clinicians: a scientific statement from the American Heart Association. *Circulation*. 2007; 115:1634-42; Chan A T, et al. Nonsteroidal anti-inflammatory drugs, acetaminophen, and the risk of cardiovascular events. *Circulation*. 2006; 113: 1578-87). The attempt to minimize the risk of both morbidity and potential mortality by prescribing COX-2 selective NSAIDs ('coxibs') has not achieved the goal (Kearney P M, et al. *BMJ*. 2006; 332:1302-8; Mamdani M, et al., *BMJ*. 2004; 328:1415-6).

Diclofenac is used, most commonly, as the sodium or potassium salt for relief from pain and inflammation such as musculoskeletal and joint disorders including rheumatoid arthritis, osteoarthritis, and ankylosing spondylitis. U.S. Pat. Nos. 4,575,515 and 4,652,557 disclose topical NSAID compositions, one of which, consisting of 1.5% diclofenac sodium, 45.5% dimethylsulphoxide ("DMSO"), ethanol, propylene glycol, glycerine, and water, has been shown to be effective in the treatment of chronic osteoarthritis (e.g., Towheed, *Journal of Rheumatology* 33:3 567-573 (2006); Oregon Evidence Based Practice Center entitled "Comparative Safety and Effectiveness of Analgesics for Osteoarthritis," AHRQ Pub. No. 06-EHC09-EF).

The skin provides a protective barrier against foreign materials and infection. In mammals this barrier is created primarily by the outermost epidermal layer, the stratum corneum. The stratum corneum is comprised of flat, extended, enucleated cells, termed corneocytes, the periphery of which comprises a highly insoluble protein and lipid structure, called the cornified envelope ("CE"), surrounded by lipids. (Downing et al., Dermatology in General Medicine, Fitzpatrick, et al., eds., pp. 210-221 (1993); Ponec, M, The Keratinocyte Handbook, Leigh, et al., eds., pp. 351-363 (1994)). The CE is composed of polar lipids, such as ceramides, sterols, and fatty acids, and a complicated network of cross-linked proteins; however, the cytoplasm of stratum corneum cells remains polar and aqueous. The stratum corneum is extremely thin (some 20 microns) but provides a substantial barrier. Nevertheless, the skin has been considered as a route for the administration of drugs. Various transdermal delivery systems achieve epidermal penetration by using a skin penetration enhancing vehicle.

Topical NSAIDs present a safer potential alternative to oral therapy, with decreased systemic exposure to the active NSAID molecule. While previous reviews (Mason L, et al., *BMC Musculoskelet Disord.* 2004; 5:28) have suggested that topical NSAIDs are effective for osteoarthritis, Lin et al. (*BMJ.* 2004; 329:324-6) in their meta-analysis of the same studies stressed that the various products showed symptom relief at 1 or 2 weeks but loss of benefit at 4 weeks, and rejected them as there was insufficient evidence to justify a recommendation of long-term use.

Subsequently published randomized controlled studies have described a penetrating topical diclofenac solution in a dimethyl sulfoxide (DMSO)—containing vehicle as efficacious and safe in relieving the symptoms of primary osteoarthritis of the knee over 4-, 6-, and 12-week treatment periods (Baer P A, et al. *BMC Musculoskelet Disord.* 2005; 6:44; Bookman A A, et al. CMAJ. 2004; 171:333-8; Roth S H, Shainhouse J Z. *Arch Intern Med.* 2004; 164:2017-23; Tugwell P S, et al. *J Rheumatol.* 2004; 31:2002-12). Recent topical NSAID reviews and meta-analyses (Banning M., *Br J Community Nurs* 2006; 11:487-92; Banning M., *Expert Opin Pharmacother* 2008; 9:2921-9; Biswal S, et al., *J Rheumatol.* 2006; 33:1841-4; Haynes S, Gemmell H., *Clinical Chiropractic* 2007; 10:126-38; Moore R A, et al., *Rheum Dis Clin N Am* 2008; 34:415-32; Ozguney I, *Expert Opin Pharmacother* 2008; 9:1805-16; Towheed T E, *J Rheumatol.* 2006; 33:567-73; Zacher J, et al., *Current Medical Research and Opinions* 2008; 24(4):925-950) have evaluated the data from these topical diclofenac solution studies, and subsequently published national guidelines (Chou R, et al. Comparative Effectiveness and Safety of Analgesics for Osteoarthritis. Comparative Effectiveness Review No. 4. Rockville, Md.: Agency for Healthcare Research and Quality. September 2006. Available at: www.effectivehealthcare.ahrq.gov/reports/final.cfm; National Collaborating Centre for Chronic Conditions. Osteoarthritis: National clinical guideline for care and management in adults. London: Royal College Physicians, 2008. Tannenbaum H, et al., J Rheumatol. 2006; 33:140-57; Zhang W, et al. 2007, supra; Zhang W, et al. 2008 supra) have cited these studies as evidence for the use of topical NSAIDs as first line therapy for osteoarthritis. Topical diclofenac solution is used for the treatment of osteoarthritis and is currently approved for sale in Canada and several European countries.

The efficacy of topical NSAIDs, such as topical diclofenac solution, is thought to be due to local action of the active NSAID molecule following its penetration through the skin to the tissue sites of inflammation and pain. Diclofenac sodium is a member of the arylacanoic acid group of NSAIDs with lipophilic properties that limit its percutaneous penetration (Nishihata T, et al., *Chem. Pharm. Bull* 1987; 35:3807-12). The biological property of DMSO to enhance skin penetration of both hydrophilic and lipophilic molecules is known (Williams A C, Barry B W, *Adv Drug Deliv Rev* 2004; 56:603-18), with recent research focusing on the mechanism of enhancement (Gurtovenko A A, Anwar J, *J Phys Chem B* 2007; 111:10453-60). The percutaneous absorption of diclofenac following a multidose regimen of a topical diclofenac solution (based on a DMSO-containing vehicle) was significantly enhanced compared to an aqueous diclofenac formulation without DMSO (Hewitt, P G, et al., *Pharmacol Res.* 1998; 15:988-92). Within the extensive literature on DMSO are unsubstantiated claims of therapeutic efficacy in the treatment of osteoarthritis, but no efficacy of DMSO vehicle was shown in a previous, 4-week randomized controlled study of a topical diclofenac solution (Bookman A A, et al. Effect of a topical diclofenac solution for relieving symptoms of primary osteoarthritis of the knee: a randomized controlled trial. *CMAJ.* 2004; 171:333-8).

There remains a need in the art for methods of dosing topical diclofenac formulations, and providing users and prescribers with information regarding drug product attributes and desired therapeutic effects as well as instructions on uses in conjunction with other topical agents. Such needs are met by the inventions and discoveries provided herein.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or nonlimiting embodiments identified in this Brief Summary, which is included for purposes of illustration only and not restriction.

Disclosed herein are methods of treatment and methods of manufacturing and using a topical diclofenac pharmaceutical product and related articles and kits. Also disclosed herein are methods of preventing or treating pain, including joint pain, and arthritis, including osteoarthritis.

In one nonlimiting embodiment, a method of using topical diclofenac, and related methods of treatment, comprises informing a user of certain information regarding topical diclofenac, for example, a topical diclofenac solution comprising or consisting essentially of 1.5% diclofenac sodium (2-[(2,6-dichlorophenyl)amino]benzeneacetic acid, monosodium salt), 45.5% DMSO, ethanol, propylene glycol, glycerine, and water (sometimes referred to herein as "Pennsaid"), said information comprising one or more of the following: (1) clinical effects of topical diclofenac dosing, including, for example, (a) the effects of particular four times per day ("QID") dosing; (b) the effects of QID dosing in one or more clinical trials; (c) results from a 12-week, double-blind controlled trial of topical diclofenac in a solution containing dimethyl sulfoxide in subjects with osteoarthritis of the knee which compared the performance of said topical diclofenac solution against a vehicle solution containing 45.5% dimethyl sulfoxide and a placebo solution containing 2.3% dimethyl sulfoxide; (d) pharmacokinetic results from one or more studies in which single and multiple doses of a topical diclofenac in a solution containing dimethyl sulfoxide was applied topically to healthy human volunteers; (2) an adverse event profile of a topical diclofenac, including, for example (a) that concomitant use of oral NSAIDs with topical diclofenac resulted in a higher rate of rectal hemorrhage, more frequent abnormal creatinine, urea and hemoglobin; (b) that in a controlled trial, a higher rate of contact dermatitis with vesicles was observed after treatment of 152 subjects with the combination of topical diclofenac and oral diclofenac; (c) the results of a clinical study demonstrating that the addition of topical diclofenac to oral diclofenac did not cause an elevation of liver transaminases in osteoarthritis patients over use of oral diclofenac alone; (3) preclinical study results with topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (4) a statement that, once dry, sunscreen, insect repellant, lotion, moisturizer, cosmetics, and/or other topical products can be applied to an area previously treated with a topical diclofenac solution (e.g., Pennsaid®).

In another nonlimiting embodiment, a method of using topical diclofenac for the treatment of osteoarthritis, and related methods of treatment, comprises providing a patient with said topical diclofenac and providing certain information to the patient regarding said topical diclofenac, for example, a topical diclofenac solution comprising or consisting essentially of 1.5% diclofenac sodium (2-[(2,6-dichlorophenyl)amino]benzeneacetic acid, monosodium salt), 45.5% DMSO, ethanol, propylene glycol, glycerine, and water (sometimes referred to herein as "Pennsaid"), said information comprising one or more of the following: (1) clinical effects of topical diclofenac dosing, including, for example, (a) the effects of particular four times per day ("QID") dosing; (b) the effects of QID dosing in one or more clinical trials; (c) results from a 12-week, double-blind controlled trial of topical diclofenac in a solution containing dimethyl sulfoxide in subjects with osteoarthritis of the knee which compared the performance of said topical diclofenac solution against a vehicle solution containing 45.5% dimethyl sulfoxide and a placebo solution containing 2.3% dimethyl sulfoxide; (d) pharmacokinetic results from one or more studies in which single and multiple doses of a topical diclofenac in a solution containing dimethyl sulfoxide was applied topically to healthy human volunteers; (2) an adverse event profile of a topical diclofenac, including, for example (a) that concomitant use of oral NSAIDs with topical diclofenac resulted in a higher rate of rectal hemorrhage, more frequent abnormal creatinine, urea and hemoglobin; (b) that in a controlled trial, a higher rate of contact dermatitis with vesicles was observed after treatment of 152 subjects with the combination of topical diclofenac and oral diclofenac; (c) the results of a clinical study demonstrating that the addition of topical diclofenac to oral diclofenac did not cause an elevation of liver transaminases in osteoarthritis patients over use of oral diclofenac alone; (3) preclinical study results with topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (4) a statement that, once dry, sunscreen, insect repellant, lotion, moisturizer, cosmetics, and/or other topical products can be applied to an area previously treated with a topical diclofenac solution (e.g., Pennsaid®). In one nonlimiting embodiment the method is used to treat osteoarthritis in patients with osteoarthritis of the knee. In another non-limiting embodiment the patient is further informed of the results of pharmacokinetic studies of said topical diclofenac solution in healthy human volunteers in which the measured plasma half life of diclofenac following a single dose application was shorter than said the measured plasma half life of diclofenac following a multi-dose application.

In another nonlimiting embodiment, a method of using topical diclofenac, for example, a topical diclofenac solution comprising or consisting essentially of 1.5% diclofenac sodium, 45.5% DMSO, ethanol, propylene glycol, glycerine, and water, and related methods of treatment, comprises obtaining topical diclofenac from a container providing information regarding (1) clinical effects of topical diclofenac dosing, including, for example, (a) the effects of particular QID dosing; (b) the effects of QID dosing in one or more clinical trials; (c) results from a 12-week, double-blind controlled trial of topical diclofenac in a solution containing dimethyl sulfoxide in subjects with osteoarthritis of the knee which compared the performance of said topical diclofenac solution against a vehicle solution containing 45.5% dimethyl sulfoxide and a placebo solution containing 2.3% dimethyl sulfoxide; (d) pharmacokinetic results from one or more studies in which single and multiple doses of a topical diclofenac in a solution containing dimethyl sulfoxide was applied topically to healthy human volunteers; (2) an adverse event profile of topical diclofenac, including, for example (a) that concomitant use of oral NSAIDs with topical diclofenac resulted in a higher rate of rectal hemorrhage, more frequent abnormal creatinine, urea and hemoglobin; (b) that in a controlled trial, a higher rate of contact dermatitis with vesicles was observed after treatment of 152 subjects with the combination of a topical diclofenac and oral diclofenac; (c) the results of a clinical study demonstrating that the addition of topical diclofenac to oral diclofenac did not cause an elevation of liver transaminases in osteoarthritis patients over use of oral diclofenac alone; (3) preclinical study results with topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (4) a statement that, once dry, sunscreen, insect repellant, lotion, moisturizer, cosmetics, and/or other topical products can be applied to an area previously treated with a topical diclofenac solution (e.g., Pennsaid®).

In still yet another nonlimiting embodiment, a method of using topical diclofenac, for example, a topical diclofenac solution comprising or consisting essentially of 1.5% diclofenac sodium, 45.5% DMSO, ethanol, propylene glycol, glycerine, and water, and related methods of treatment, comprises providing a user with topical diclofenac, and informing the user of one or more of the following: (1) clinical effects of topical diclofenac dosing, including, for example, (a) the effects of particular QID dosing; (b) the effects of QID dosing in one or more clinical trials; (c) results from a 12-week, double-blind controlled trial of topical diclofenac in a solution containing dimethyl sulfoxide in subjects with osteoarthritis of the knee which compared the performance of said topical diclofenac solution against a vehicle solution containing 45.5% dimethyl sulfoxide and a placebo solution containing 2.3% dimethyl sulfoxide; (d) pharmacokinetic results from one or more studies in which single and multiple doses of a topical diclofenac in a solution containing dimethyl sulfoxide was applied topically to healthy human volunteers; (2) an adverse event profile of a topical diclofenac, including, for example (a) that concomitant use of oral NSAIDs with topical diclofenac resulted in a higher rate of rectal hemorrhage, more frequent abnormal creatinine, urea and hemoglobin; (b) that in a controlled trial, a higher rate of contact dermatitis with vesicles was observed after treatment of 152 subjects with the combination of topical diclofenac and oral diclofenac; (c) the results of a clinical study demonstrating that the addition of topical diclofenac to oral diclofenac did not cause an elevation of liver transaminases in osteoarthritis patients over use of oral diclofenac alone; (3) preclinical study results with topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (4) a statement that, once dry, sunscreen, insect repellant, lotion, moisturizer, cosmetics, and/or other topical products can be applied to an area previously treated with a topical diclofenac solution (e.g., Pennsaid®).

In another nonlimiting embodiment, a method of using topical diclofenac, for example, a topical diclofenac solution comprising or consisting essentially of 1.5% diclofenac sodium, 45.5% DMSO, ethanol, propylene glycol, glycerine, and water, and related methods of treatment, comprises administering a topical diclofenac DMSO formulation to a patient, wherein the administration provides a therapeutic diclofenac concentration by application (of, for example, about 40 drops) to one or both knees to a subject having osteoarthritis of the knees, and the user is informed with regard to one or more of the following: (1) clinical effects of topical diclofenac in DMSO dosing, including, for example, (a) the effects of particular QID dosing; (b) the effects of QID dosing in one or more clinical trials; (c) results from a 12-week, double-blind controlled trial of topical diclofenac in a solution containing DMSO in subjects with osteoarthritis of the knee which compared the performance of said topical diclofenac solution against a vehicle solution containing 45.5% dimethyl sulfoxide and a placebo solution containing 2.3% dimethyl sulfoxide; (d) pharmacokinetic results from one or more studies in which single and multiple doses of a topical diclofenac in a solution containing dimethyl sulfoxide was applied topically to healthy human volunteers; (2) an adverse event profile of a topical diclofenac in DMSO, including, for example (a) that concomitant use of oral NSAIDs with topical diclofenac resulted in a higher rate of rectal hemorrhage, more frequent abnormal creatinine, urea and hemoglobin; (b) that in a controlled trial, a higher rate of contact dermatitis with vesicles was observed after treatment of 152 subjects with the combination of topical diclofenac and oral diclofenac; (c) the results of a clinical study demonstrating that the addition of topical diclofenac to oral diclofenac did not cause an elevation of liver transaminases in osteoarthritis patients over use of oral diclofenac alone; (3) preclinical study results with topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (4) a statement that, once dry, sunscreen, insect repellant, lotion, moisturizer, cosmetics, and/or other topical products can be applied to an area previously treated with a topical diclofenac solution (e.g., Pennsaid®).

In yet another nonlimiting embodiment, a method of manufacturing a topical diclofenac pharmaceutical product comprises packaging a topical diclofenac dosage form, for example, a topical diclofenac solution comprising or consisting essentially of 1.5% diclofenac sodium (2-[(2,6-dichlorophenyl)amino]benzeneacetic acid, monosodium salt), 45.5% DMSO, ethanol, propylene glycol, glycerine, and water, with some or all of the following information, in written or electronic form: (1) clinical effects of topical diclofenac dosing, including, for example, (a) the effects of particular QID dosing; (b) the effects of QID dosing in one or more clinical trials; (c) results from a 12-week, double-blind controlled trial of topical diclofenac in a solution containing dimethyl sulfoxide in subjects with osteoarthritis of the knee which compared the performance of said topical diclofenac solution against a vehicle solution containing 45.5% dimethyl sulfoxide and a placebo solution containing 2.3% dimethyl sulfoxide; (d) pharmacokinetic results from one or more studies in which single and multiple doses of a topical diclofenac in a vehicle solution containing dimethyl sulfoxide was applied topically to healthy human volunteers; (2) an adverse event profile of a topical diclofenac, including, for example (a) that concomitant use of oral NSAIDs with topical diclofenac resulted in a higher rate of rectal hemorrhage, more frequent abnormal creatinine, urea and hemoglobin; (b) that in a controlled trial, a higher rate of contact dermatitis with vesicles was observed after treatment of 152 subjects with the combination of topical diclofenac and oral diclofenac; (c) the results of a clinical study demonstrating that the addition of topical diclofenac to oral diclofenac did not cause an elevation of liver transaminases in osteoarthritis patients over use of oral diclofenac alone; (3) preclinical study results with topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (4) a statement that, once dry, sunscreen, insect repellant, lotion, moisturizer, cosmetics, and/or other topical products can be applied to an area previously treated with a topical diclofenac solution (e.g., Pennsaid®).

In one nonlimiting embodiment, an article of manufacture comprises a container containing a dosage form of topical diclofenac, for example, a topical diclofenac solution comprising or consisting essentially of 1.5% diclofenac sodium, 45.5% DMSO, ethanol, propylene glycol, glycerine, and water, wherein the container is associated with published material providing some or all of the following information: (1) clinical effects of topical diclofenac dosing, including, for example, (a) the effects of particular QID dosing; (b) the effects of QID dosing in one or more clinical trials; (c) results from a 12-week, double-blind controlled trial of topical diclofenac in a solution containing dimethyl sulfoxide in subjects with osteoarthritis of the knee which compared the performance of said topical diclofenac solution against a vehicle solution containing 45.5% dimethyl sulfoxide and a placebo solution containing 2.3% dimethyl sulfoxide; (d) pharmacokinetic results from one or more studies in which single and multiple doses of a topical diclofenac in a solution containing dimethyl sulfoxide was applied topically to healthy human volunteers; (2) an adverse event profile of a topical diclofenac, including, for example (a) that concomitant use of oral NSAIDs with topical diclofenac resulted in a higher rate of rectal hemorrhage, more frequent abnormal creatinine, urea and hemoglobin; (b) that in a controlled trial, a higher rate of contact dermatitis with vesicles was observed after treatment of 152 subjects with the combination of topical diclofenac and oral diclofenac; (c) the results of a clinical study demonstrating that the addition of topical diclofenac to oral diclofenac did not cause an elevation of liver transaminases in osteoarthritis patients over use of oral diclofenac alone; (3) preclinical study results with topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (4) a statement that, once dry sunscreen, insect repellant, lotion, moisturizer, cosmetics, and/or other topical products can be applied to an area previously treated with a topical diclofenac solution (e.g., Pennsaid®).

In one nonlimiting embodiment, information regarding the clinical effects of dosing of a topical diclofenac solution includes the effects of 40-drop QID dosing of said topical diclofenac solution, and/or the effects of 40-drop QID dosing of said topical diclofenac solution in one or more clinical trials.

In one nonlimiting embodiment, the article of manufacture is a kit. Thus, one aspect of the invention provides a novel kit of parts comprising topical diclofenac (for example, a topical diclofenac solution or gel as described, or referenced, herein) and information informing a user or prescriber of novel results from preclinical and clinical studies.

In one nonlimiting embodiment, or in any of the methods described herein, the user or prescriber is informed of the results of or more preclinical studies in which concomitant use of topical diclofenac with other topical products, including DEET (active ingredient in insect repellent), 2,4-D (active ingredient in commonly used pesticides) and oxybenzone (active ingredient in sunscreens), was investigated. In one aspect of this embodiment, the user or prescriber is informed that repeated application of topical diclofenac did not enhance the systemic absorption of these products. In another aspect of this embodiment, the user or prescriber is informed that before applying sunscreen, insect repellant, lotion, moisturizer, cosmetics, or other topical medication to the same skin surface of the knee treated with topical diclofenac, one should wait until the treated area is dry, which occurs most often within from about 10-15 or about 30 minutes. In another aspect of this embodiment, including in any of the methods described herein, the user or prescriber is informed that concomitant use of topical diclofenac and sunscreens and insect repellants is safe. In another aspect of this embodiment, including in any of the methods described herein, the user or prescriber is informed that use of topical diclofenac does not reduce the efficacy of a sunscreen. In another aspect of this embodiment, including in any of the methods described herein, the user or prescriber is informed that use of topical diclofenac does not reduce the efficacy of an insect repellant.

In one nonlimiting embodiment, or any of the methods described herein, a user may also be informed of the effects of use of other topical products in conjunction with topical diclofenac in DMSO, including, for example, that concomitant topical use of diclofenac in DMSO by repeated application with other topical products, including DEET, 2,4-D and/or oxybenzone (active ingredient in sunscreens) did not enhance the systemic absorption of these products; and/or (b) the effect of the use of topical diclofenac in DMSO on absorption of environmental toxins, including, for example, the results of a study showing that repeated topical application of diclofenac in DMSO did not increase systemic environmental toxin exposure.

In one nonlimiting embodiment, or in any of the methods described herein, the user or prescriber is informed of the results of a transepidermal water loss study in which no alteration in skin barrier function following chronic use of topical diclofenac was found. In one aspect of this embodiment, including in any of the methods described herein, the user or prescriber is informed that the study was performed on human volunteers' skin.

In one nonlimiting embodiment, or in any of the methods described herein, the user or prescriber is informed of the pharmacokinetic results from studies in which single and multiple doses of a topical diclofenac in a vehicle solution containing dimethyl sulfoxide was applied topically to healthy human volunteers;

In one nonlimiting embodiment, or in any of the methods described herein, the user or prescriber is informed that in clinical trials the combination of topical diclofenac and oral diclofenac, compared to oral diclofenac alone, resulted in a higher rate of rectal hemorrhage (3% vs. less than 1%), and more frequent abnormal creatinine (12% vs. 7%), urea (20% vs. 12%), and hemoglobin (13% vs. 9%), but no difference in elevation of liver transaminases.

In one nonlimiting embodiment, or in any of the methods described herein, the user or prescriber is informed that the diclofenac half life and elimination constant $K_{el}$ for a topical diclofenac solution comprising or consisting essentially of 1.5% diclofenac sodium, 45.5% DMSO, ethanol, propylene glycol, glycerine, and water is statistically significantly different depending on whether the solution is applied as a single dose or as multiple doses.

In one nonlimiting embodiment, the user or prescriber is informed of the results of a clinical study demonstrating that the addition of topical diclofenac to oral diclofenac did not increase the incidence of certain systemic adverse events in osteoarthritis patients. In one aspect of this embodiment, the user or prescriber is further informed that the combination of topical diclofenac and oral diclofenac did not increase the incidence of digestive system events over oral diclofenac alone. In another nonlimiting embodiment, the user or prescriber is informed of a study showing that administration of topical diclofenac results in less frequent adverse events associated with the NSAID class than oral diclofenac alone and/or the results of a clinical study demonstrating that the addition of topical diclofenac to oral diclofenac did not cause an elevation of liver transaminases in osteoarthritis patients over use of oral diclofenac alone.

In another nonlimiting embodiment, the user or prescriber is informed of the results of a clinical trial in which one knee was successfully treated with topical diclofenac even though most subjects had bilateral osteoarthritis of the knees. In one aspect of this embodiment, the user or prescriber is further informed that topical diclofenac may be applied to only one knee despite the existence of bilateral osteoarthritis.

In another nonlimiting embodiment, the user or prescriber is informed that a regimen of topical diclofenac and oral diclofenac is useful for treating an individual with persistent or breakthrough knee pain despite using an oral NSAID.

In another nonlimiting embodiment, the user or prescriber is informed that topical diclofenac, or a regimen of topical diclofenac and oral diclofenac, is useful when topical diclofenac is applied to only one knee of a subject with osteoarthritis even though both knees of an individual may be affected.

In yet another nonlimiting embodiment, the user is provided with some or all of the topical diclofenac clinical and preclinical information described herein for purposes of enhancing the safety profile of topical diclofenac.

The topical diclofenac composition will comprise diclofenac and at least one transdermal penetration enhancer in an amount sufficient to aid in the delivery of a therapeutically effective amount of diclofenac to a desired area. The topical diclofenac may also include one or more pharmaceutically acceptable carriers, thickening agents, solubilizing agents, dispersants, etc.

In certain embodiments, the diclofenac is in the form of a pharmaceutically acceptable salt or free acid. Examples of pharmaceutically acceptable salts include metal salts, including alkali metal, alkaline earth metal, and nitrogen-based salts such as ammonium salts. Sodium, potassium, epolamine and diethylamine salts are preferred. In one preferred embodiment the diclofenac is diclofenac monosodium salt.

In one nonlimiting embodiment, the topical diclofenac is a solution.

In another nonlimiting embodiment, the topical diclofenac is a gel.

In one nonlimiting embodiment, the topical diclofenac is a solution that comprises or consists essentially of diclofenac and between about 40% and about 85% DMSO by weight of the solution, preferably between about 40% and about 60% DMSO by weight of the solution, more preferably between about 40% and about 50% DMSO by weight of the solution, still more preferably between about 42.5% and about 48.5% DMSO by weight of the solution, and most preferably about 45.5% DMSO by weight of the solution; a polyalcohol, preferably having 3-5 carbon atoms, for the retention of moisture in the skin, which in certain embodiments is glycerol or glycerine; a dispersant for assisting to disperse the components in solution to provide a homogeneous solution when applied to the skin and when penetrating the skin, which in one embodiment is propylene glycol; and water.

In one nonlimiting embodiment, the topical diclofenac is a solution comprising or consisting essentially of 1.5% w/w diclofenac sodium (2-[(2,6-dichlorophenyl)amino]benzeneacetic acid, monosodium salt) and 45.5% w/w dimethyl sulfoxide.

In another nonlimiting embodiment, the topical diclofenac is a solution that comprises or consists essentially of 1.5% diclofenac sodium (2-[(2,6-dichlorophenyl)amino]benzeneacetic acid, monosodium salt), 45.5% DMSO, ethanol, propylene glycol, glycerine, and water.

In another nonlimiting embodiment, the topical diclofenac is a gel formulation according to PCT/US2007/081674 (International Publication No. WO 2008/049020 A2), the contents of which are incorporated herein in their entirety by this reference. The topical diclofenac may be any of the formulations described or claimed therein. In another nonlimiting embodiment, the topical diclofenac is a gel formulation according to US Patent Application No. 20080300311 (published Dec. 4, 2008), the contents of which are incorporated herein in their entirety by this reference. The topical diclofenac may be any of the formulations described or claimed therein.

In another nonlimiting embodiment, the topical diclofenac is a gel formulation comprising diclofenac (e.g., diclofenac sodium), dimethyl sulfoxide, ethanol, propylene glycol, one or more thickening agents, and water. In one aspect of this embodiment, the topical diclofenac gel formulation further comprises glycerol. In another aspect, the thickening agent is selected from the group consisting of cellulose polymers, carbomer polymers, a carbomer derivative, a cellulose derivative, polyvinyl alcohol, poloxamers, polysaccharides, and mixtures thereof.

In another nonlimiting embodiment, the topical diclofenac is a gel formulation comprising or consisting essentially of 1-5% w/w diclofenac (preferably diclofenac monosodium); 30-60% w/w dimethyl sulfoxide; 1-50% w/w ethanol; 1-15% w/w propylene glycol; a thickener; and water (added to make 100% w/w). In a preferred aspect of this embodiment, the gel formulation has a viscosity of 10-50,000 centipoise.

In another nonlimiting embodiment, the topical diclofenac is a gel formulation comprising or consisting essentially of about 2% w/w diclofenac (preferably diclofenac monosodium); about 45.5% w/w dimethyl sulfoxide; about 23-29% w/w ethanol; about 11% w/w propylene glycol; about 0-6% w/w hydroxypropylcellulose (HY119); and water (added to make 100% w/w). In a preferred aspect of this embodiment, the gel formulation has a viscosity of 500-5,000 centipoise.

In another nonlimiting embodiment, the topical diclofenac is a gel formulation comprising or consisting essentially of diclofenac (preferably diclofenac monosodium) at a concentration selected from the group consisting of 1, 1.5, 2 and 3% w/w; dimethyl sulfoxide at a concentration selected from the group consisting of 42, 43, 44, 45, 45.5 46, 47, 48 and 49% w/w and fractions in between; ethanol at 23-29% w/w; propylene glycol at a concentration selected from the group consisting of 9, 10, 11, 12, 13% w/w and fractions in between; hydroxypropylcellulose (HY119) at 0-6% w/w; and water (included in an amount sufficient to make 100% w/w). In a preferred aspect of this embodiment, the gel formulation has a viscosity of about 500-5000 centipoise.

In certain embodiments, the above-described topical diclofenac gel formulations include 1-5% glycerol. In such embodiments, the gel formulation will have a drying rate and a transdermal flux that are greater than a comparative liquid topical diclofenac formulation. In other embodiments, the above-described topical diclofenac gel formulations will have a pH of about 6.0 to about 10.0.

In another nonlimiting embodiment, the topical diclofenac is a gel formulation comprising diclofenac (e.g., diclofenac sodium), ethanol, dimethyl sulfoxide, propylene glycol, hydroxypropylcellulose and water. In one aspect of this embodiment, the hydroxypropylcellulose is substituted with alklycellulose, hydroxyalkylcellulose, carboxyalkylcellulose, or sodium carboxyalklycellulose, where alkyl is methyl, ethyl or propyl, or a mixture thereof.

In another aspect of the present invention, some or all of the user information described herein is provided and pain is reduced in a supporting body structure of a subject, including joints, muscles, tendons, ligaments, cartilage and skin, by topically administering to a subject in need thereof a pharmaceutical composition comprising a therapeutically effective amount of diclofenac in dimethyl sulfoxide, preferably 45.5% w/w dimethyl sulfoxide, or a pharmaceutical composition comprising a therapeutically effective amount of diclofenac in a gel formulation, as described herein, in PCT/US2007/081674, or in US Patent Application No. 20080300311. In another nonlimiting embodiment, pain in the musculoskeletal system of a subject is reduced. In another nonlimiting embodiment, pain in a supporting body structure of a subject and/or in the musculoskeletal system of a subject is reduced.

Various uses of the information provided herein following new clinical and preclinical studies include uses for treatment, or in the manufacture or preparation of formulations, compositions, articles of manufacture and kits.

The invention also includes methods employing topical diclofenac, kits and articles of manufacture useful for pain relief or prevention in the treatment of a subject, including in the treatment of a subject following an invasive medical procedure or surgery, including an orthopedic procedure or surgery, or a subject predisposed to or otherwise at risk for pain, wherein said methods, kits and articles of manufacture comprise some or all of the user information described herein. The topical diclofenac described herein is administered to a site of pain (acute or chronic, for example) and/or proximally thereto (including, for example, areas of reflected or secondary pain). Thus, for example, some or all of the user information described herein is provided and the topical diclofenac is administered to the skin at a site of pain and/or to skin locations proximal thereto in a supporting body structure of a subject, including joints, muscles, tendons, ligaments, cartilage and skin (including any one or more of these, together, or in any combination), and/or in the musculoskeletal system, by topical administration as provided herein, whereby pain is reduced.

In one aspect, the present invention is directed to a method for reducing pain in a supporting body structure of a subject, comprising topically administering to said subject in need thereof a pharmaceutical composition comprising a therapeutically effective amount of a transdermal diclofenac solution or gel formulation comprising DMSO, whereby pain is reduced, and providing to a user some or all of the clinical and preclinical information described herein. According to one nonlimiting embodiment, the supporting body structure is a joint. According to another nonlimiting embodiment, the supporting body structure is selected from the group consisting of muscles, bones, tendons, ligaments and cartilage. These methods are suitable for treating a subject suffering from arthritis. Conditions which may be treated include osteoarthritis, rheumatoid arthritis, and anklyosing spondylitis.

In a further nonlimiting embodiment this method is suitable for treating a subject suffering from acute pain. Suitable pain conditions for treatment by this method include back pain, knee pain, hip pain, shoulder pain, ankle or leg pain, hand pain or finger pain, in which a user is also provided with some or all of the clinical and preclinical information described herein. In an alternate nonlimiting embodiment, the subject is suffering from chronic pain, which may include back pain, knee pain, hip pain, shoulder pain, ankle or leg pain, hand pain or finger pain. In another nonlimiting embodiment, the subject is suffering from postoperative pain.

In another aspect, the present invention is directed to a method for applying multiple topical agents to an subject with pain comprising topically administering a pharmaceutical composition comprising a therapeutically effective amount of a topical diclofenac comprising diclofenac in DMSO, waiting for the treated area to dry (the time for which can be dependent on individual skin characteristics, environmental conditions such as temperature and humidity, and surface area, being often about 5-30 minutes, or about 5-20 minutes, for example, or typically about 10 minutes or less for a topical diclofenac preparation, including a topical diclofenac solution as described in the Examples), and applying another topical agent(s). In one nonlimiting embodiment, the subject has osteoarthritis. In another nonlimiting embodiment, the subject has osteoarthritis of the knee. In one embodiment, the topical agent administered after the topical diclofenac is a sunscreen or an insect repellant.

In another nonlimiting embodiment, the invention includes a method of protecting a subject with osteoarthritis from UV exposure and alleviating the signs and symptoms of osteoarthritis in the subject comprising the steps of applying a therapeutically effective amount of a transdermal diclofenac solution or gel formulation comprising diclofenac in DMSO; waiting for the treated area to dry (the time for which can be dependent on individual skin characteristics, environmental conditions such as temperature and humidity, and surface area, being often about 5-30 minutes, or about 5-20 minutes, for example, or typically about 10 minutes or less for a topical diclofenac preparation, including a topical diclofenac solution as described in the Examples), and applying sunscreen to all or a portion of the same area of treatment.

In a further aspect, provided is an article of manufacture comprising a topical diclofenac preparation (e.g., a solution or gel formulation for transdermal administration as described herein) and a packaging material, wherein said topical diclofenac preparation comprises a pain relief effective amount of diclofenac in DMSO, wherein said packaging material comprises a label or insert that indicates that said composition may be used for reducing pain in a supporting structure, and wherein a user is also provided with some or all of the clinical and preclinical information described herein.

In another aspect, a kit of information concerning a topical diclofenac product comprising diclofenac and dimethyl sulfoxide is provided, said kit comprising information about (a) clinical effects of dosing of a topical diclofenac solution comprising 1.5% w/w diclofenac sodium and 45.5% w/w dimethyl sulfoxide, including (i) the effects of (for example, 40-drop) QID dosing of said topical diclofenac solution; (ii) the effects of (for example, 40-drop) QID dosing of said topical diclofenac solution in one or more clinical trials; (iii) results from a 12-week, double-blind, controlled trial of said topical diclofenac solution in subjects with osteoarthritis of the knee which compared the performance of said topical diclofenac solution against a vehicle solution containing 45.5% dimethyl sulfoxide and a placebo solution containing 2.3% dimethyl sulfoxide; and (iv) pharmacokinetic results from one or more studies in which single and multiple doses of a topical diclofenac in a solution containing dimethyl sulfoxide was applied topically to healthy human volunteers; (b) an adverse event profile for a topical diclofenac solution comprising 1.5% w/w diclofenac sodium and 45.5% w/w dimethyl sulfoxide, including, (i) concomitant use of oral NSAIDs with topical diclofenac resulted in a higher rate of rectal hemorrhage, more frequent abnormal creatinine, urea and hemoglobin; (ii) that in a controlled trial, a higher rate of contact dermatitis with vesicles was observed after treatment of 152 subjects with the combination of topical diclofenac and oral diclofenac; and (iii) results of a clinical study demonstrating that the addition of said topical diclofenac solution to oral diclofenac did not cause an elevation of liver transaminases over use of oral diclofenac alone; (c) preclinical study results for a topical formulation comprising dimethyl sulfoxide, including for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (d) a statement that, once dry, sunscreen, insect repellant, lotion, moisturizer, cosmetics, and/or other topical products can be applied to an area previously treated with a topical diclofenac solution (e.g., Pennsaid®).

In another aspect, a method of treating osteoarthritis of the knee is provided which comprises supplying a topical diclofenac preparation and the Attachment to the patient.

Also provided is a method of obtaining marketing authorization from a regulatory authority for a topical diclofenac product comprising referencing the kit of information.

In another embodiment, a method for distribution of a topical diclofenac product is provided, comprising the steps of (a) obtaining marketing authorization from a regulatory authority for a topical diclofenac product comprising referencing the kit of information; and providing said topical diclofenac product to one or more distributors.

These and other aspects of the present inventions, which are not limited to or by the information in this Brief Summary, are provided below.

DETAILED DESCRIPTION

Figure 1:
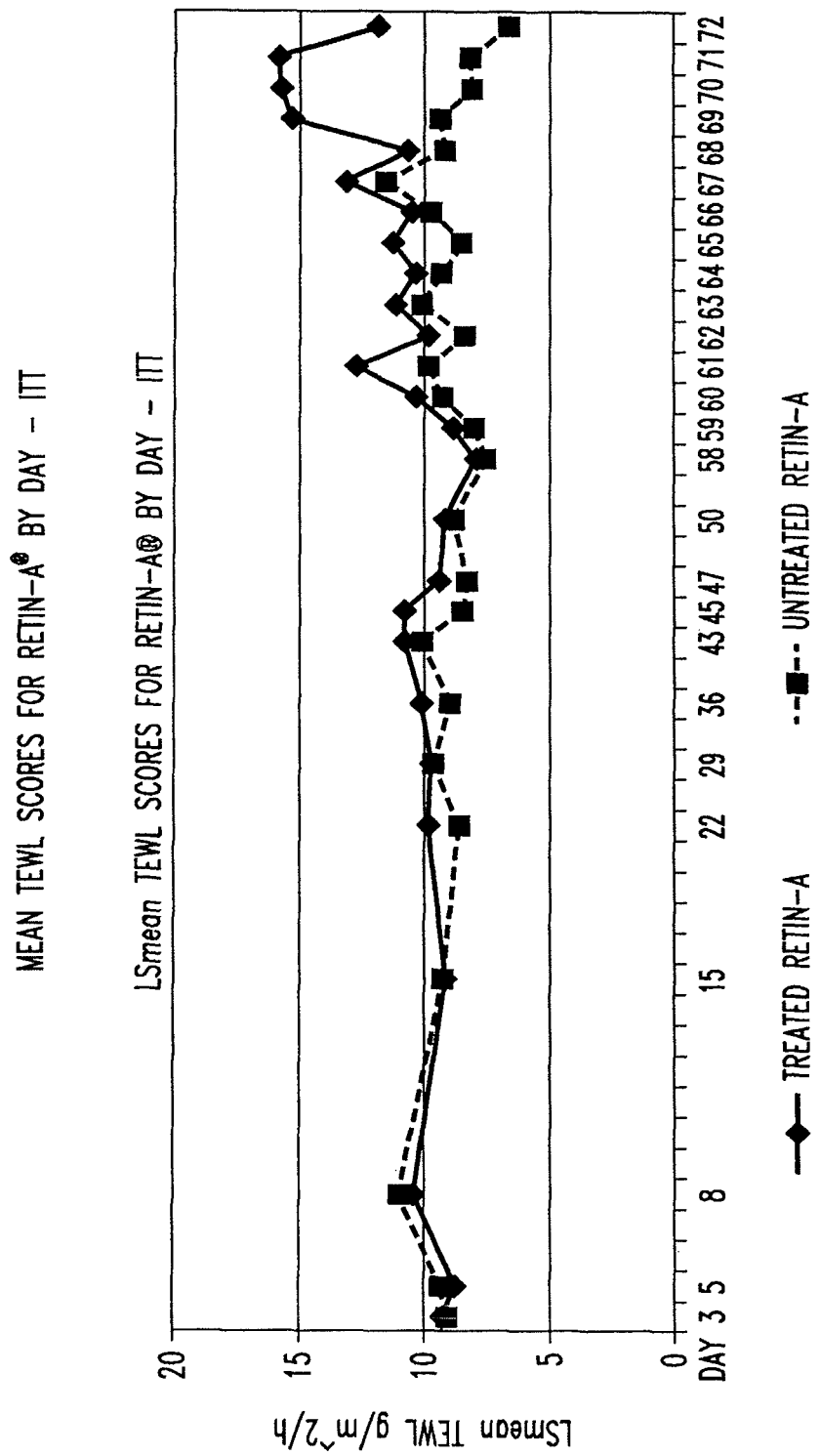
FIG. 1 shows mean TEWL scores for Retin-A® by Day-ITT.

As used herein, a "disorder" is any disorder, disease, or condition involving pain that would benefit from topical diclofenac.

"Enhancing the safety profile" of topical diclofenac means implementing actions or articles designed or intended to help reduce the incidence of adverse events associated with administration of topical diclofenac, including adverse effects associated with patient-related factors (e.g., age, gender, ethnicity, race, target illness, abnormalities of cardiovascular, gastrointestinal, renal or hepatic function, co-morbid illnesses, characteristics such as pregnancy or environment, including sun exposure) and topical diclofenac-related factors (e.g., dose, plasma level, duration of exposure, or concomitant medication).

"Informing" means referring to or providing, published material including in electronic form, for example, providing published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension. "Published" material may be in any form, including printed and electronic forms. Electronic forms include material stored in any memory or data storage format or medium (e.g., memory stick, CD, DVD, or other machine readable form), as well as materials available or accessible via the Internet or online databases, for example.

A "medical care worker" means a worker in the health care field who may need or utilize information regarding topical diclofenac including a dosage form thereof, including information on safety, efficacy, dosing, administration, or pharmacokinetics. Examples of medical workers include physicians, pharmacists, physician's assistants, nurses, aides, caretakers (which can include family members or guardians), emergency medical workers, and veterinarians.

As used herein, "musculoskeletal system" (also known as the locomotor system) refers to the system that gives animals the ability to physically move using the muscles and the skeletal system. The musculoskeletal system includes the skeleton, made by bones attached to other bones with joints and ligaments, and skeletal muscle attached to the skeleton by tendons. Particularly useful applications of the present invention include the prevention or treatment of musculoskeletal pain, including pain that affects the joints, muscles, ligaments and tendons, along with bones.

As used herein, "pain" includes acute pain and chronic pain.

A "patient" means a subject in need of medical treatment. Medical treatment can include treatment of an existing condition, such as a disease or disorder, prophylactic or preventative treatment. In some embodiments the patient is a human patient.

A "pharmaceutical supplier" means a person (other than a medical care worker), business, charitable organization, governmental organization, or other entity involved in the transfer of topical diclofenac, including a dosage form thereof, between entities, for profit or not. Examples of pharmaceutical suppliers include pharmaceutical distributors, pharmacy chains, pharmacies (online or physical), hospitals, HMOs, supermarkets, the Veterans Administration, or foreign businesses or individuals importing topical diclofenac into the United States.

As used herein, "preventing" or "prevention" means preventing in whole or in part, or ameliorating, reducing or controlling.

A "product" or "pharmaceutical product" means a dosage form of topical diclofenac plus published material and optionally packaging.

"Providing" means giving, administering, selling, distributing, transferring (for profit or not), manufacturing, compounding, or dispensing.

"Published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, a podcast, an audio recording, or other recording or electronic medium.

"Safety" means the incidence or severity of adverse events associated with administration of topical diclofenac, including adverse effects associated with patient-related factors, including as noted above, and topical diclofenac-related factors, including as noted above.

As used herein, "subject" refers to any mammal, including humans, domestic and farm animals, and zoo, sports, or pet animals, such as dogs, horses, cats, sheep, pigs, cows, etc. Non-limiting preferred mammals are a human, including adults, children, and the elderly. Non-limiting preferred sports animals are horses and dogs. Non-limiting preferred pet animals are dogs and cats.

As used herein, "supporting body structure of a subject" refers to skeletal elements, joints, muscles, tendons, ligaments, cartilage, and skin of that subject. Particularly useful applications of the present invention include the prevention or treatment of pain in and around joints, including shoulders, hips, knees, elbows, hands and fingers. Other particularly useful applications of the present invention include the prevention or treatment of pain in the knee, including pain resulting from osteoarthritis of the knee. Each of these may be treated separately, as may each of joints, muscles, tendons, ligaments, cartilage, and skin be the subject of separate treatment for pain.

As used herein, a "therapeutically effective amount" or "effective amount" in reference to the compounds or compositions of the instant invention refers to an amount sufficient to induce a desired biological, pharmaceutical, or therapeutic result. That result can be alleviation of the signs, symptoms, or causes of a disease or disorder or condition, or any other desired alteration of a biological system. In the present invention, the result will involve preventing pain.

The term "topical", as used herein, means the epicutaneous application of an agent to the skin.

Topical diclofenac solutions include any of the diclofenac solutions described or claimed herein (or described or claimed in U.S. Pat. No. 4,575,515 or 4,652,557), which are useful for the transdermal administration of diclofenac to a subject, including, for example, a formulation containing 1.5% w/w/diclofenac sodium (2-[(2,6-dichlorophenyl) amino]benzeneacetic acid, monosodium salt) and 45.5% w/w DMSO, and a formulation containing 1.5% w/w/diclofenac sodium (2-[(2,6-dichlorophenyl)amino]benzeneacetic acid, monosodium salt), 45.5% w/w DMSO ethanol, propylene glycol, glycerine, and water.

Topical diclofenac gel formulations include any one or more of the diclofenac gel formulations described or claimed herein (or described or claimed in PCT/US2007/081674 or US Patent Application No. 20080300311), which are useful for the transdermal administration of diclofenac to a subject.

The term "transdermal", as used herein, means the delivery of an agent into and/or through the skin for therapy.

The terms "treating" and "treatment" mean implementation of therapy with the intention of reducing the severity or frequency of symptoms. As used herein, the terms "treating" and "treatment" refer to both therapeutic treatment and prophylactic or preventative measures.

A "user" means a patient, a medical care worker, or a pharmaceutical supplier.

Disclosed herein are methods of using topical diclofenac formulations, articles of manufacture incorporating topical diclofenac formulations, and kits. Specifically disclosed are methods of using topical diclofenac and informing users of certain preclinical and/or clinical information.

In one nonlimiting embodiment, a method is provided in which a subject is treated for a disorder with a transdermally delivered therapeutically effective amount of topical diclofenac and a user is provided with some or all of the user information described herein. In another nonlimiting embodiment, a method is provided in which a supporting body structure or the musculoskeletal system of a subject is treated for a disorder with topical diclofenac and a user is provided with some or all of the user information described herein. In another nonlimiting embodiment, the supporting body structure is selected from joints, muscles, tendons, ligaments, cartilage and skin, and includes treatment of pain in and around joints, including shoulders, hips, knees, elbows, hands and fingers, as well as the back, particularly the lower back. In one nonlimiting embodiment the pain is acute pain. In one nonlimiting embodiment the pain is chronic pain. In one nonlimiting embodiment the pain is treated. In another nonlimiting embodiment the pain is prevented. In one preferred nonlimiting embodiment, the pain results from osteoarthritis of the knee. Preferably, the subject is a human subject.

In one nonlimiting embodiment, information provided to the user consists of, consists essentially of or comprises 1. A clinical profile for topical diclofenac including, for example
   a. the effects of particular QID dosing of diclofenac;
   b. the effects of QID dosing in one or more clinical trials;
   c. results from a 12-week, double-blind controlled trial of topical diclofenac in a solution containing dimethyl sulfoxide in subjects with osteoarthritis of the knee which compared the performance of said topical diclofenac solution against a vehicle solution containing 45.5% dimethyl sulfoxide and a placebo solution containing 2.3% dimethyl sulfoxide (for example, a 12-week, double-blind, double-dummy, randomized controlled trial of topical diclofenac in a vehicle solution containing dimethyl sulfoxide in 775 subjects);
   d. pharmacokinetic results from one or more studies in which single and multiple doses of a topical diclofenac in a vehicle solution containing dimethyl sulfoxide was applied topically to healthy human volunteers;
2. An adverse event profile for a topical diclofenac, including, for example
   a. that concomitant use of oral NSAIDs with topical diclofenac resulted in a higher rate of rectal hemorrhage, and more frequent abnormal creatinine, urea and hemoglobin (including that a combination of topical diclofenac and oral diclofenac, compared to oral diclofenac alone, resulted in a higher rate of rectal hemorrhage (3% vs. less than 1%), and more frequent abnormal creatinine (12% vs. 7%), urea (20% vs. 12%), and hemoglobin (13% vs. 9%));
   b. that in a controlled trial, a higher rate of contact dermatitis with vesicles was observed after treatment of 152 subjects with the combination of topical diclofenac and oral diclofenac;
   c. that in clinical trials; (d) the results of a clinical study demonstrating that the addition of topical diclofenac to oral diclofenac did not cause an elevation of liver transaminases in osteoarthritis patients over use of oral diclofenac alone;
3. A preclinical study profile for topical diclofenac, including, for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®);
4. A statement that, once dry, sunscreen, insect repellant, lotion, moisturizer, cosmetics, and/or other topical products can be applied to an area previously treated with a topical diclofenac solution (e.g., Pennsaid®)

This information, which may relate, for example, to a topical diclofenac containing 1.5% diclofenac sodium (2-[(2,6-dichlorophenyl)amino]benzeneacetic acid, monosodium salt), 45.5% DMSO, ethanol, propylene glycol, glycerine, and water, is sometimes referred to herein as the "Information."

Other adverse event information may include that administration of topical diclofenac does not increase the incidence of systemic adverse events over use of oral diclofenac alone; that the addition of topical diclofenac to oral diclofenac does not increase the incidence of systemic adverse events in osteoarthritis patients; the results of a clinical study demonstrating that the addition of topical diclofenac to oral diclofenac did not increase the incidence of systemic adverse events in osteoarthritis patients; and, the results of a clinical study showing that no eye lens abnormalities were observed with DMSO-vehicle or topical diclofenac solution treatment; that administration of topical diclofenac results in less frequent adverse events associated with the NSAID class than oral diclofenac alone; and, the results of a clinical study demonstrating that the addition of topical diclofenac to oral diclofenac did not cause an elevation of liver transaminases in osteoarthritis patients over use of oral diclofenac alone.

Other preclinical profile information may include the effect of the use of topical diclofenac on absorption of environmental toxins, including, for example, the results of a study showing that repeated application of topical diclofenac solution did not increase systemic environmental toxin exposure; and the effects of use of other topical products in conjunction with topical diclofenac, including, for example, that concomitant use of diclofenac topical solution by repeated application with other topical products, including DEET (active ingredient in insect repellent), 2,4-D (active ingredient in commonly used pesticides) and oxybenzone (active ingredient in sunscreens) did not enhance the systemic absorption of these products.

Other information provided to the user may include the pharmacokinetic results from one or more studies in which single and multiple doses of a topical diclofenac in a vehicle solution containing dimethyl sulfoxide was applied topically to healthy human volunteers;

Other information provided to the user may include that the diclofenac half life and elimination constant $K_{el}$ for a topical diclofenac solution comprising or consisting essentially of 1.5% diclofenac sodium, 45.5% DMSO, ethanol, propylene glycol, glycerine, and water is statistically significantly different depending on whether the solution is applied as a single dose or as multiple doses.

In one nonlimiting embodiment, a user is provided with the Information, or with some or all of the Information, or with some or all of the topical diclofenac clinical and preclinical information described herein and in the Examples, for purposes of enhancing the safety profile of topical diclofenac and/or enhancing its application to or by a subject in need thereof.

In one nonlimiting embodiment, information provided to the user comprises information regarding the clinical effects of dosing a topical diclofenac containing 1.5% diclofenac sodium (2-[(2,6-dichlorophenyl)amino]benzeneacetic acid, monosodium salt), 45.5% DMSO, ethanol, propylene glycol, glycerine, and water, including, for example, (1) the effects of particular QID dosing of diclofenac; (2) the effects of QID dosing in one or more clinical trials including the results from a 12-week, double-blind, double-dummy, randomized controlled trial of topical diclofenac in a vehicle solution containing dimethyl sulfoxide in 775 subjects with radiologically confirmed, symptomatic primary osteoarthritis of the knee; (3) the effect of treating osteoarthritis of the knee in one or more clinical trials, including the effect of treating one knee when both knees are affected with osteoarthritis; and/or (4) results of a human volunteer study on trans-epidermal water loss in which no alteration in skin barrier function was observed.

In another nonlimiting embodiment, information provided comprises information regarding the adverse event profile of a topical diclofenac containing 1.5% diclofenac sodium (2-[(2,6-dichlorophenyl)amino]benzeneacetic acid, monosodium salt), 45.5% DMSO, ethanol, propylene glycol, glycerine, and water, including, for example (1) that administration of topical diclofenac does not increase the incidence of systemic adverse events over use of oral diclofenac alone; (2) that the addition of topical diclofenac to oral diclofenac does not increase the incidence of systemic adverse events in osteoarthritis patients; (3) the results of a clinical study demonstrating that the addition of topical diclofenac to oral diclofenac did not increase the incidence of systemic adverse events in osteoarthritis patients; and/or (4) the results of a clinical study showing that no eye lens abnormalities were observed with DMSO-vehicle or topical diclofenac solution treatment.

In yet another nonlimiting embodiment, information provided comprises information regarding preclinical study results with a topical diclofenac containing 1.5% diclofenac sodium(2-[(2,6-dichlorophenyl)amino]benzeneacetic acid, monosodium salt), 45.5% DMSO, ethanol, propylene glycol, glycerine, and water, including, for example, (1) the effect of the use of the topical diclofenac on absorption of environmental toxins, including, for example, the results of a study showing that repeated application of the topical diclofenac did not increase systemic environmental toxin exposure; and, (2) the effects of use of other topical products in conjunction with the topical diclofenac, including, for example, that concomitant use of diclofenac topical solution by repeated application with other topical products, including DEET (active ingredient in insect repellent), 2,4-D (active ingredient in commonly used pesticides) and oxybenzone (active ingredient in sunscreens) did not enhance the systemic absorption of these products.

In still another nonlimiting embodiment, information provided comprises information regarding the clinical effects of topical diclofenac dosing, information regarding the adverse event profile of topical diclofenac, and/or information regarding preclinical study results with topical diclofenac, as described herein, wherein the topical diclofenac contains 1.5% diclofenac sodium (2-[(2,6-dichlorophenyl)amino] benzeneacetic acid, monosodium salt), 45.5% DMSO, ethanol, propylene glycol, glycerine, and water.

In one nonlimiting embodiment, the diclofenac is in the form of a topical diclofenac solution formulation. In another nonlimiting embodiment, the diclofenac is in the form of a topical diclofenac gel formulation.

Diclofenac sodium is a benzene-acetic acid derivative that is a nonsteroidal anti-inflammatory drug, designated chemically as 2-[(2,6-dichlorophenyl)amino]benzeneacetic acid, monosodium salt, and may be prepared by means known in the art. See, for example, U.S. Pat. No. 4,575,515.

Following synthesis a topical diclofenac solution may be formulated by methods known in the art as 1.5% w/w diclofenac sodium in DMSO (45.5% w/w). It is a clear, colorless to faintly pink-orange solution for topical application. Each 1 mL of solution may contain 16.05 mg of diclofenac sodium. In addition, the topical diclofenac solution will preferably contain the following inactive ingredients: propylene glycol, alcohol, glycerin and purified water.

In this disclosure, examples relating to new preclinical and clinical discoveries regarding topical diclofenac are provided.

While topical non-steroidal anti-inflammatory drugs are considered safe, their long-term efficacy for osteoarthritis has been suspect. Example 1 describes the results of a 12-week, double-blind, double-dummy, randomized controlled trial of a topical diclofenac solution containing 1.5% diclofenac sodium (2-[(2,6-dichlorophenyl)amino]benzeneacetic acid, monosodium salt), 45.5% DMSO, ethanol, propylene glycol, glycerine, and water was conducted in 775 subjects with radiologically confirmed, symptomatic primary osteoarthritis of the knee. This 5-arm study compared the topical diclofenac solution with a placebo solution, DMSO vehicle, oral diclofenac and a combination of the topical diclofenac solution+oral diclofenac for relieving the signs and symptoms of knee osteoarthritis. Subjects applied study solution, 40 drops QID (four times daily), and took one study tablet daily for 12 weeks. Co-primary efficacy variables were Western Ontario McMaster Universities Osteoarthritis Index ("WOMAC") pain and physical function scores and a patient overall health assessment. Secondary variables were WOMAC stiffness and patient global assessment ("PGA") of the knee osteoarthritis. The topical diclofenac solution was superior to placebo for pain ($-6.0$ vs. $-4.7$, $P=0.015$), physical function ($-15.8$ vs. $-12.3$, $P=0.034$), overall health ($-0.95$ vs. $-0.37$, $P<0.0001$), and PGA ($-1.36$ vs. $-1.01$, $P=0.016$), and was superior to DMSO vehicle for all efficacy variables. The most common adverse event was dry skin (18.2%). Surprisingly, no significant difference was observed between DMSO vehicle and placebo or between the topical diclofenac solution and oral diclofenac, yet fewer digestive system and laboratory abnormalities were observed with topical diclofenac than oral diclofenac. Further, addition of the topical diclofenac solution to oral diclofenac did not increase the incidence of systemic adverse events. Additionally, administration of topical diclofenac resulted in less frequent adverse events associated with the NSAID class than oral diclofenac alone, and the addition of topical diclofenac to oral diclofenac did not cause an elevation of liver transaminases in osteoarthritis patients over use of oral diclofenac alone. Users may be apprised of the above information according to the invention. A further unexpected discovery of the study, the results for which are provided as Example 1, is that in the study the topical diclofenac solution was applied to only one knee.

Most patients suffer from osteoarthritis equally in both knees, yet single knee application yielded a clinical benefit in both knees. Users or prescribers may be further apprised of this additional information according to the invention.

Topical diclofenac in a DMSO vehicle is an effective treatment option for osteoarthritis of the knee with efficacy similar to, but tolerability better than, oral diclofenac. DMSO vehicle was no more efficacious than placebo. According to the invention, users may be apprised of this information with regard to use of topical diclofenac, particularly with regard to the use of a topical diclofenac solution comprising 1.5% w/w diclofenac sodium and 45.5% w/w DMSO, which also optionally contains propylene glycol, alcohol, glycerin and purified water as inactive ingredients.

Examples 2 and 3 describe the results of environmental toxin studies. Surprisingly in light of the efficacy of DMSO in facilitating the skin penetration of diclofenac, these studies show that concomitant, repeated use of a topical diclofenac solution containing 1.5% diclofenac sodium (2-[(2,6-dichlorophenyl)amino]benzeneacetic acid, monosodium salt), 45.5% DMSO, ethanol, propylene glycol, glycerine, and water, with other topical products, including DEET (active ingredient in insect repellent), 2,4-D (active ingredient in commonly used pesticides) and oxybenzone (active ingredient in sunscreens), did not enhance the systemic absorption of these products. According to the invention, users may be apprised of this information with regard to use of topical diclofenac, particularly with regard to the use of a topical diclofenac solution containing 1.5% diclofenac sodium (2-[(2,6-dichlorophenyl)amino]benzeneacetic acid, monosodium salt), 45.5% DMSO, ethanol, propylene glycol, glycerine, and water.

Example 4 describes the results of a transepidermal water loss ("TEWL") study performed on human volunteers' skin. TEWL is a parameter useful for measuring changes to stratum corneum barrier function. Unexpectedly given the role of DMSO in permeabilizing the skin for diclofenac uptake, the results show no alteration in skin barrier function following chronic use of topical diclofenac. According to the invention, users may be apprised of this information with regard to use of topical diclofenac, particularly with regard to the use of a topical diclofenac solution comprising 1.5% w/w diclofenac sodium and 45.5% w/w DMSO, which also optionally contains propylene glycol, alcohol, glycerin and purified water as inactive ingredients. Users may also be informed that, before applying sunscreen, insect repellant, lotion, moisturizer, cosmetics, or other topical medication to the same skin surface, for example, a knee, that has been treated with topical diclofenac, the user should wait until the treated area is dry, which occurs most often within 10 minutes.

Example 5 describes the results of a study to evaluate the ophthalmologic effects of topically applied DMSO in a 52-week non-occluded dermal toxicity study in Göttingen minipigs. It provides information about the ocular safety profile of dermally applied formulations containing purified DMSO. Results showed that there was no increased risk for development of lens opacities or changes in refractive indices associated with DMSO. In fact no test article-related ophthalmoscopic abnormalities were detected during the study.

Example 6 describes the results of a study to evaluate the toxicity of test articles containing 9, 45.5, and 90% w/w DMSO after dermal administration for 26 weeks, three times per day, and to evaluate reversibility of any observed changes following a 12-week postdose observation period in male and female Sprague-Dawley rats. No test article-related ophthalmological abnormalities were detected in any animal during the pretest, terminal, and recovery ophthalmoscopic examinations.

Examples 7 and 8 describe studies to evaluate the pharmacokinetics of diclofenac sodium, dimethyl sulfoxide (DMSO) and dimethyl sulfone (the major metabolite of DMSO) after a single- and multiple-dose applications of a topical diclofenac preparation containing 1.5% diclofenac sodium (2-[(2,6-dichlorophenyl)amino]benzeneacetic acid, monosodium salt), 45.5% DMSO, ethanol, propylene glycol, glycerine, and water. These data provide compelling evidence that the systemic exposure to diclofenac caused by use of the topical diclofenac to treat osteoarthritis of the knee (40 drops per knee QID) is much lower than that caused by a typical oral dose of diclofenac used in treatment of osteoarthritis (e.g., 50 mg three times per day or "TID"). The fact that the topical diclofenac can be shown to be comparable to oral diclofenac sodium for treatment of osteoarthritis (see Example 1) is very surprising in view of these facts, especially as it is widely believed that NSAIDs, such as diclofenac, exert their analgesic effects both locally and centrally. From the data in Example 8 it also can be computed that $C_{max}$ of orally administered diclofenac is more than one hundred fold higher than $C_{max}$ for the topical diclofenac.

Example 9 describes a study to assess the drying time of a topical diclofenac solution containing 1.5% diclofenac sodium, 45.5% DMSO, ethanol, propylene glycol, glycerine, and water when applied topically to the skin surface of the knee following a single dose application, from which it can be concluded that the mean drying time for the topical diclofenac solution following a single dose application was approximately 15 minutes, with considerable variability among subjects and dryness occurring as early as 10 minutes in most subjects. A 30 minute drying time prior to the application of other topicals is considered safe. The results of the study further indicate that it is appropriate to instruct a user that a patient using a topical diclofenac solution should wait at least 30 minutes after putting the topical diclofenac solution on the knee(s) before, for example, taking a shower or bath or otherwise wetting the knee(s).

Example 10 describes a study comparing the elimination constant after single and multiple dose application of a topical solution containing 1.5% diclofenac sodium and 45.5% DMSO.

Example 11 describes a multi-dose, comparative, exposure study under maximum use conditions per labeling of both Pennsaid® Topical Solution (Diclofenac Sodium topical solution 1.5% w/w and 45.5% w/w DMSO) and Solaraze® Gel (Diclofenac Sodium 3%).

In one nonlimiting embodiment, the user is provided with information in the form of (or substantially in the form of) the Attachment. In another nonlimiting embodiment, the information in the Attachment is provided in a form that has been modified where appropriate to refer to the subject product as a topical diclofenac gel or other formulation rather than a topical solution. In another nonlimiting embodiment, the user is provided with information comprising or consisting essentially of in the Attachment. In another nonlimiting embodiment, the user is provided with information consisting essentially of the Attachment.

Many embodiments are suitable for treatment of subjects either as a preventive measure (e.g., to avoid pain) or as a therapeutic composition to treat subjects who are suffering from acute or chronic pain. In one nonlimiting embodiment, for example, a method of treatment or prevention of pain, including pain associated with an arthritic condition, and related kits and articles of manufacture, comprises using a topical diclofenac solution or topical gel formulation described herein together with some or all of the clinical and/or preclinical information described herein. Arthritic conditions include the various forms of arthritis, including rheumatoid arthritis, osteoarthritis, and ankylosing spondylitis.

Disclosed herein are topical diclofenac formulations, kits, and methods of using topical diclofenac and topical diclofenac formulations. Specifically disclosed are methods of using topical diclofenac and informing the user of certain information as provided herein. With the knowledge of the particular information, the administration of topical diclofenac to the patient can be optimized to provide safer and more effective use of topical diclofenac, alone or together with oral diclofenac. As used herein, topical diclofenac formulations include topical diclofenac solutions and topical diclofenac gel formulations, including a topical diclofenac preparation containing 1.5% diclofenac sodium (2-[(2,6-dichlorophenyl)amino]benzeneacetic acid, monosodium salt), 45.5% DMSO, ethanol, propylene glycol, glycerine, and water.

Topical diclofenac therapy can be considered optimal when combined with the new clinical, preclinical, adverse event information provided and described herein. Disclosed herein are methods of using topical diclofenac for transdermal administration, which may provide an increase in the safety or efficacy of topical diclofenac treatment. Extensive research has been performed on administering topical diclofenac that now reveal several developments relating to improvements in safe and effective treatment using topical diclofenac. In certain preferred embodiments, the topical diclofenac for transdermal administration is in the form of a solution or a gel.

In one nonlimiting embodiment, such nonlimiting information provided to a user includes the information described in Example 1, or a summary thereof.

In another nonlimiting embodiment, such nonlimiting information provided to a user includes the information described in Examples 2 and/or 3, or a summary thereof.

In another nonlimiting embodiment, such nonlimiting information provided to a user includes the information described in Example 4, or a summary thereof.

In another nonlimiting embodiment, such nonlimiting information provided to a user includes the information described in Example 5, or a summary thereof.

In another nonlimiting embodiment, such nonlimiting information provided to a user includes the information described in Example 6, or a summary thereof.

In another nonlimiting embodiment, such nonlimiting information provided to a user includes the information described in Examples 7 and/or 8, or a summary thereof.

In another nonlimiting embodiment, such nonlimiting information provided to a user includes the information described in Example 9, or a summary thereof.

In another nonlimiting embodiment, such nonlimiting information provided to a user includes the information described in Example 10, or a summary thereof.

In another nonlimiting embodiment, such nonlimiting information provided to a user includes the information described in Example 11, or a summary thereof.

In another nonlimiting embodiment, such nonlimiting information provided to a user includes the information described in two or more or all of Examples 1-6. In another nonlimiting embodiment, such nonlimiting information provided to a user includes the information described in two or more or all of Examples 1-8. In another nonlimiting embodiment, such nonlimiting information provided to a user includes the information described in two or more or all of Examples 1-11.

In yet another nonlimiting embodiment, such nonlimiting information provided to a user is the information in the Attachment.

In one embodiment, such nonlimiting information provided to a user is or comprises the information in one or more or all of Sections 6 ("Adverse Reactions"), 7.8 ("Oral Non-steroidal Anti-inflammatory Drugs"), 7.9 ("Topical Treatments"), 12.3 ("Pharmacokinetics), 13.2 ("Animal Toxicology and/or Pharmacology") and 14 ("Clinical Studies") of the Attachment.

Topical diclofenac can be formulated for administration where the formulation generally contains DMSO and one or more pharmaceutically acceptable excipients. As used herein, "pharmaceutically acceptable excipient" means any other component added to the pharmaceutical formulation other than the diclofenac and the DMSO. Excipients may be added to facilitate manufacture, enhance stability, control release, enhance product characteristics, enhance bioavailability, enhance patient acceptability, etc. Pharmaceutical excipients include, for example, carriers, fillers, binders, disintegrants, lubricants, glidants, colors, preservatives, suspending agents, dispersing agents, film formers, buffer agents, pH adjusters, preservatives etc.

In certain embodiments, the diclofenac is in the form of a pharmaceutically acceptable salt or free acid. Examples of pharmaceutically acceptable salts include metal salts, including alkali metal, alkaline earth metal, and nitrogen-based salts, such as ammonium salts. Sodium, potassium, epolamine and diethylamine salts are preferred. In one preferred embodiment the diclofenac is diclofenac monosodium salt.

In one nonlimiting embodiment, the topical diclofenac is a solution.

In another nonlimiting embodiment, the topical diclofenac is a gel.

In one embodiment, the topical diclofenac is 1.5% w/w diclofenac sodium in a vehicle solution containing DMSO 45.5% w/w and other excipients. In one aspect of this embodiment, the other excipients comprise propylene glycol, alcohol, glycerin and purified water.

In one nonlimiting embodiment, the topical diclofenac is a gel formulation according to PCT/US2007/081674 (International Publication No. WO 2008/049020 A2), the contents of which are incorporated herein in their entirety by this reference. The topical diclofenac may be any of the gel formulations described or claimed therein. In another nonlimiting embodiment, the topical diclofenac is a gel formulation according to US Patent Application No. 20080300311 (published Dec. 4, 2008), the contents of which are incorporated herein in their entirety by this reference. The topical diclofenac may be any of the gel formulations described or claimed therein.

In another nonlimiting embodiment, the topical diclofenac is a gel formulation comprising diclofenac sodium, dimethyl sulfoxide, ethanol, propylene glycol, one or more thickening agents, and water. In one aspect of this embodiment, the topical diclofenac gel formulation further comprises glycerol. In another aspect, the thickening agent is selected from the group consisting of cellulose polymers, carbomer polymers, a carbomer derivative, a cellulose derivative, polyvinyl alcohol, poloxamers, polysaccharides, and mixtures thereof.

In another nonlimiting embodiment, the topical diclofenac is a gel formulation comprising or consisting essentially of 1-5% w/w diclofenac sodium; 30-60% w/w dimethyl sulfoxide; 1-50% w/w ethanol; 1-15% w/w propylene glycol; a thickener; and water (added to make 100% w/w). In a preferred aspect of this embodiment, the gel formulation has a viscosity of 10-50,000 centipoise.

In another nonlimiting embodiment, the topical diclofenac is a gel formulation comprising or consisting essentially of about 2% w/w diclofenac sodium; about 45.5% w/w dimethyl sulfoxide; about 23-29% w/w ethanol; about 11% w/w propylene glycol; about 0-6% w/w hydroxypropylcellulose (HY119); and water (added to make 100% w/w). In a preferred aspect of this embodiment, the gel formulation has a viscosity of 500-5,000 centipoise.

In another nonlimiting embodiment, the topical diclofenac is a gel formulation comprising or consisting essentially of diclofenac sodium at a concentration selected from the group consisting of 1, 1.5, 2 and 3% w/w; dimethyl sulfoxide at a concentration selected from the group consisting of 42, 43, 44, 45, 45.5 46, 47, 48 and 49% w/w and fractions in between; ethanol at 23-29% w/w; propylene glycol at a concentration selected from the group consisting of 9, 10, 11, 12, 13% w/w and fractions in between; hydroxypropylcellulose (HY119) at 0-6% w/w; and water (included in an amount sufficient to make 100% w/w). In a preferred aspect of this embodiment, the gel formulation has a viscosity of about 500-5000 centipoise.

In certain embodiments, the above-described topical diclofenac gel formulations include 1-5% glycerol. In such embodiments, the gel formulation will have a drying rate and a transdermal flux that are greater than a comparative liquid topical diclofenac formulation. In other embodiments, the above-described topical diclofenac gel formulations will have a pH of about 6.0 to about 10.0.

In another nonlimiting embodiment, the topical diclofenac is a gel formulation comprising diclofenac sodium, ethanol, DMSO, propylene glycol, hydroxypropylcellulose and water. In one aspect of this embodiment, the hydroxypropylcellulose is substituted with alklycellulose, hydroxyalkylcellulose, carboxyalkylcellulose, or sodium carboxyalklycellulose, where alkyl is methyl, ethyl or propyl, or a mixture thereof. In a further aspect of this embodiment, the said alklycellulose, hydroxyalkylcellulose, carboxyalkylcellulose, or sodium carboxyalklycellulose is replaced in whole or in part by an acrylic polymer (for example, Carbopol polymers, Noveon polycarbophils and Pemulen polymeric emulsifiers available commercially from Noveon Inc. of Cleveland, Ohio), an acrylic polymer derivative, a cellulose polymer derivative, polyvinyl alcohol ("PVA"), polyvinylpyrrolidone ("PVP"), a poloxamer, a polysaccharide, or a mixture thereof.

In another aspect, gel formulations useful in the invention are NSAID gel formulations, such as a topical diclofenac gel formulation, and components of the formulations are as follows: The gel formulations comprise an active agent, preferably a non-steroidal anti-inflammatory drug or pharmaceutically acceptable salts thereof. More preferably, the non-steroidal anti-inflammatory is diclofenac in the form of a pharmaceutically acceptable salt or free acid. Examples of pharmaceutically acceptable salts include metal salts, including alkali metal, alkaline earth metal, and nitrogen-based salts, such as ammonium salts. Sodium, potassium, epolamine and diethylamine salts are preferred. In one preferred embodiment the diclofenac is diclofenac monosodium salt.

In a preferred embodiment, the sodium salt of diclofenac is used. Diclofenac may be present in a range of approximately 0.1% to 10%, such as 1, 2, 3, 4, or 5% w/w. In another embodiment, the present invention includes a penetration enhancer. The penetration enhancer may be dimethyl sulfoxide ("DMSO") or derivatives thereof. The DMSO may be present in an amount by weight of 1% to 70%, and more preferably, between 25% and 60%, such as 25, 30, 40, 45, 50, 55, or 60% w/w. Preferably, DMSO is used in the present invention at a concentration of about 40 to about 50% w/w, such as 41, 42, 43, 44, 45, 46, 47, 48, 49 and 50% and all fractions in between such as 44, 44.5, 45, 45.5, 46, 46.5%, and the like. In certain embodiments, the gel formulation includes a lower alkanol, such as methanol, ethanol, propanol, butanol or mixtures thereof. In certain embodiments, the alkanol is present at about 1 to about 50% w/w. Preferably, ethanol is used at about 1-50% w/w, such as 1, 5, 10, 15, 20, 25, 30, 35, 40, 45, or 50% w/w, and all fractions in between. In certain embodiments, the gel formulation includes a polyhydric alcohol, such as a glycol. Suitable glycols include ethylene glycol, propylene glycol, butylene glycol, dipropylene glycol, hexanetriol and a combination thereof. Preferably, propylene glycol is used at about at 1-15% w/w, such as 1, 2, 3, 4, 5, 6, 7, 8, 9, 10, 11, 12, 13, 14, or 15% w/w, and all fractions in between. In certain embodiments, the gel formulation includes glycerol (also referred to as glycerine) at a concentration of 0-12% w/w. Preferably, glycerol is used at 0-4% w/w, such as 0, 1, 2, 3, or 4% w/w, and all fractions in between. In some embodiments, no glycerol is used in the formulation. In a preferred embodiment, the gel formulation provides a diclofenac solution and at least one thickening agent to make a gel. The at least one thickening agent of the present invention may be an acrylic polymer (for example, Carbopol polymers, Noveon polycarbophils and Pemulen polymeric emulsifiers available commercially from Noveon Inc. of Cleveland, Ohio), an acrylic polymer derivative, a cellulose polymer, a cellulose polymer derivative, polyvinyl alcohol, poloxamers, polysaccharides or mixtures thereof. Preferably the at least one thickening agent is hydroxypropylcellulose (HPC) used such that the end viscosity is between 10 and 50000 centipoise (cps). More preferably the end viscosity is between 500 and 20000 cps. The gel formulation may optionally include at least one antioxidant and/or one chelating agent. Preferred antioxidants may be selected from the group consisting of butylated hydroxytoluene (BHT), butylated hydroxyanisole (BHA), ascorbyl linoleate, ascorbyl dipalmitate, ascorbyl tocopherol maleate, calcium ascorbate, carotenoids, kojic acid, thioglycolic acid, tocopherol, tocopherol acetate, tocophereth-5, tocophereth-12, tocophereth-18, tocophereth-80, and mixtures thereof. Preferred chelating agents may be selected from the group consisting of ethylenediamine tetraacetic acid (EDTA), diammonium EDTA, dipotassium EDTA, calcium disodium EDTA, HEDTA, TEA-EDTA, tetrasodium EDTA, tripotassium EDTA, trisodium phosphate, diammonium citrate, galactaric acid, galacturonic acid, gluconic acid, glucuronic acid, humic acid, cyclodextrin, potassium citrate, potassium ethylenediaminetetramethylenephosphonic acid ("EDTMP"), sodium citrate, sodium EDTMP, and mixtures thereof. In addition, the topical gel formulations can also comprise a pH adjusting agent. In one particular embodiment, the pH adjusting agent is a base. Suitable pH adjusting bases include bicarbonates, carbonates, and hydroxides such as alkali or alkaline earth metal hydroxide as well as transition metal hydroxides. Alternatively, the pH adjusting agent can also be an acid, an acid salt, or mixtures thereof. Further, the pH adjusting agent can also be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like. The pH adjusting agent is present in an amount sufficient to adjust the pH of the composition to between about pH 4.0 to about 10.0, more preferably about pH 7.0 to about 9.5. In certain embodiments, the unadjusted pH of the admixed components is between 8 and 10, such as 9, without the need for the addition of any pH adjusting agents.

The present invention includes a method for applying multiple topical agents to a subject with pain comprising topically administering a pharmaceutical composition comprising a therapeutically effective amount of a topical diclofenac in DMSO, waiting for the treated area to dry (the time of which can be dependent on individual skin characteristics, environmental conditions such as temperature and humidity, and surface area, often about 5-30 minutes, about 5-20 minutes, for example, and typically about 10 minutes or less for a topical diclofenac preparation, including a topical diclofenac solution as described in the Examples), and applying another topical agents. In one nonlimiting embodiment, the subject has osteoarthritis. In another nonlimiting embodiment, the subject has osteoarthritis of the knee. In one embodiment, the topical agent administered after the topical diclofenac is a sunscreen or an insect repellant. In another nonlimiting embodiment, the invention includes a method of protecting a subject with osteoarthritis from UV exposure and alleviating the signs and symptoms of osteoarthritis in the subject comprising the steps of applying a therapeutically effective amount of a topical diclofenac in DMSO; waiting for the treated area to dry (the time of which can be dependent on individual skin characteristics, environmental conditions such as temperature and humidity, and surface area, often about 5-30 minutes, about 5-20 minutes, for example, and typically about 10 minutes or less for a topical diclofenac preparation, including a topical diclofenac solution as described in the Examples), applying sunscreen to the same area of treatment.

Also included herein are pharmaceutical products (kits) useful, for example, for the treatment or prevention of pain, including pain caused by arthritis, such as osteoarthritis, for example, which comprise one or more containers containing a topical diclofenac formulation and information or published material, e.g., as product inserts or product labels. The information can indicate quantities of the components to be administered, guidelines for administration, safety issues, and the like, all as disclosed and provided herein.

The kits may further comprise one or more conventional pharmaceutical kit components, such as, for example, one or more containers to aid in facilitating compliance with a particular dosage regimen, etc. Exemplary kits can be in the form of a package. Suitable packages and packaging are known in the art or easily ascertained by one of ordinary skill in the art.

In one nonlimiting embodiment, the topical diclofenac formulation is packaged with information informing the user that the topical diclofenac solution will not cause an uptake of one or more environmental toxins. In another nonlimiting embodiment, the topical diclofenac formulation is packaged with information that includes reference to a lack of anticipated or expected adverse events or adverse reactions in patients from exposure to one or more environmental toxins following the acute and/or chronic use of a topical diclofenac solution, for example a topical diclofenac preparation containing 1.5% diclofenac sodium (2-[(2,6-dichlorophenyl)amino]benzeneacetic acid, monosodium salt), 45.5% DMSO, ethanol, propylene glycol, glycerine, and water.

In one nonlimiting embodiment, a method of manufacturing a topical diclofenac pharmaceutical product comprises packaging a topical diclofenac dosage form with the Information. Additional information can include the information disclosed, summarized or otherwise provided herein, including the information provided in any of Examples 1-4.

In another nonlimiting embodiment, an article of manufacture comprises a container containing a dosage form of topical diclofenac, wherein the container is associated with published material informing the user of some of all of the Information. Additional information can include the information disclosed, summarized or otherwise provided herein, including the information provided in any of Examples 1-4.

In one nonlimiting embodiment of the methods and articles of manufacture provided herein, a topical diclofenac dosage form can comprise about 40 drops per knee, QID. In one aspect of this embodiment, a diclofenac oral dosage form may also be provided or recommended or included within the methods and articles of manufacture provided herein. In another nonlimiting embodiment of the methods and articles of manufacture provided herein, a topical diclofenac dosage form can comprise application of a topical diclofenac gel formulation twice daily.

In another nonlimiting embodiment of the methods and articles of manufacture provided herein, a kit of information concerning a topical diclofenac product comprising diclofenac and dimethyl sulfoxide is prepared and/or provided, said kit comprising information about (a) clinical effects of dosing of a topical diclofenac solution comprising 1.5% w/w diclofenac sodium and 45.5% w/w dimethyl sulfoxide, including (i) the effects of 40-drop QID dosing of said topical diclofenac solution; (ii) the effects of 40-drop QID dosing of said topical diclofenac solution in one or more clinical trials; (iii) results from a 12-week, double-blind, controlled trial of said topical diclofenac solution in subjects with osteoarthritis of the knee which compared the performance of said topical diclofenac solution against a vehicle solution containing 45.5% dimethyl sulfoxide and a placebo solution containing 2.3% dimethyl sulfoxide; and (iv) pharmacokinetic results from one or more studies in which single and multiple doses of a topical diclofenac in a solution containing dimethyl sulfoxide was applied topically to healthy human volunteers; (b) an adverse event profile for a topical diclofenac solution comprising 1.5% w/w diclofenac sodium and 45.5% w/w dimethyl sulfoxide, including, (i) concomitant use of oral NSAIDs with topical diclofenac resulted in a higher rate of rectal hemorrhage, more frequent abnormal creatinine, urea and hemoglobin; (ii) that in a controlled trial, a higher rate of contact dermatitis with vesicles was observed after treatment of 152 subjects with the combination of topical diclofenac and oral diclofenac; and (iii) results of a clinical study demonstrating that the addition of said topical diclofenac solution to oral diclofenac did not cause an elevation of liver transaminases over use of oral diclofenac alone; (c) preclinical study results for a topical formulation comprising dimethyl sulfoxide, including for example, the results of an animal study in which no adverse ocular effects were observed after multiple-daily dermal application to rats for 26 weeks and minipigs for 52 weeks of DMSO at twice the concentration found in a topical diclofenac solution (e.g., Pennsaid®); and (d) a statement that, once dry, sunscreen, insect repellant, lotion, moisturizer, cosmetics, and/or other topical products can be applied to an area previously treated with a topical diclofenac solution (e.g., Pennsaid®).

Yet another nonlimiting embodiment is a method of obtaining marketing authorization from a regulatory authority for a topical diclofenac product comprising referencing the kit of information.

In another embodiment, a method for distribution of a topical diclofenac product is provided, comprising the steps of (a) obtaining marketing authorization from a regulatory authority for a topical diclofenac product comprising referencing said kit of the invention; and providing said topical diclofenac product to one or more distributors.

The following examples further illustrate the invention but, of course, are not to be construed as in any way limiting its scope.

EXAMPLES

Example 1

12-Week, Double-Blind, Double-Dummy, Randomized Controlled Trial of Topical Diclofenac Solution This Example describes novel clinical information that may, for example, be provided to a user according to the present invention, comprising safety and efficacy results from a 12-week, double-blind, double-dummy, randomized controlled trial of a topical diclofenac preparation containing 1.5% diclofenac sodium (2-[(2,6-dichlorophenyl)amino] benzeneacetic acid, monosodium salt), 45.5% DMSO, ethanol, propylene glycol, glycerine, and water ("Topical Diclofenac Solution") in 775 subjects with radiologically confirmed, symptomatic primary osteoarthritis of the knee. The study included a placebo arm to establish efficacy, a DMSO vehicle arm to address possible DMSO efficacy, an oral diclofenac arm for comparison with the topical diclofenac solution, and a combination of Topical Diclofenac Solution plus oral diclofenac to assess combined treatment.

Study Subjects:

This randomized, double-blind, double-dummy, placebo-, vehicle- and active-controlled study was conducted at 40 outpatient centers in Canada and 21 centers in the United States following approval by the appropriate institutional review boards. Eligible subjects, after written informed consent, included men and non-pregnant women aged 40-85 with primary OA of the knee based on (i) standard radiological criteria for OA (Altman, R D, et al., *Atlas of individual radiographic features in osteoarthritis. Osteoarthritis Cartilage* 1995; 3 (Suppl A):3-70) on a recent (within 3 months) examination, (ii) pain, with regular use of an NSAID or other analgesic medication (at least 3 days a week for the previous month) and (iii) a flare of pain and minimum Likert pain score of 8 (40 on a scale normalized to 0-100; see below, Efficacy Measures) at baseline, following washout of that medication. A flare was defined as an increase in total Likert pain score of 25% and at least 2, and a score of at least moderate on one or more of the five items/questions of the WOMAC LK3.1 pain subscale (Bellamy, N, et al., Validation study of WOMAC: a health status instrument for measuring clinically important patient relevant outcomes to antirheumatic drug therapy in patients with osteoarthritis of the hip or knee. *J Rheumatol.* 1988 December; 15(12):1833-40). All knee films were reviewed by a single radiologist and each compartment was scored (none=1, mild=2, moderate=3, severe=4). Only one knee was treated; where both knees met all entry criteria, the more painful knee (or dominant knee if they scored the same) was selected. Standard exclusion criteria were employed, as described in Roth S H, Shainhouse J Z. Efficacy and safety of a topical diclofenac solution (Pennsaid®) in the treatment of primary osteoarthritis of the knee: a randomized, double-blind, vehicle-controlled clinical trial. *Arch Intern Med.* 2004; 164:2017-23.

Study Design:

Eligible subjects were stratified by the investigator at baseline into stratum 1 (no pain and normal radiological examination in the non-study knee) or stratum 2 (pain and/or abnormal radiological examination in the non-study knee), and then randomized into the trial by receiving the next numbered study kit at that clinic for that stratum. Each study kit contained topical solution and oral tablets for one of the five treatment regimens: (i) Topical Diclofenac Solution [Pennsaid® Topical Solution, Nuvo Research Inc., Mississauga, Canada] plus oral placebo tablets, (ii) 'DMSO vehicle'; vehicle solution plus oral placebo tablets (vehicle solution was the complete carrier, including 45.5% DMSO and other excipients, with no diclofenac), (iii) 'placebo'; placebo solution plus oral placebo tablets (placebo solution was a modified vehicle solution with only 2.3% DMSO, for blinding purposes, and no diclofenac), (iv) 'oral diclofenac'; placebo solution plus oral diclofenac tablets (100 mg slow release), or (v) 'topical diclofenac+oral diclofenac'; Topical Diclofenac Solution plus oral diclofenac tablets. Subjects applied 40 drops of solution (approximately 1.2 mL) around the entire circumference of the study knee, without massage, 4 times daily, and took one study tablet daily for up to 12 weeks.

Concomitant analgesic and anti-inflammatory medications, including over the counter NSAIDs and other analgesics, were prohibited. Continuation of stable treatment with glucosamine, chondroitin, anti-depressants or a proton pump inhibitor (previous 90 days), or low-dose (≤325 mg/day) acetylsalicylic acid (previous 30 days) was permitted. Acetaminophen was provided, and permitted (up to four 325-mg caplets per day) except during the 3 days before each efficacy assessment. Other topical products on the knee, including skin emollients, were prohibited. A patient with a gastrointestinal adverse event was allowed to start a proton pump inhibitor. Compliance with the treatment regimen was assessed by weighing the solution bottles and counting study tablets at each clinic visit.

All study solutions appeared as identical clear, colorless liquids. It was expected that some subjects applying Topical Diclofenac Solution or DMSO vehicle would report a garlic taste or odor from exhaling dimethyl sulfide, a volatile DMSO metabolite; therefore, a token amount of DMSO (2.3%) was included in the placebo solution. Previous trials with topical diclofenac confirmed the success of this blinding procedure as the incidence of 'taste perversion' adverse events was no different with placebo solution from topical diclofenac. Oral diclofenac and placebo tablets appeared identical (Novopharm® Inc.). Each study kit was assembled according to a computer-generated randomization schedule created by an external statistician for each stratum using a block size of 5. The randomization sequence was concealed from investigators, subjects and the sponsor's clinical research personnel until after data lock.

Efficacy Measures:

Each subject completed a full efficacy assessment questionnaire after randomization at baseline and at 4, 8 and 12 weeks, or at drop out. The co-primary efficacy variables (Bookman A A, et al., Effect of a topical diclofenac solution for relieving symptoms of primary osteoarthritis of the knee: a randomized controlled trial. *CMAJ.* 2004; 171:333-8) were defined a priori as WOMAC pain and physical function, measured by the 5-point Likert scale (Biswal S, et al., Longterm efficacy of topical nonsteroidal anti-inflammatory drugs in knee osteoarthritis: metaanalysis of randomized placebo controlled clinical trials. *J Rheumatol.* 2006; 33:1841-4), and patient overall health assessment ("POHA"). The POHA asked the question, "Considering all the ways your osteoarthritic (study) knee and its treatment affect you, including both positive and negative effects, how would you rate your overall state of health in the past 48 hours?" Secondary efficacy variables were WOMAC stiffness and patient global assessment ("PGA") of knee osteoarthritis. The PGA asked the question, "How has the osteoarthritis in your study joint been over the last 48 hours?" The POHA and PGA were scored on a 5-point Likert scale. There was no assessment of the non-treated knee. Safety Measures: At all visits, vital signs were measured, dermatological evaluation of the study knee was done according to a standard numerical (0-4) scale (Shirley H H, et al. Efficacy and safety of a tropical diclofenac solution (Pennsaid®) in the treatment of primary osteoarthritis of the knee: a randomized, double-blind, vehicle-controlled clinical trial. *Arch. Intern. Med.* 2004; 164:2017-23) and adverse events were solicited using open-ended questions. Adverse events were categorized according to Coding Symbols for Thesaurus of Adverse Reaction Terms ("COSTART"). Blood and urine samples were obtained for routine laboratory analysis at baseline, 4 and 12 weeks. Ocular examination (visual acuity test, slit lamp examination and lens assessment) was conducted at the baseline and final visit.

Statistical Analysis Plan:

All planned analyses were specified a priori. Analysis of the Likert efficacy data was by modified intent to treat ("mITT"), excluding only those subjects who had no baseline data or did not administer at least one dose of both study solution and tablets. Statistical tests were two-sided at the 5% level of significance. All efficacy analyses were by analysis of covariance of the change in score from baseline to landmark final assessment, with baseline score as the covariate. Subjects in both randomization strata were combined for all analyses.

The primary efficacy comparison was topical diclofenac vs. placebo for the primary efficacy variables, with no correction for analysis of multiple primary variables (regulatory design required superiority for each primary variable). The sample size required to show the superiority of topical diclofenac over placebo was 142 subjects per arm, based on an estimate from previous trials of the difference (standard deviation) between groups for the change in score of 1.5 (4.5) for pain, 5.0 (15) for physical function and 0.4 (1.2) for PGA, power of 80% and Type I error rate of $\alpha=0.05_{2\text{-}tailed}$ (Baer P A, et al., Treatment of osteoarthritis of the knee with a topical diclofenac solution: a randomised controlled, 6-week trial [ISRCTN53366886]. *BMC Musculoskelet Disord.* 2005; 6:44; Bookman A A, et al., Effect of a topical diclofenac solution for relieving symptoms of primary osteoarthritis of the knee: a randomized controlled trial. *CMAJ.* 2004; 171: 333-8; Roth S H, Shainhouse J Z. Efficacy and safety of a Topical Diclofenac Solution (Pennsaid®) in the treatment of primary osteoarthritis of the knee: a randomized, double-blind, vehicle-controlled clinical trial. *Arch Intern Med.* 2004; 164:2017-23).

A post hoc sensitivity analysis of the primary efficacy data was performed by imputing no improvement (i.e., baseline score carried forward and imputed as final score ("BOCF") to non-completers by reason of an adverse event or lack of effect and for subjects excluded from mITT.

Secondary comparisons included topical diclofenac vs. placebo for the secondary variables, and topical diclofenac vs. DMSO vehicle and DMSO vehicle vs. placebo for all variables. A post hoc efficacy analysis compared topical diclofenac vs. oral diclofenac and topical diclofenac+oral diclofenac vs. oral diclofenac. For a missing final score, last observation was carried forward ("LOCF"). Safety analyses were performed on all subjects who received even one dose of either study medication. There was no imputation of missing safety data. Results were as follows.

Study Subjects:

Of 1396 subjects screened, 775 were randomized to one of the 5 treatment arms and 527 subjects completed treatment. Over 95% of patients had bilateral disease (pain or abnormal radiological examination also in non-study knee) with pain in the contralateral knee in 90%. A total of 88% of subjects met the modified (Hochberg M C, et al., Guidelines for the Medical Management of Osteoarthritis Part II. Osteoarthritis of the Knee. *Arthritis & Rheumatism* 1995; 38(1):1541-1546) American College of Rheumatology (ACR) criteria (Altman R, et al., Development of criteria for the classification and reporting of osteoarthritis: classification of osteoarthritis of the knee. *Arthritis Rheum.* 1986; 29:1039-1049) for osteoarthritis, pain and osteophytes, and the remaining had pain with either joint space narrowing or subchondral sclerosis. Subjects in each treatment arm had similar demographic and baseline characteristics, duration of exposure and compliance (>89% of expected use for topical solution and oral tablets). Withdrawals for an adverse event were similar among treatment groups. Withdrawals for lack of effect were similar among topical diclofenac, placebo and DMSO vehicle arms, but fewer with the oral diclofenac arms.

There were 772 subjects included in the mITT group. Excluded were 3 subjects who did not take at least one dose of both topical and oral medication, or had no data. Individual subjects who omitted baseline assessment for a specific efficacy variable were excluded from that analysis.

Efficacy:

The primary efficacy analyses, as shown in the below Table 2 ("Efficacy Variable Scores"), show the superiority of topical diclofenac over placebo for the three co-primary variables—pain (P=0.015), physical function (P=0.034), and POHA (P<0.0001). Superiority was observed also for the secondary variable PGA (P=0.016), but not for stiffness. There was greater improvement with topical diclofenac (P<0.05) compared to DMSO vehicle for all five variables (Table 2). A post-hoc BOCF sensitivity analysis of the primary efficacy data of all 775 patients did not change any of the conclusions of superiority of topical diclofenac compared with placebo (pain, P=0.031; physical function, P=0.041; POHA, P=0.0001).

TABLE 2

Efficacy variable scores[a]

| | TDiclo[b] | placebo[b] | DMSO[b] | ODiclo[b] | TDiclo + ODiclo[b] | P value TDiclo vs. placebo | TDiclo vs. DMSO | TDiclo vs. ODiclo |
|---|---|---|---|---|---|---|---|---|
| WOMAC Pain | (n = 154) | (n = 155) | (n = 161) | (n = 151) | (n = 151) | | | |
| Baseline score | 13.2 | 12.9 | 13.0 | 13.2 | 13.2 | | | |
| | (3.4) | (3.3) | (3.2) | (3.0) | (3.4) | | | |
| Change in score[c] | −6.0 | −4.7 | −4.7 | −6.4 | −7.0 | 0.015 | 0.009 | 0.429 |
| | (4.5) | (4.4) | (4.3) | (4.1) | (4.8) | | | |

TABLE 2-continued

Efficacy variable scores[a]

| | TDiclo[b] | placebo[b] | DMSO[b] | ODiclo[b] | TDiclo + ODiclo[b] | P value TDiclo vs. placebo | P value TDiclo vs. DMSO | P value TDiclo vs. ODiclo |
|---|---|---|---|---|---|---|---|---|
| WOMAC Physical Function | (n = 154) | (n = 153) | (n = 161) | (n = 151) | (n = 150) | | | |
| Baseline score | 41.7 (12.8) | 41.6 (11.7) | 41.4 (11.4) | 42.1 (12.0) | 41.0 (11.2) | | | |
| Change in score[c] | −15.8 (15.1) | −12.3 (14.7) | −12.1 (14.6) | −17.5 (14.3) | −18.7 (14.0) | 0.034 | 0.026 | 0.319 |
| POHA | (n = 154) | (n = 152) | (n = 160) | (n = 150) | (n = 148) | | | |
| Baseline | 2.34 (1.02) | 2.22 (1.03) | 2.30 (1.14) | 2.23 (1.12) | 2.19 (1.04) | | | |
| Change in score[c] | −0.95 (1.30) | −0.37 (1.04) | −0.65 (1.12) | −0.88 (1.31) | −0.95 (1.21) | <0.0001 | 0.016 | 0.956 |
| PGA | (n = 154) | (n = 153) | (n = 161) | (n = 151) | (n = 150) | | | |
| Baseline | 3.12 (0.78) | 3.04 (0.82) | 3.13 (0.74) | 3.04 (0.87) | 3.08 (0.81) | | | |
| Change in score[c] | −1.36 (1.19) | −1.01 (1.18) | −1.07 (1.10) | −1.42 (1.29) | −1.53 (1.27) | 0.016 | 0.018 | 0.439 |
| WOMAC Stiffness | (n = 154) | (n = 153) | (n = 161) | (n = 151) | (n = 150) | | | |
| Baseline | 5.14 (1.63) | 5.01 (1.70) | 5.12 (1.61) | 5.21 (1.72) | 5.07 (1.53) | | | |
| Change in score[c] | −1.93 (2.01) | −1.52 (2.05) | −1.48 (2.07) | −2.07 (2.02) | −2.30 (2.00) | 0.112 | 0.035 | 0.596 |

Abbreviations:
TDiclo, Topical Diclofenac Solution plus oral placebo;
placebo, topical placebo plus oral placebo;
DMSO, topical dimethyl sulfoxide-containing vehicle plus oral placebo;
ODiclo, oral diclofenac plus topical placebo;
TDiclo + ODiclo, Topical Diclofenac Solution plus oral diclofenac;
WOMAC, Western Ontario McMaster Universities LK3.1 Osteoarthritis Index;
POHA, patient overall health assessment;
PGA, patient global assessment of the study knee
[a]Data are presented as mean (SD). Maximum score for pain, 20; physical function, 68; POHA and PGA, 4; stiffness, 8.
[b]The number of subjects (n) varied by efficacy parameter because individual subjects did not submit a full baseline assessment.
[c]Final score minus baseline score Additionally, the Efficacy Variable Score shows that no significant efficacy advantage of the DMSO vehicle over placebo was observed for the primary or secondary variables, except for the POHA. Furthermore, a comparison of oral diclofenac vs. topical diclofenac found no statistical difference for any of the 5 efficacy variables. The combination of topical diclofenac+oral diclofenac was no better than oral diclofenac alone for all variables (pain, P=0.30; physical function, P=0.33; POHA, P=0.43; stiffness, P=0.16; PGA, P=0.50).

Mean [SD] acetaminophen use with topical diclofenac (0.64 [0.83] caplets per day) was lower than with placebo (0.95 [1.14], P=0.005) and DMSO vehicle (0.99 [1.11], P=0.002), and was not different than that for oral diclofenac (0.55 [0.82], P=0.41) or topical diclofenac+oral diclofenac (0.46 [0.70]; P=0.10).

Safety:

Skin adverse events predominated with topical diclofenac, most being dry skin. The overall incidence of skin adverse events was similar in topical diclofenac+oral diclofenac, and lower in placebo, and oral diclofenac arms. The rate with DMSO vehicle was intermediate between topical diclofenac and placebo. Only 5 (3.2%) subjects in topical diclofenac withdrew due to an application site reaction. Importantly, as shown in the below Table 3 ("Incidence of Adverse Events") the incidence of adverse events of the digestive system with topical diclofenac was no greater than placebo and much lower than oral diclofenac and topical diclofenac+oral diclofenac. Withdrawal due to a digestive system adverse event was higher in oral diclofenac (11 [7.3%]) vs. topical diclofenac (4 [2.6%]) and placebo (3 [1.9%]). Additionally, as shown in the below Table 3, the combination topical diclofenac+oral diclofenac did not increase the incidence of digestive system events over oral diclofenac alone.

TABLE 3

Incidence of adverse events[a]

| Adverse Event | TDiclo (n = 154) | placebo (n = 157) | DMSO (n = 161) | ODiclo (n = 151) | TDiclo + ODiclo (n = 152) |
|---|---|---|---|---|---|
| Any adverse event | 96 (62.3) | 90 (57.3) | 97 (60.2) | 94 (62.3) | 98 (64.5) |
| Abnormal taste sensation or odor | 0 (0.0) | 1 (0.6) | 1 (0.6) | 0 (0.0) | 1 (0.7) |
| Any digestive system event | 10 (6.5) | 15 (9.6) | 18 (11.2) | 36 (23.8) | 39 (25.7) |
| Abdominal pain | 5 (3.2) | 1 (0.6) | 5 (3.1) | 11 (7.3) | 3 (2.0) |

TABLE 3-continued

Incidence of adverse events[a]

| Adverse Event | TDiclo (n = 154) | placebo (n = 157) | DMSO (n = 161) | ODiclo (n = 151) | TDiclo + ODiclo (n = 152) |
|---|---|---|---|---|---|
| Dyspepsia | 4 (2.6) | 6 (3.8) | 6 (3.7) | 6 (4.0) | 5 (3.3) |
| Diarrhea | 2 (1.3) | 3 (1.9) | 2 (1.2) | 7 (4.6) | 12 (7.9) |
| Liver function tests abnormal | 3 (1.9) | 1 (0.6) | 6 (3.7) | 12 (7.9) | 11 (7.2) |
| Rectal hemorrhage | 1 (0.6) | 0 (0.0) | 0 (0.0) | 0 (0.0) | 5 (3.3) |
| Nausea | 0 (0.0) | 0 (0.0) | 1 (0.6) | 3 (2.0) | 5 (3.3) |
| Any skin/appendages event | 41 (26.6) | 12 (7.6) | 27 (16.8) | 11 (7.3) | 47 (30.9) |
| Dry skin (application site) | 28 (18.2) | 5 (3.2) | 18 (11.2) | 4 (2.6) | 30 (19.7) |
| Contact dermatitis (application site) | 4 (2.6) | 1 (0.6) | 5 (3.1) | 1 (0.7) | 12 (7.9) |
| Rash | 4 (2.6) | 0 (0.0) | 2 (1.2) | 0 (0.0) | 0 (0.0) |
| Contact dermatitis with vesicles (application site) | 3 (1.9) | 0 (0.0) | 0 (0.0) | 1 (0.7) | 6 (3.9) |
| Pruritis (application site) | 2 (1.3) | 0 (0.0) | 0 (0.0) | 0 (0.0) | 1 (0.7) |
| Other system event[b] | | | | | |
| Headache | 27 (17.5) | 18 (11.5) | 21 (13.0) | 26 (17.2) | 21 (13.8) |
| Back pain | 15 (9.7) | 10 (6.4) | 15 (9.3) | 11 (7.3) | 4 (2.6) |
| Arthralgia | 14 (9.1) | 15 (9.6) | 25 (15.5) | 12 (7.9) | 7 (4.6) |
| Pain | 7 (4.5) | 5 (3.2) | 11 (6.8) | 8 (5.3) | 1 (0.7) |
| Respiratory disorder | 5 (3.2) | 6 (3.8) | 4 (2.5) | 8 (5.3) | 7 (4.6) |
| Accidental injury | 4 (2.6) | 6 (3.8) | 7 (4.3) | 4 (2.6) | 6 (3.9) |
| Abnormal vision | 4 (2.6) | 5 (3.2) | 4 (2.5) | 4 (2.6) | 1 (0.7) |
| Conjunctivitis | 4 (2.6) | 1 (0.6) | 0 (0.0) | 3 (2.0) | 0 (0.0) |

Abbreviations:
TDiclo, Topical Diclofenac Solution plus oral placebo;
placebo, topical placebo plus oral placebo;
DMSO, topical dimethyl sulfoxide-containing vehicle plus oral placebo;
ODiclo, oral diclofenac plus topical placebo;
TDiclo + ODiclo, Topical Diclofenac Solution plus oral diclofenac
[a]Data are presented as number (%) of subjects.
[b]Other adverse events with incidence ≥2% in the TDiclo group No difference between treatment groups was observed for cardiovascular events, which were <2% in each treatment group. The incidence of hypertension was similar for all groups (1.3% for Topical Diclofenac Solution, oral diclofenac and Topical Diclofenac Solution+oral diclofenac; 1.2% for DMSO vehicle; 0.6% for placebo). There was no difference among the groups in reports of an abnormal taste sensation or odor, confirming the success of the blinding procedure for DMSO.

There was no serious adverse event in the Topical Diclofenac Solution arm, 4 in placebo (1 anemia, 1 cerebrovascular accident, 1 fractured hip, 1 dislocated prosthetic hip), 1 in DMSO vehicle (acute enteritis), 1 in oral diclofenac (post-polypectomy lower gastrointestinal bleed, 8 days after withdrawal of study medication) and 3 in topical diclofenac+ oral diclofenac (1 leg cellulitis, 1 unstable angina, 1 transient ischemic attack).

Changes in key NSAID-related laboratory parameters are shown in the below Table 4 ("Analysis of Change in Laboratory Parameters").

TABLE 4

Analysis of change[a] in laboratory parameters

| AST | TDiclo (n = 145) | placebo (n = 142) | DMSO (n = 150) | ODiclo (n = 138) | TDiclo + ODiclo (n = 141) |
|---|---|---|---|---|---|
| Mean change, U/L | −0.9 (10.3) | −0.6 (5.2) | 0.2 (8.5) | 2.5 (10.9) | 4.1 (29.6) |
| Normal to abnormal[b], N (%) | 10 (6.9) | 5 (3.5) | 8 (5.3) | 27 (19.6) | 20 (14.2) |
| ALT | | | | | |
| Mean change, U/L | −1.0 (11.7) | −0.3 (9.9) | −0.6 (9.8) | 7.2 (25.3) | 8.2 (68.9) |
| Normal to abnormal, N (%) | 6 (4.1) | 4 (2.8) | 2 (1.3) | 26 (18.8) | 24 (17.0) |
| Hemoglobin | | | | | |
| Mean change, g/L | −1.7 (6.2) | −0.8 (6.2) | −0.4 (6.5) | −3.8 (7.1) | −4.8 (6.8) |
| Normal to abnormal, N (%) | 3 (2.1) | 7 (4.9) | 5 (3.3) | 8 (5.8) | 18 (12.6) |
| Creatinine | | | | | |
| Mean change, µmol/L | −0.4 (10.5) | 0.8 (9.0) | 0.3 (10.3) | 3.1 (11.0) | 4.4 (11.2) |
| Normal to abnormal, N (%) | 4 (2.8) | 8 (5.6) | 6 (4.0) | 10 (7.2) | 15 (10.6) |

TABLE 4-continued

Analysis of change[a] in laboratory parameters

| AST | TDiclo (n = 145) | placebo (n = 142) | DMSO (n = 150) | ODiclo (n = 138) | TDiclo + ODiclo (n = 141) |
|---|---|---|---|---|---|
| Creatinine Clearance[c] | | | | | |
| Mean change, mL/min | 0.4 (10.3) | −0.5 (8.6) | −0.5 (8.3) | −2.4 (8.7) | −3.3 (9.7) |
| Normal to abnormal, N (%) | 11 (7.6) | 8 (5.7) | 9 (6.0) | 10 (7.2) | 16 (11.4) |

Abbreviations:
TDiclo, Topical Diclofenac Solution plus oral placebo;
placebo, topical placebo plus oral placebo;
DMSO, topical dimethyl sulfoxide-containing vehicle plus oral placebo;
ODiclo, oral diclofenac plus topical placebo;
TDiclo + ODiclo, Topical Diclofenac Solution plus oral diclofenac;
ALT, alanine aminotransferase;
AST, aspartate aminotransferase.
[a]Mean (SD) unless otherwise indicated. Only subjects with both a baseline and final lab value for the parameter are shown.
[b]Change from normal at baseline to above upper limit of normal for AST, ALT, creatinine, or below lower limit of normal for hemoglobin, creatinine clearance.
[c]Calculated as per Cockcroft DW and Gault MW, Prediction of creatinine clearance from serum creatinine, *Nephron* 1976; 16: 31-41.

Overall, the mean change in the laboratory value and the number of subjects developing an abnormality showed no difference between topical diclofenac and placebo or DMSO vehicle, but a greater mean change and higher incidence of abnormality occurred with the oral diclofenac arms. With oral diclofenac compared with topical diclofenac, there was a greater mean change in hemoglobin, alanine aminotransferase, gamma-glutamyl transpeptidase, creatinine and creatinine clearance, and a greater number of subjects developing an abnormality for these parameters. With respect to the transaminases ALT (alanine aminotransferase) and AST (aspartate aminotransferase), there was no statistically significant change in mean values between the oral diclofenac and oral plus topical diclofenac treatment arms. Development of abnormal laboratory parameters was generally below clinically relevant levels. No subject developed a clinically significant change in hemoglobin or creatinine. An increase in any liver enzyme to three times the upper limit of normal occurred in 1 subject with placebo, 1 with DMSO vehicle, 2 with oral diclofenac and 3 with topical diclofenac+oral diclofenac, but none with topical diclofenac.

Ocular examination at baseline and final revealed no change in visual acuity (data not shown) and no difference in the development of lens abnormality (cataract) with placebo (4 [2.6%] subjects) vs. topical diclofenac (2 [1.3%]) or DMSO vehicle (6 [3.8%]).

Conclusions:

The results of this clinical study clearly show the effectiveness of Topical Diclofenac Solution applied topically to treat the symptoms of osteoarthritis of the knee.

Topical Diclofenac Solution was superior to both topical comparator groups (placebo and DMSO vehicle) for all 3 primary efficacy variables, pain, function and patient overall health. Efficacy was confirmed by a conservative BOCF sensitivity analysis.

The WOMAC physical function questionnaire asks patients to score physical function in areas such as difficulty descending stairs, difficulty ascending stairs, difficulty rising from sitting, difficulty standing and difficulty walking on a flat surface. The superiority of topical diclofenac solution over placebo was surprising given that (i) the physical functions measured in the WOMAC physical function questionnaire are generally accomplished with the use of both knees, (ii) only one knee was treated in the study, (iii) 95% of patients had disease in both knees (with pain in the contralateral knee occurring in 90% of the study population) and (iv) the blood levels of diclofenac produced by the topical diclofenac solution when treating one knee are far below the levels achieved by oral administration of the drug and regarded as necessary to achieve a systemic effect (see Examples 7 and 8 below). Remarkably, there was no statistical difference between topical diclofenac solution treatment of one knee and oral diclofenac (which would provide treatment for both knees) for the physical function efficacy variable.

This study followed a typical 12-week oral NSAID trial design, namely, primary osteoarthritis of the knee with pain and abnormal radiological findings. Although most subjects had bilateral osteoarthritis, only one painful knee was treated with topical solution. Inasmuch as outcome measures of physical function and overall patient health assessment are likely to be negatively influenced by symptoms in the non-treated knee, this trial design biased against Topical Diclofenac Solution. In any oral NSAID trial, and in this study's oral diclofenac arms, subjects automatically treat both knees, avoiding these factors. The inclusion of oral therapy for all groups added a second placebo effect to the topical comparator arms, imposing a yet higher burden to prove efficacy of Topical Diclofenac Solution over placebo. Despite these elements in trial design the efficacy of Topical Diclofenac Solution was robustly established.

The response of patients in the oral diclofenac group in this study (40-48% improvement in variable score) was the same as seen in other oral NSAID trials (Bellamy N, Buchanan W W et al., A multicenter study of tenoxicam and diclofenac in patients with osteoarthritis of the knee. *J Rheum.* 1993; 20:999-1004; Yocum D, et al., Safety and efficacy of meloxicam in the treatment of osteoarthritis. *Arch Int Med.* 2000; 160:2947-54), providing a powerful external audit on the validity of the trial design and conduct, and further confirmation of the sustained efficacy of Topical Diclofenac Solution. Topical Diclofenac Solution was found to be as effective as oral diclofenac at relieving the symptoms of knee osteoarthritis with less NSAID-related systemic toxicity than oral diclofenac. These observations support the safety and efficacy results of a previous equivalence study of Topical Diclofenac Solution vs. oral diclofenac.

Claims of therapeutic efficacy for DMSO itself in osteoarthritis were discounted in an earlier, 4-week trial with topical diclofenac (Bookman A A, et al., Effect of a topical diclofenac solution for relieving symptoms of primary osteoarthritis of the knee: a randomized controlled trial. *CMAJ.* 2004; 171: 333-8) and are further disproven by this 12-week study.

There was no apparent difference between Topical Diclofenac Solution and placebo in NSAID-associated gastrointestinal adverse events (the incidence was actually lower with Topical Diclofenac Solution). In this study, no eye lens abnormalities were observed with DMSO-vehicle or Topical Diclofenac Solution treatment. The combination Topical Diclofenac Solution+oral diclofenac showed no increase in adverse events relative to Topical Diclofenac Solution or oral diclofenac alone. The blood level of diclofenac following topical application as Topical Diclofenac Solution is only about 12 ng/mL and the incremental increase with the combination would be negligible compared with the predicted level of 1500 ng/mL that is reported with oral diclofenac. Although combined treatment with Topical Diclofenac Solution+oral diclofenac did not provide a statistical advantage over oral diclofenac alone, this regimen could be a reasonable treatment paradigm in an individual with persistent or breakthrough knee pain despite using an oral NSAID.

In conclusion, this Example shows that Topical Diclofenac Solution provides durable improvement in the symptoms of osteoarthritis of the knee, and that relief is not contributed by the DMSO-carrier. Efficacy of Topical Diclofenac Solution was comparable to that achieved with oral diclofenac. For the patient initiating pharmacological therapy for relief of symptoms associated with osteoarthritis of the knee based on current treatment guidelines, Topical Diclofenac Solution is a viable, evidence-based treatment option.

Example 2

Influence of a Topical Diclofenac Solution on Percutaneous Absorption of Three Different Environmental Toxins after Repeated Epicutaneous Administration to Minipigs This Example describes novel preclinical information that may, for example, be provided to a user according to the present invention, which relates to the influence of a topical diclofenac solution containing 1.5% diclofenac sodium (2-[(2,6-dichlorophenyl)amino]benzeneacetic acid, monosodium salt), 45.5% DMSO, ethanol, propylene glycol, glycerine, and water ("Topical Diclofenac Solution") on the percutaneous absorption of three different environmental toxins, as evaluated in a study involving repeated epicutaneous administration to minipigs.

The Test Item was Topical Diclofenac Solution [Pennsaid® Topical Solution, Nuvo Research Inc., Mississauga, Canada]. The environmental toxins selected for use in the study were oxybenzone (in the form of Equaline SPF 23 faces sunscreen; active compound 6% oxybenzone), DEET, i.e., N,N-diethyl-m-toluamide (in the form of Deep woods OFF!® pump spray; active compound 25% N,N-diethyl-m-toluamide), and 2,4-D, i.e., 2,4-D, dimethylamine salt (in the form of Spectracide Weed Stop 2X For Lawns Concentrate; active compound 7.57% 2,4-D, dimethylamine salt). The control items used in the study were Retin-A 0.1% (tretinoin) cream, Men's Rogaine® Extra Strength Topical Solution (minoxidil 5% w/v), both of which are approved and marketed in the United States. Both control products have skin permeation enhancing capabilities and were selected for comparison to the Topical Diclofenac Solution in the enhancement of environmental toxins. Retin-A (tretinoin) stimulates mitotic activity and increased turnover of follicular epithelial cells, resulting in disruption of the skin barrier function with consequent enhancement of transepidermal water loss. Compromising skin barrier function can cause enhancement in permeation of molecules through the skin. The skin permeation enhancement of Rogaine is associated with its high content of propylene glycol (50%), a known skin permeation enhancer.

Methods:

In this study, performed according to Good Laboratory Practices ("GLP"), 18 female Göttingen Minipigs, a commonly used non-rodent species for pharmacokinetic studies, were selected for entry into the study based on the results of a satisfactory preliminary health screening. There were six treatment groups with 3 female animals per group. Animals were allocated employing a pseudo-random body weight stratification procedure that yielded groups with approximately equal mean body weight.

The Test Item and the controls were supplied ready-to-use. Toxin No. 1 (sunscreen) was applied undiluted. Toxins Nos. 2 (DEET) and 3 (2,4-D) were diluted in ethanol and water, respectively, before use on test day 1 according to the below dilution scheme. The same toxin administration solutions were used on test day 1, 21, 28 and 35. Between the administrations, the solutions were stored at +2° C. to +4° C.

Preparation of the Toxin Administration Dose

| Toxin No. | Active compound | Strength of active cmpd in the toxin (w/v) | Targeted exposure of active cmpd to 150 cm² [µg] | Dilution of the toxin | Volume of diluted toxin to be applied to 150 cm² [mL] |
|---|---|---|---|---|---|
| 1 | oxybenzone | 6% | 300000 | 1 | 5 |
| 2 | DEET | 25% | 6723 | 40 | 1.08 |
| 3 | 2,4-D | 7.57% | 13.35 | 5000 | 0.88 |

Toxin was applied by epicutaneous administration via syringe onto the back region. There was a single administration on test day 1 (before administration of the Test Item or the Controls) and single administration on days 21, 28 and 35 (after administration of the Test Item or the Controls). The administration area was 150 cm²/animal. The administration site was situated on the animal's back between the fore and the hind extremities. The surface area of the application site was selected to provide a high toxin exposure that would ensure measurable systemic levels of the toxins.

Prior to the start of the study, the administration sites were cleared of bristles, if present. The remaining hairs were clipped. The toxin was spread onto the administration area using a syringe. The administration area was not covered with any dressing. Following administration the animals were restrained for at least 1 hour (until the toxin had completely dried) in slings which allowed free movement of the head but prevented a complete body turn in order to prevent access by the animals to the toxins.

The six treatment groups were assigned to receive toxins, Test Items and Controls as set forth in the following table.

| Group | Toxin No. (Name) | Test Item/Control |
|---|---|---|
| 1 | 1 (oxybenzone) | Topical Diclofenac Solution (Test Item) |
| 2 | 2 (DEET) | Topical Diclofenac Solution (Test Item) |
| 3 | 3 (2,4-D) | Topical Diclofenac Solution (Test Item) |
| 4 | 1 (oxybenzone) | Retin-A (Control no. 1) |
| 5 | 2 (DEET) | Rogaine ® (Control no. 2) |
| 6 | 3 (2,4-D) | Rogaine ® (Control no. 2) |

On test day 21, Topical Diclofenac Solution (Test Item) or Rogaine Topical Solution (Control No. 2), respectively, was applied 30 minutes before toxin administration based on a pre-specified schedule. No administration of Retin-A (Control No. 1) was scheduled for test day 21. On test day 21 the toxin administration was carried out after the Test Item/Control administration according to the following schedule: Groups 1, 2 and 3: 30 minutes after Test Item/Control administration; Group 4: after an overnight break; Groups 5 and 6: 30 minutes after Test Item/Control administration.

In sum, Test Item/Control application was as follows: Topical Diclofenac Solution (Test Item), 0.22 mL/administration site four times daily from test days 6 to 20 (7:30, 12:30, 17:30, 22:30) and one single dose on day 21 (7:30); Retin-A 0.1% cream (Control No. 1), 112.5 mg/administration site once daily from test days 6 to 20 (22:30); Rogaine ES (Control No. 2), 0.8 mL/administration site twice daily from test days 6 to 20 (7:30, 17:30) and one single dose on day 21 (7:30). The administration site of the Test Item or Controls was exactly the same as for the toxins, i.e. 150 cm$^2$ on the animal's back between the fore and hind extremities, as noted above. Toxin dose levels were selected based upon available human environmental and occupational exposure data. Dose levels for the Test Item or Controls were based on the recommended doses of the products in humans.

The Test Item or Control was spread onto the administration area using a syringe. The administration area was not covered with any dressing. Following administration the animals were restrained for at least 1 hour (until the test item and controls had completely dried) in slings which allowed free movement of the head but prevented a complete body turn in order to prevent access by the animals to the Test Item or Controls.

Any contact of the test areas with water was avoided throughout the whole experiment.

Observations:

Observations related to individual animals made throughout the study included clinical signs, body weight and food/water consumption.

For evaluation of local tolerance, skin reactions were examined once daily throughout the study, prior to each administration (end of the respective exposure period), if applicable. Reactions, namely, erythema, eschar and oedema formation were scored based on Draize J H, Appraisal of the Safety of Chemicals in Food, Drugs and Cosmetics, Association of Food and Drug Officials of the United States, Austin, Tex., 1959. Any other lesions were also recorded, if any occurred.

Blood sampling for pharmacokinetics was undertaken for each animal at predetermined sampling times and processed for at least 2 mL Li-Heparin plasma/sample, which were split into two aliquots of 1 mL each.

The area under the concentration-time curve ("AUC") from time zero to 48h, $AUC_{0-48h}$, for each toxin was calculated for each minipig after each toxin administration on test days 1, 21, 28 and 35 using a linear trapezoid method. Descriptive statistics (arithmetic mean, standard deviation) of non-transformed $AUC_{0-48h}$ and natural log-transformed $AUC_{0-48h}$ were calculated for each treatment group for the administration days on test days 1, 21, 28 and 35. Log-transformed $AUC_{0-48h}$ were compared using the repeated measurements employing a generalized linear model of variance using treatment group and administration day as covariates. The achievement of steady state of diclofenac was assessed by using repeated measurements employing analysis of variance ("ANOVA") with log-transformed trough concentrations on test days 19, 20 and 21. All statistical analyses were two-sided and in all analyses the Type I (alpha) error was fixed at the 5% level.

Results:

With regard to clinical signs, no signs of local intolerance reactions were observed in any of the minipigs after repeated epicutaneous administration of 0.22 mL Topical Diclefenac Solution/animal (approx. 3.5 mg diclofenac sodium/animal) and any of the Toxin Nos. 1, 2 or 3. Additionally, no signs of local intolerance reactions were observed in any of the minipigs after repeated epicutaneous administration of either Control No. 1 or Control No. 2.

Additionally, no signs of systemic intolerance reactions were observed in any of the minipigs after repeated epicutaneous administration of 0.22 mL Topical Diclofenac Solution/animal (approx. 3.5 mg diclofenac sodium/animal) and any of the three toxins. No signs of systemic intolerance reactions were observed in any of the minipigs after repeated epicutaneous administration of either 112.5 mg Retin-A 0.1% (tretinoin) cream/animal (control no. 1) or 0.8 mL Men's Rogaine® Extra Strength Topical Solution/animal (control no. 2) and any of the three toxins.

The body weight was in the normal range throughout the course of the study in all animals after repeated epicutaneous administration of 0.22 mL Topical Diclofenac Solution/animal (approx. 3.5 mg diclofenac sodium/animal) or the two controls and any of the three toxins.

No influence on the food consumption was noted for any of the animals after repeated epicutaneous administration of 0.22 mL Topical Diclofenac Solution/animal (approx. 3.5 mg diclofenac sodium/animal) or the two controls and any of the three toxins.

The visual appraisal of the drinking water consumption did not reveal any Test Item-related influence.

Pharmacokinetic data results indicated that systemic diclofenac steady state was reached by day 19.

Due to limitation in the sensitivity of the analytical methods employed in the study, no DEET (Toxin no. 2) or 2,4-D (Toxin no. 3) could be quantified in plasma for any of the animals treated with the Topical Diclofenac Solution or the Rogaine so no firm conclusions could be drawn from the study concerning the enhancement of systemic absorption of these toxins. A subsequent study (described in Example 3 below) using higher concentrations of DEET and 2,4-D was therefore conducted.

In contrast, the exposure to oxybenzone could be well quantified on all application days. The courses of the plasma concentrations of oxybenzone were summarized non-compartmentally by means of $C_{max}$ (maximum observed plasma concentration), tmax (time of $C_{max}$ after application of the toxin), and the $AUC_{0-48}$ (the trapezoidal area under the time course of the plasma concentrations up to 48 hours after application).

Based on the ANOVA of the log-transformed $AUC_{0-48}$, the area exposure to oxybenzone for the animals treated with Topical Diclofenac Solution was statistically significantly lower (p≤0.05) on days 21, 28 and 35 compared with the animals treated with the control (Retin-A), whereas there was no statistically significant difference between the treatments groups on day 1 (before the start of the treatments with the test and control items). No statistically significant differences were noted for the Topical Diclofenac Solution or control (Retin-A) treated animals of groups 1 and 4, respectively, for $C_{max}$ and AUC-values of test day 1 compared to test days 21, 28 and 35.

Conclusions:

Epicutaneous application of Topical Diclofenac Solution four times daily from test day 6 to 20 with a single dose applied on the morning of day 21, while resulting in relevant systemic exposure to diclofenac, did not induce relevant local or systemic untoward changes. Treatment with Topical Diclofenac Solution, however, did not amplify the exposure of oxybenzone, an epicutaneously applied toxin.

That systemic diclofenac steady state was reached by day 19 indicates that a maximum degree of skin permeabilization for diclofenac by the Topical Diclofenac Solution vehicle has been reached after 14 days of treatment with Topical Diclofenac Solution.

Results also showed that there was no quantifiable systemic absorption of DEET or 2,4-D at baseline (prior to treatment with Topical Diclofenac Solution or Rogaine) or following a 15-day pre-treatment with Topical Diclofenac Solution or Rogaine (Treatment Groups 2, 3, 5 and 6).

According to the results, systemic absorption of oxybenzone occurred prior to treatment with Topical Diclofenac Solution and Retin-A control (days 1-3) and this level thus represents baseline systemic absorption of oxybenzone. There was no significant difference in baseline oxybenzone systemic levels and systemic levels obtained following a 14 day pre-treatment period with Topical Diclofenac Solution and it is therefore concluded Topical Diclofenac Solution did not enhance the systemic absorption of oxybenzone. However, there was a significant difference in baseline oxybenzone systemic levels and systemic levels obtained following a 14 day pre-treatment period with Retin-A Control. Therefore, Retin-A enhances the systemic absorption of oxybenzone.

It can be concluded that a 15-day repeat dose treatment with Topical Diclofenac Solution, QID, while resulting in a maximum degree of skin permeabilization for diclofenac, does not enhance the systemic absorption of oxybenzone.

Example 3

Influence of a Topical Diclofenac Solution on Percutaneous Absorption of Two Different Environmental Toxins after Repeated Epicutaneous Administration to Minipigs This Example describes novel preclinical information that may, for example, be provided to a user according to the present invention, which relates to the influence of a topical diclofenac preparation containing 1.5% diclofenac sodium (2-[(2,6-dichlorophenyl)amino]benzeneacetic acid, monosodium salt), 45.5% DMSO, ethanol, propylene glycol, glycerine, and water ("Topical Diclofenac Solution") on the percutaneous absorption of two environmental toxins from Example 2, evaluated at higher doses in a study involving repeated epicutaneous administration to minipigs. In Example 2 the dose levels for the toxins were selected based on the available human environmental and occupational exposure data but the results did not provide systemic exposure above the limit of quantitation. Thus, to increase the potential systemic exposure of the toxin, the maximum dermal exposure to the toxin was selected for this study. As in Example 2, the Test Item was Topical Diclofenac Solution.

The two environmental toxins DEET, i.e., N,N-diethyl-m-toluamide (in the form of Deep woods OFF!® pump spray; active compound 25% N,N-diethyl-m-toluamide) and 2,4-D, i.e., 2,4-D, dimethylamine salt (in the form of Spectracide Weed Stop 2X For Lawns Concentrate; active compound 7.57% 2,4-D, dimethylamine salt). The single Control Item used in the study was Retin-A 0.1% (tretinoin) cream.

Methods:

The study was carried out as described in Example 2 using 12 minipigs (four groups of three female minipigs each). Animals of groups 1 and 2 were treated with the Test Item from the morning of day 6 until the morning of day 21; groups 3 and 4 were treated with Retin-A 0.1% (the Control Item) from the evening of day 6 until the evening of day 20.

Single doses of the toxins were administered on the morning of days 1, 21, 28, and 35. Groups no. 1 (Test Item) and 3 (Control Item) were investigated with Toxin no. 1 (DEET), whereas the animals of groups 2 (Test item) and 4 (Control Item) were investigated with Toxin no. 2 (2,4-D). The volume of the toxin formulation applied was 1 mL on day 1 and 1.5 mL on subsequent doses starting on day 21. In contrast to Example 2, the 1.5 mL toxin volume resulted in an administered dose of DEET (Toxin No. 1) of 375,000 µg and an administered dose of 2,4-D (Toxin No. 2) of 113,550 ng.

The Test Item, Control Item and Toxins were administered as follows. The Test Item was administered four times daily from test days 6 to 20 (7:30, 12:30, 17:30, 22:30); one single dose on day 21 (7:30). The Control Item was administered once daily from test days 6 to 20 (22:30). Toxin Nos. 1 and 2 were administered once on test day 1 (before administration of the Test Item or the Controls) and once on test days 21 (after administration of the Test Item), 28 and 35.

Results:

Exposure to DEET could be well-quantified on all application days. In the Topical Diclofenac Solution arm, the dose-normalized area exposure to DEET ($AUC_{0-48}$) on days 21, 28, and 35 was on average 1.18, 1.61, and 1.44 times higher than on day 1, respectively; but was not statistically significantly different. Under the Retin-A Control treatment, the dose normalized area exposure on these days was on average 1.56, 1.83, and 1.30 times higher than on day 1 and were statistically significantly different on test day 28.

Exposure to 2,4-D could be well-quantified on all application days. Under the Test treatment, the dose normalized area exposure to 2,4-D on days 21, 28, and 35 was on average 2.04, 1.27, and 1.16 times lower than on day 1, respectively, but was not statistically significantly different. Under the Control treatment, the dose normalized area exposure on these days was on average 10.84, 8.86, and 7.29 times higher than on day 1 and were statistically significantly different. Accordingly, there is a distinct amplification of the 2,4-D exposure in the control group (Retin-A), but not in the animals treated with the Test treatment (Topical Diclofenac Solution).

No signs of local intolerance reactions were observed for any of the minipigs after repeated epicutaneous administration of 0.22 mL Topical Diclofenac Solution/animal (approx. 3.5 mg diclofenac sodium/animal) and Toxin No. 1. Animal no. 4 (group 2) treated with 0.22 mL Topical Diclofenac Solution/animal (approx. 3.5 mg diclofenac sodium/animal) and Toxin No. 2 revealed a very slight to well defined erythema on test days 7 to 14. Animal nos. 7 and 8 (group 3) treated with 112.5 mg Retin-A 0.1% (tretinoin) cream/animal and Toxin No. 1 revealed a well defined erythema on test days 21 and 22 and a very slight to well defined erythema on test day 35. Animal no. 12 (group 4) treated with 112.5 mg Retin-A 0.1% (tretinoin) cream/animal and toxin no. 2 (group 4) revealed a moderate to severe erythema on test day 21 and a well defined erythema on test day 35.

No signs of systemic intolerance were noted for any of the minipigs after repeated epicutaneous administration of either 0.22 mL Topical Diclofenac Solution/animal (approx. 3.5 mg diclofenac sodium/animal) or the Control Item and the two toxins. Additionally, none of the animals died prematurely; the body weight was in the normal range in all animals throughout the course of the study; and no influence was noted on the food and drinking water consumption for any of the animals.

Epicutaneous application of Topical Diclofenac Solution four times daily from test day 6 to 20 with a single dose applied on the morning of day 21 resulted in relevant systemic exposure to diclofenac.

Conclusions:

Epicutaneous application of Topical Diclofenac Solution four times daily from test day 6 to 20 with a single dose applied on the morning of day 21, while resulting in relevant systemic exposure to diclofenac, did not induce relevant local or systemic untoward changes. The achievement of steady state levels of diclofenac by day 21 indicates that that a maximum degree of skin permeabilization for diclofenac had been reached. In contrast to Retin-A, treatment with Topical Diclofenac Solution did not amplify the toxic risk of epicutaneously applied toxins such as 2,4-D and DEET.

Example 4

Effect on Stratum Corneum Barrier Function of Multiple Doses of Topical Diclofenac Solution as Measured by Transepidermal Water-Loss This Example describes novel preclinical information that may, for example, be provided to a user according to the present invention, which comprise information regarding an assessment of the effect on stratum corneum barrier function, as measured by transepidermal water loss ("TEWL"), of multiple doses of a topical diclofenac preparation containing 1.5% diclofenac sodium (2-[(2,6-dichlorophenyl)amino] benzeneacetic acid, monosodium salt), 45.5% DMSO, ethanol, propylene glycol, glycerine, and water ("Topical Diclofenac Solution") compared with a positive control, Retin-A®, and an untreated site as a negative control.

Study Design:

The study was conducted as a four-period, open label, paired comparison in a single group. Period One (Baseline) was a period of one week prior to the first application on Day 1. At Period Two (Treatment), subjects applied test articles (Topical Diclofenac Solution or Retin-A®) for a period of six weeks. At Period Three (Recovery), subjects underwent a recovery period of two weeks following the treatment period. At Period Four (Retin-A® Challenge) subjects applied Retin-A® under occlusion to the same test site as during Period Two for a period of up to two weeks. Thus, the total study duration was approximately 12 weeks, with eight treatment weeks spread between Period Two (six-week treatment period) and Period Four (two-week treatment period).

Protocol:

At Period One (Baseline), baseline measurements of TEWL were performed on Days −7, −5, and −3 prior to the first application on Day 1. At Period Two (Treatment), subjects applied test articles for a period of six weeks. TEWL was measured on each of the test sites (4 cm×4 cm) immediately before application of the morning dose of test articles on Days 1, 3, 5, 8, 15, 22, 29, 36 and 43. Each subject applied one drop (approximately 30 μL) of Topical Diclofenac Solution to a test site on the right or left volar forearm (as randomized) four times a day for six weeks, at approximately 08:00, 13:00, 18:00 and 23:00 hours. The dose of Topical Diclofenac Solution utilized in this study (approximately 30 μL to a surface area of 16 $cm^2$) was calculated to approximate the Topical Diclofenac Solution dose that applied QID to the knee is shown in Example 1 to be effective for treatment of the pain and symptoms of knee osteoarthritis, namely 40 drops (approximately 1.2 mL) to a knee surface area of approximately 800 $cm^2$. Each subject applied a dab (about 12 mg) of Retin-A® to a separate test site on the opposite volar forearm once per day for six weeks, at approximately 08:00 hours. The subject used his/her finger to spread the test articles over their respective test sites. Each forearm had a test area that was left untreated as a negative control. The subjects allowed the test articles to dry before covering the test sites with clothing and avoided sunlight exposure to the test sites during the study. At Period Three (Recovery), subjects underwent a recovery period of two weeks following the treatment period. TEWL was measured on each of the test sites on the morning of Days 45, 47, 50, and 58. At Period Four (Retin-A® Challenge) on Days 58-71, Retin-A® was applied under occlusion to the same test site to which Retin-A® had been applied during Period Two. A designated member of the study staff applied two dabs (about 24 mg) of Retin-A® to the Retin-A® test site, once daily for 14 days, at approximately 08:00 hours. The Retin-A® test site was occluded using polyethylene film (Saran Wrap®) for 15 hours following each application. TEWL was measured on the Retin-A® site and the untreated control site of the same arm on the morning of Days 59-72.

TEWL:

TEWL analysis was carried out on the data of the intent-to-treat ("ITT") analysis group. The ITT analysis group included all enrolled subjects who received at least one dose of test article. TEWL was quantified using a VapoMeter, a closed chamber evaporimeter. Change in TEWL between the treated and untreated sites was monitored over time. Descriptive statistics (arithmetic mean, standard deviation, coefficient of variation, median, minimum, and maximum) for the TEWL data was summarized for each treatment. Individual and mean TEWL time profiles were plotted by treatment and period on a linear scale.

To assess the validity of the study to measure changes in TEWL, the post-treatment results for the positive control, Retin-A®, were compared to the untreated site on the same arm using repeated measures analysis of covariance ("ANCOVA") with the average pre-treatment TEWL measure as the covariate. During conduct of the study and preliminary review of the data, it appeared that the positive control was not causing skin irritation to the expected degree. In order to validate the study, a Retin-A® Challenge Period was added via a protocol amendment as described above, and the ANCOVA analysis was repeated for the Challenge Period using Day 58 TEWL measure as the baseline covariate. The TEWL response for the Topical Diclofenac Solution site during the Treatment Period was compared to the untreated site on the same arm using repeated measures ANCOVA with the average pre-treatment TEWL measure as the covariate. Secondary analyses included comparisons between Topical Diclofenac Solution and Retin-A® change in TEWL (difference from untreated site) for the Treatment Period, and correlation analyses between TEWL and the variables: skin irritation score, temperature and humidity.

Safety:

Safety was assessed through evaluation of the safety variables: adverse events, skin irritation score, laboratory analysis and vital signs. Safety analysis was carried out on the data of every subject who received at least one treatment with study article.

TEWL Results:

The results for treatment with Topical Diclofenac Solution indicate that it did not cause an increase in TEWL relative to the untreated site following 6 weeks of treatment at a dose, that applied QID to the knee, is shown in Example 1 to be effective for treatment of the pain and symptoms of knee osteoarthritis. No difference between Topical Diclofenac Solution and Retin-A® was noted during the Treatment Period (neither caused an increase in TEWL during this period of the study).

During the Challenge Period with Retin-A®, skin irritation was noted (see Safety Results) and a significant increase in TEWL relative to the untreated site was observed. These results for the Challenge Period validate the study design by showing that the subjects were responsive to this positive control, a known skin irritant.

Figure 2:
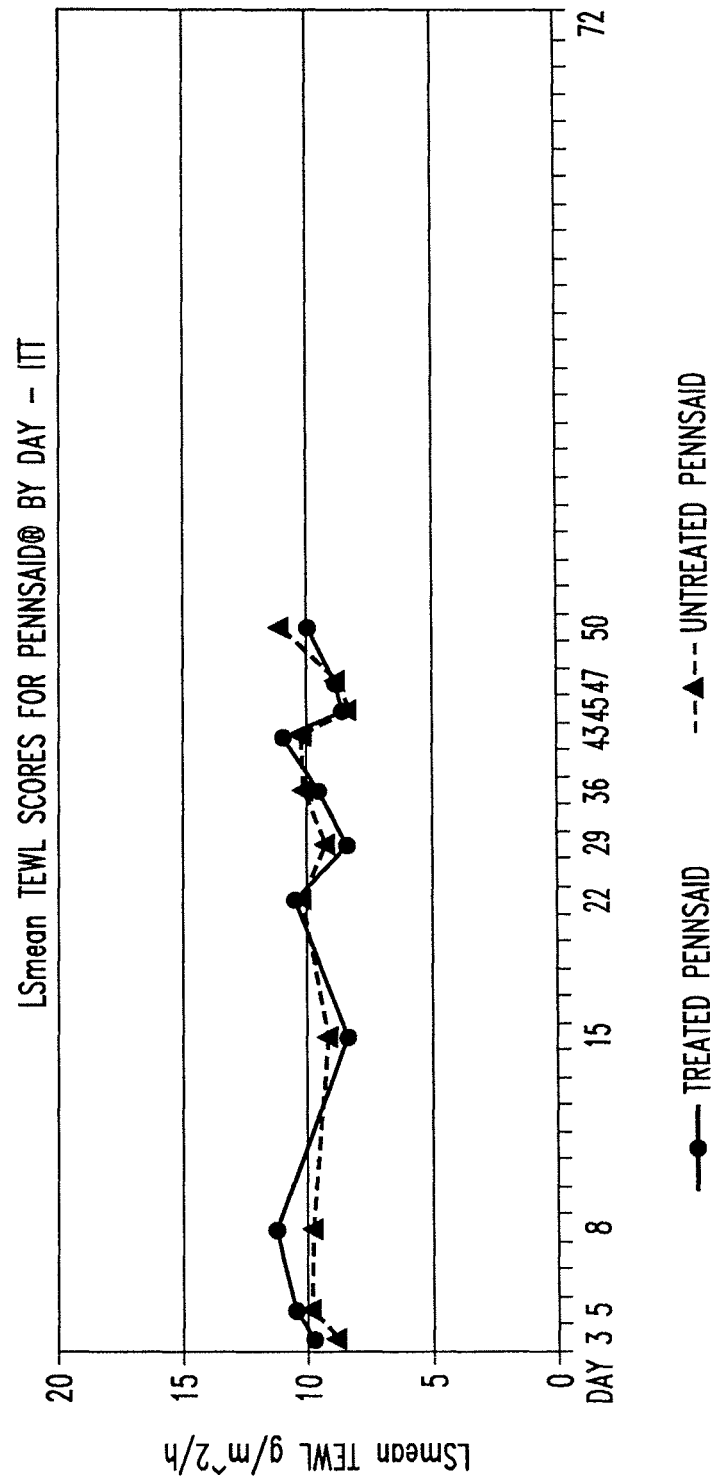
FIG. 2 shows mean TEWL Scores for Pennsaid® by Day-ITT.

Mean TEWL time profiles are shown in FIG. 1 (Retin-A®) and FIG. 2 (Topical Diclofenac Solution). Review of FIG. 1 shows an increase in TEWL for the Retin-A® treated site during the Challenge Period relative to the untreated site, and no difference between treated and untreated sites for Topical Diclofenac Solution and Retin-A® during the Treatment Period.

Safety Results:

There were a total of 51 adverse events reported by 12 subjects. The majority of adverse events were classified as mild in severity (35 events) and classified as probably related to the test article (32 events). The majority of the adverse events reported consisted of skin irritation responses (i.e. contact dermatitis, dry skin, pruritus). These were observed at the Retin-A® application test sites for all subjects except for one who reported the adverse event 'dry skin' that occurred at the Topical Diclofenac Solution treated test site.

The frequency of worst skin irritation score during the Treatment Period for Topical Diclofenac Solution revealed 14 of 15 subjects with a worst score of zero, indicating no skin irritation. One subject had a score of 0.5 (dryness or flaking) for the Topical Diclofenac Solution treated site. For Retin-A®, no skin irritation was observed during the Treatment and Recovery Periods. During the Challenge Period, 7 subjects had a worst score of 3 (erythema with induration and vesiculation) and one subject had a score of 1 (erythema) for the Retin-A® treated site. The occurrence of skin irritation for the Retin-A® sites was expected for this positive control.

Two subjects experienced changes in clinical laboratory evaluations (glucose, ALT and AST elevations) that were documented as adverse events. All three adverse events were considered mild and not related to the test articles.

There were no clinically significant findings related to blood pressure, pulse or respiration rates.

Conclusions:

The objective of this study was to evaluate the effect on stratum corneum barrier function, as measured by TEWL, of chronic application of Topical Diclofenac Solution as compared with a positive control, Retin-A®, and an untreated site as a negative control.

The dose of Topical Diclofenac Solution utilized in this study (approximately 30 µL to a surface area of 16 $cm^2$) was calculated to approximate that shown in Example 1 to be effective for treatment of the pain and symptoms of knee osteoarthritis when applied QID to the knee (40 drops (approximately 1.2 mL) to a knee surface area of approximately 800 $cm^2$). Following chronic dosing with Topical Diclofenac Solution for 6 weeks in this study, no significant increase in TEWL was observed. As measurement of TEWL has been shown to be a validated method for assessing skin barrier function (Fluhr J W, Feingold K R, Elias P M. Transepidermal water loss reflects permeability status: validation in human and rodent in vivo and ex vivo models. Exp Dermatol 2006; 15:483-492), these results indicate that Topical Diclofenac Solution did not alter the stratum corneum barrier function.

Treatment with Retin-A®, used as a positive control in this study, in the Challenge Period confirmed skin irritation following Retin-A® treatment and a resulting increase in TEWL, thus validating the study.

In conclusion, the results of this study demonstrate that following chronic dosing with Topical Diclofenac Solution, no significant increase in TEWL was observed, indicating that Topical Diclofenac Solution did not substantially alter the stratum corneum barrier function.

Example 5

Ophthalmologic Effects of Topically Applied DMSO in a 52-Week Non-Occluded Dermal Toxicity Study in Göttingen Minipigs This Example describes novel preclinical information that may, for example, be provided to a user according to the present invention, comprising the results of a study that was conducted on minipigs which provides information about the ocular safety profile of dermally applied formulations containing purified DMSO.

The broad aim of the study was to evaluate the potential dermal toxicity of DMSO when administered topically to four groups of Göttingen Minipigs® for 52 weeks at concentrations of 0, 9%, 45.5% and 90% (w/w) and to evaluate reversibility, progression, or delayed appearance of any observed changes following a 1-month postdose observation period. Two additional groups of Göttingen Minipigs® were dosed topically for 39 weeks at 0% and 90% followed by a 4-month recovery post dose observation period.

Four groups consisting of six animals/sex/group received DMSO at respective dose levels of 0, 9, 45.5, or 90% (w/w) by dermal application three times a day for 364 consecutive days. Following 52 weeks of administration, two animals/sex at 0, 9, 45.5, and 90% dose levels were maintained for a 4-week recovery period. Two additional groups consisting of six animals/sex/group received the control or 90% (w/w) DMSO by dermal application three times a day for 273 consecutive days. Following 39 weeks of administration, two animals/sex at 0 and 90% dose levels were maintained for a 4 month recovery period. The control or test article was administered to all groups at a dose volume of 4.5 mL/dose/application site (0.015 mL/$cm^2$; 300 $cm^2$ application site) until Week 20. Beginning Week 20 the control or test article was administered to all groups at a dose volume 5.6 mL/dose/application site (0.015 mL/$cm^2$; 375 $cm^2$ application site).

| Group Assignments | | | |
|---|---|---|---|
| Group Number | Dose Concentration (%) | Number of Animals | |
| | | Male | Female |
| 1[a] | 0 | 6 | 6 |
| 2[a] | 9 | 6 | 6 |
| 3[a] | 45.5 | 6 | 6 |
| 4[a] | 90 | 6 | 6 |
| 5[b] | 0 | 6 | 6 |
| 6[b] | 90 | 6 | 6 |

[a]Four animals/sex/group were necropsied after 52 weeks of administration. Two animals/sex/group remained on study for a 4-week recovery period.
[b]Four animals/sex/group were necropsied after 39 weeks of administration. Two animals/sex/group remained on study for a 4-month recovery period.

Compositions of the Control and Test Articles were as Follows

Control Vehicle

| | |
|---|---|
| Ethanol (95% v/v) | 11.79% w/w |
| Propylene Glycol | 11.20% w/w |
| Glycerin | 11.20% w/w |
| Purified Water | 65.81% w/w |

9% DMSO

| | |
|---|---|
| Ethanol (95% v/v) | 11.79% w/w |
| Propylene Glycol | 11.20% w/w |
| Glycerin | 11.20% w/w |

|  |  |
|---|---|
| DMSO | 9.00% w/w |
| Purified Water | 56.81% w/w |

45.5% DMSO

|  |  |
|---|---|
| Ethanol (95% v/v) | 11.79% w/w |
| Propylene Glycol | 11.20% w/w |
| Glycerin | 11.20% w/w |
| DMSO | 45.50% w/w |
| Purified Water | 20.31% w/w |

90% DMSO

|  |  |
|---|---|
| Ethanol (95% v/v) | 2.00% w/w |
| Propylene Glycol | 2.00% w/w |
| Glycerin | 2.00% w/w |
| DMSO | 90.00% w/w |
| Purified Water | 4.00% w/w |

Observations for morbidity, mortality, injury, and the availability of food and water were conducted twice daily for all animals. Clinical observations were conducted weekly. At the end of the each treatment and recovery period, necropsy examinations were performed, organ weights were recorded, and selected tissues were microscopically examined.

One female at 90% DMSO was euthanized in extremis on Day 151 of the study. The cause of the morbidity of this animal was determined to be respiratory distress and this was considered incidental to treatment and not test article-related. All remaining animals survived to their scheduled termination at the terminal necropsy at 39 or 52 weeks and the 4-week and 4-month recovery periods.

Ophthalmoscopic examinations were conducted pretest, and during Weeks 26, 39, and 52. Examinations were performed by a doctor of veterinary medicine with Diplomate, American College of Veterinary Ophthalmologists credentials.

Unexpectedly given the results of earlier studies on non-primate species, no increased risk for development of lens opacities or refractive index changes associated with DMSO were observed. In fact, no test article-related ophthalmoscopic abnormalities of any kind were detected during the study. One female in the control group (i.e. an animal that had not been exposed to DMSO) had a posterior cortical axial cataract with equatorial extrusion at the Week 39 ophthalmoscopic examination. One male at 45.5% DMSO, one male at 90% DMSO, and one control female had conjunctivitis in one or both eyes only at the pretest examination. No other abnormalities were detected in any male or female at any of the ophthalmoscopic examinations.

Example 6

Ophthalmologic Effects of DMSO in a 26-Week Dermal Toxicity Study in Sprague-Dawley Rats Followed by a 12-Week Recovery Period This Example describes novel preclinical information that may, for example, be provided to a user according to the present invention, comprising the results of a study conducted to evaluate the toxicity of test articles containing DMSO after dermal administration for 26 weeks, three times per day, and to evaluate reversibility of any observed changes following a 12-week post-dose observation period. Three treatment groups of 25 male and 25 female CD® [Crl:CD®(SD)] Sprague-Dawley rats were administered the test article, Dimethyl sulfoxide (DMSO), at respective dose concentrations of 9, 45.5, and 90% w/w. One additional group of 25 animals/sex served as the control and received the vehicle. Compositions of the test articles and control were identical to those used in Example 5 above. The vehicle or test article was administered to all groups epicutaneously, three times a day for 182 consecutive days, at a dose volume of 0.65 mL. Prior to test article administration, the hair was clipped from the back of the animal comprising no less than 10% of the total body surface area as estimated using the equation $A=9.6*W^{2/3}$ where A was the estimated total body surface in square centimeters and W was the body weight in grams. The area was adjusted weekly by group based on the mean body weight for each sex. Following 182 days of administration, 5 animals/sex/group were maintained for a 12-week recovery period.

Observations for morbidity, mortality, injury, and the availability of food and water were conducted twice daily for all animals. Ophthalmoscopic examinations were conducted pretest on all animals and prior to the terminal and recovery necropsies on all main study animals by doctors of veterinary medicine with Diplomate, American College of Veterinary Ophthalmologists credentials.

One female at 9% DMSO (Low dose), two males and one female at 90% DMSO (High dose) died, and two females at 45.5% DMSO (Mid dose), and one female at 90% DMSO were euthanized in extremis during the study. None of these deaths were considered to be related to treatment.

No test article-related ophthalmoscopic abnormalities were detected in any animal during the pretest, terminal, and recovery ophthalmoscopic examinations. At the recovery ophthalmoscopic examination, one female at 45.5% DMSO was seen with superficial keratitis in both eyes. This isolated common finding was considered incidental to treatment.

Example 7

A Single-Dose Pharmacokinetic Evaluation of a Topical Solution Containing 1.5% w/w Diclofenac Sodium and 45.5% DMSO in Normal Healthy Non-Smoking Male and Female Subjects This Example describes novel clinical information that may, for example, be provided to a user according to the present invention, comprising the results of study conducted to evaluate the pharmacokinetics of diclofenac sodium, dimethyl sulfoxide (DMSO) and dimethyl sulfone (the major metabolite of DMSO) after a single-dose application of a topical diclofenac preparation containing 1.5% diclofenac sodium (2-[(2,6-dichlorophenyl)amino]benzeneacetic acid, monosodium salt), 45.5% DMSO, ethanol, propylene glycol, glycerine, and water ("Topical Diclofenac Solution" [Pennsaid® (Nuvo Research Inc, Mississauga, Ontario Canada]). The study followed a one-period, open-label, single-dose design in 18 normal, healthy, non-smoking male and female subjects in which Topical Diclofenac Solution was applied to both knees of each subject in the study.

The 18 subjects enrolled in the study consisted of 14 Caucasians, 1 Asian and 3 Blacks (9 males, 9 females) with a mean age of 33 years (range=22 to 46 years). The subjects' mean height was 174 cm (range=163 to 188 cm) and the mean weight was 75 kg (range=54 to 90 kg).

Each subject was instructed to apply Topical Diclofenac Solution to clean knees, total 40 drops per knee: 10 drops each to the front of the knee, to each side and to the back. To avoid spillage, the subject was instructed to apply and spread 5 drops at a time, directly onto his/her hand, and then onto the site. The application left the area visibly wet for several minutes and was applied without massaging. Topical Diclofenac Solution was applied to both knees; the order of application did not matter. After each dosing, subjects waited for the application site to dry prior to dressing. The subject washed his/her hands after complete application to both knees.

The subjects fasted overnight for at least ten hours prior to Topical Diclofenac Solution administration and at least four hours following dosing. The treatments were administered topically to both knees in each subject starting at 7:00 a.m. (0.0 hour), with three-minute intervals between subjects.

Subjects were informed not to take any prescription medication, other than hormonal contraceptives, from at least 14 days prior to the study until the end of the study. Subjects were also advised not to take any over-the-counter drugs, except for spermicidal barrier contraceptive products, for at least seven days prior to the study up until the end of the study. They were specifically reminded that this included cold preparations, Aspirin®, Bufferin®, Excedrin®, Anacin®, etc., herbal/natural supplements, vitamins and antacid (magnesium and aluminum hydroxide) preparations. Subjects were informed that concomitant medication, whether prescription or over-the-counter, was not permitted during the study. Subjects were requested to abstain from grapefruit products, xanthine- and caffeine-containing foods and beverages (this included tea, coffee, chocolate and cola drinks) for 24 hours prior to the start of the study and until after the final blood draws for the study. Subjects were also requested to abstain from alcohol products for 48 hours prior to the start of the study and until after the final blood draws of the study.

Blood samples were collected at 0.0 hour (pre-dose), 1.0, 2.0, 4.0, 6.0, 8.0, 10.0, 12.0, 24.0, 36.0, 48.0, 60.0, 72.0, 96.0, 120.0, 144.0, 168.0, 192.0, 216.0 and 240.0 (hours post-dose).

The blood samples were kept in an ice bath prior to centrifugation and were centrifuged as soon as possible (within 30 minutes) under refrigerated conditions at 3,500 rpm for seven minutes. The plasma was removed from each blood collection tube and aliquotted into pre-cooled, labeled, duplicate, polypropylene tubes, kept in an ice bath prior to being flash frozen in an upright position, in a dry-ice acetone bath and stored frozen at minus (−) 70° C.±10° C. The tubes were labeled with the study number, dosing period, subject number, study period, sampling time point, aliquot/tube number and matrix. Upon completion of the clinical portion of the study, all samples were transported in dry-ice to an analytical laboratory (Maxxam Analytics Inc.) for the analysis of diclofenac sodium, dimethyl sulfoxide and dimethyl sulfone using validated analytical methods.

Dimethyl sulfone was below the limit of quantitation in most samples and therefore pharmacokinetic analysis was not conducted. Graphs showing the average measured diclofenac sodium concentration and DMSO concentration in the subjects as a function of time are provided in FIGS. 3 and 4.

Pharmacokinetic analysis of the data was conducted using WinNonlin version 4.0 (Pharsight, Carry, US). The principal statistical software used was SAS®, version 8.00 (Statistical Analysis System). Results for pharmacokinetic parameters are summarized in the following tables.

| Pharmacokinetic Parameter | PENNSAID® TOPICAL SOLUTION n = 18 Mean ± SD |
|---|---|
| $AUC_{0-t}$ (ng · hr/mL) | 177.51 ± 72.62 |
| $AUC_{0-inf}$ (ng · hr/mL)† | 196.27 ± 68.47 |
| $C_{max}$ (ng/mL) | 8.05 ± 5.94 |
| $T_{max}$ (hr) | 11.01 ± 6.44 |
| $t_{1/2}$ (hr)† | 36.72 ± 20.82 |
| $K_{el}$ (hr$^{-1}$)† | 0.024 ± 0.0098 |
| CL/F (L/hr)† | 244.66 ± 84.72 |

†n = 13

Single-Dose Pharmacokinetic Parameters for Diclofenac Sodium (for Two Knee Application)

| Pharmacokinetic Parameter | PENNSAID® TOPICAL SOLUTION n = 18 Mean ± SD |
|---|---|
| $AUC_{0-t}$ (µg · hr/mL) | 8.719 ± 4.611 |
| $AUC_{0-inf}$ (µg · hr/mL)† | 9.174 ± 3.751 |
| $C_{max}$ (µg/mL) | 0.475 ± 0.335 |
| $T_{max}$ (hr) | 8.451 ± 2.708 |
| $t_{1/2}$ (hr)† | 8.422 ± 7.307 |
| $K_{el}$ (hr$^{-1}$)† | 0.1136 ± 0.0470 |
| CL/F (L/hr)† | 163.49 ± 64.14 |

†n = 9

Single-Dose Pharmacokinetic Parameters for Dimethyl Sulfoxide (for Two Knee Application)

Meanings of each of the parameters in the tables above are as follows:

$AUC_{0-t}$ Area under the concentration-time curve from time zero to time of last sampling time point $AUC_{0-inf}$ Area under the concentration-time curve from time zero to infinity $C_{max}$ Maximum plasma concentration after dosing $T_{max}$ Time to occurrence of Cmax $t_{1/2}$ Apparent elimination half-life $K_{el}$ Apparent elimination rate constant CL/F Apparent total body clearance Example 8

A Multi-Dose Pharmacokinetic Evaluation of a Topical Solution Containing 1.5% w/w Diclofenac Sodium and 45.5% DMSO in Normal Healthy Non-Smoking Male and Female Subjects This Example describes novel clinical information that may, for example, be provided to a user according to the present invention, comprising the results of a study conducted to evaluate the pharmacokinetics of diclofenac sodium, dimethyl sulfoxide and dimethyl sulfone after multiple doses of a topical diclofenac preparation containing 1.5% diclofenac sodium (2-[(2,6-dichlorophenyl)amino]benzeneacetic acid, monosodium salt), 45.5% DMSO, ethanol, propylene glycol, glycerine, and water ("Topical Diclofenac Solution" [Pennsaid® (Nuvo Research Inc, Mississauga, Ontario Canada]) which, as in the previous Example 7, was applied to both knees of each subject. This study followed a one-period, open-label, multiple-dose design in 20 normal healthy, non-smoking male and female subjects.

Twenty subjects (10 males, 10 females) with a mean age of 33 years (range=18 to 43 years) were enrolled in this study. The subjects' mean height was 171 cm (range=157 to 185 cm) and their mean weight was 69 kg (range=48 to 87 kg). The subjects consisted of 15 Caucasians, 3 Asians and 2 Blacks.

The treatment (40 drops, applied on the knee four times a day) was carried on for 7 days, and the pharmacokinetic profile was characterized on Day 8 after the 29th administration. Each dose of Topical Diclofenac Solution was applied to the knee following the procedure described previously in Example 7.

Doses were applied either at a clinic or at home according to following schedule:

Days 1 and 6: The subjects applied the first dose of Topical Diclofenac Solution to both knees in the clinic under supervision. The subjects applied the second, third and fourth doses of Topical Diclofenac Solution at home.

Days 2 to 5: The subjects applied all four doses of Topical Diclofenac Solution at home.

Day 7: The subjects applied the first dose of Topical Diclofenac Solution in the clinic and then exited. The second and third doses were applied at home. The fourth dose was applied in the clinic.

Day 8: The subjects applied the last dose of Topical Diclofenac Solution to both knees in the clinic following an overnight fast of at least ten hours.

Blood samples were drawn according to the following:

Days 1 and Day 6: 0.0 hour (pre-dose).

Day 7: 0.0 hour (pre-dose).

Day 8: 0.0 hour (pre-dose), 1.0, 2.0, 4.0, 6.0, 8.0, 12.0, 24.0, 36.0, 48.0, 60.0, 72.0, 96.0, 120.0, 168.0, 216.0, 264.0, 312.0 and 360.0 hours post 0.0 hour post-drug administration Day 8.

Blood samples were processed and analyzed using the methods described previously in Example 7.

One subject dropped out of the study for personal reasons so plasma concentration data from the 19 subjects who received the Topical Diclofenac Solution and who completed the study period were used in the pharmacokinetic analyses.

Steady state was achieved on Day 6 (after 20 doses) for the 3 molecular entities analyzed. On Day 8, diclofenac sodium remained measurable up to 360 hours post-dose in 11 subjects. On Day 8, DMSO and dimethyl sulfone ("$DMSO_2$") remained measurable up to 120 hours (10 subjects) and 216 hours (9 subjects) post-dose, respectively.

Figure 5:
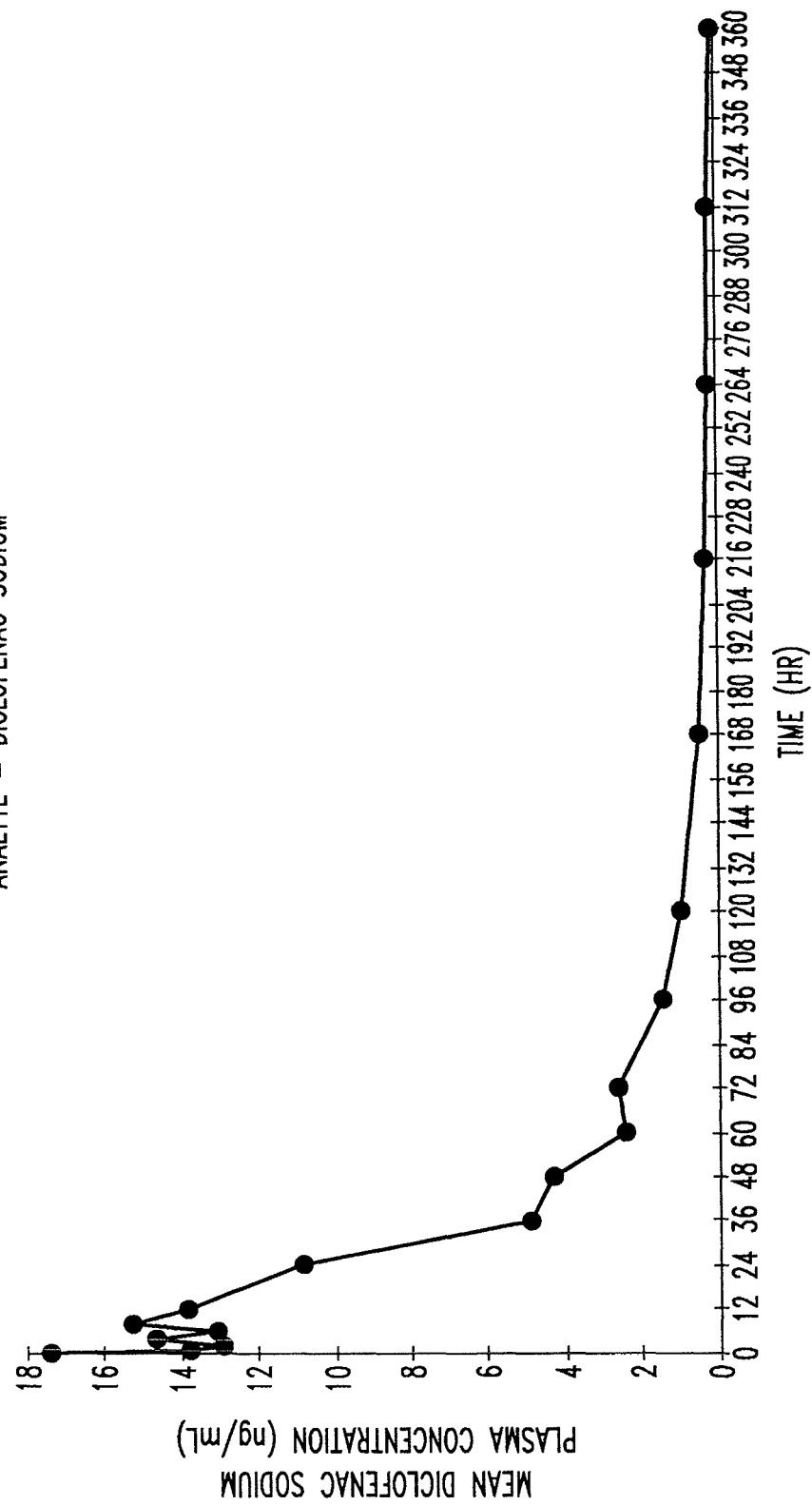
FIG. 5 shows mean plasma concentration-time profile for diclofenac sodium (ng/mL).
Figure 6:
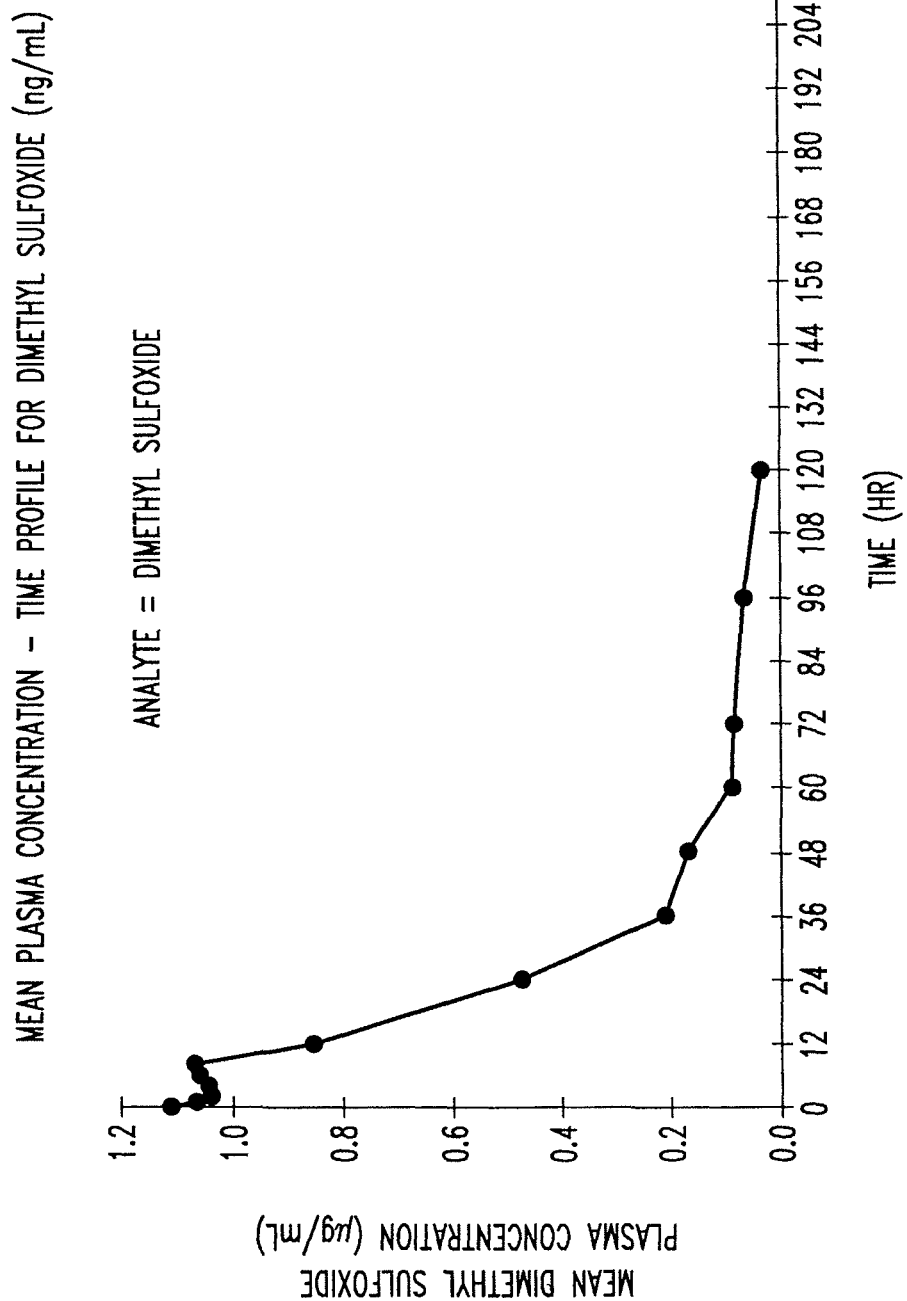
FIG. 6 shows mean plasma concentration-time profile for dimethyl sulfoxide (μg/mL).
Figure 7:
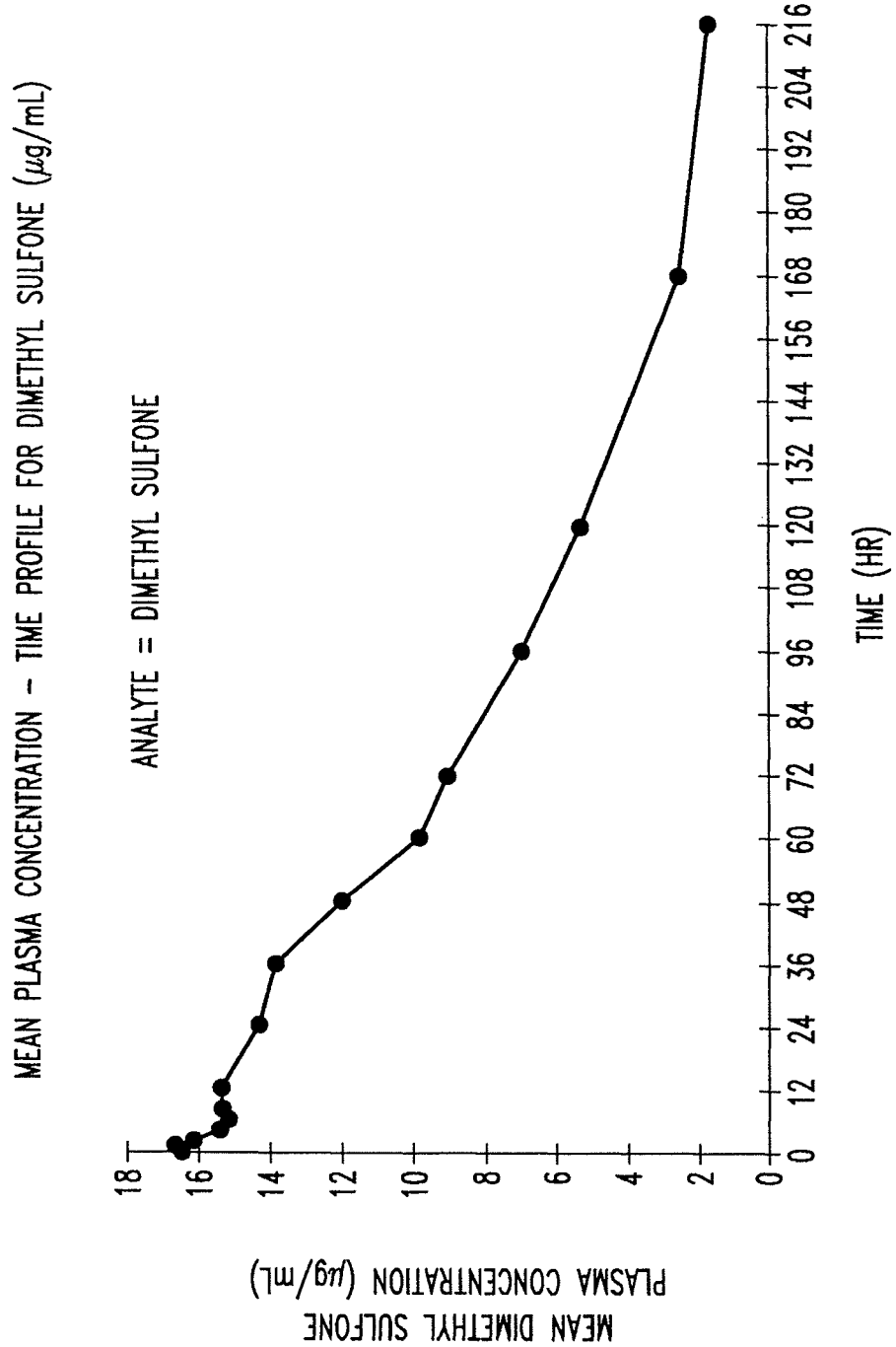
FIG. 7 shows mean plasma concentration-time profile for dimethyl sulfone (μg/mL).
Figure 8:
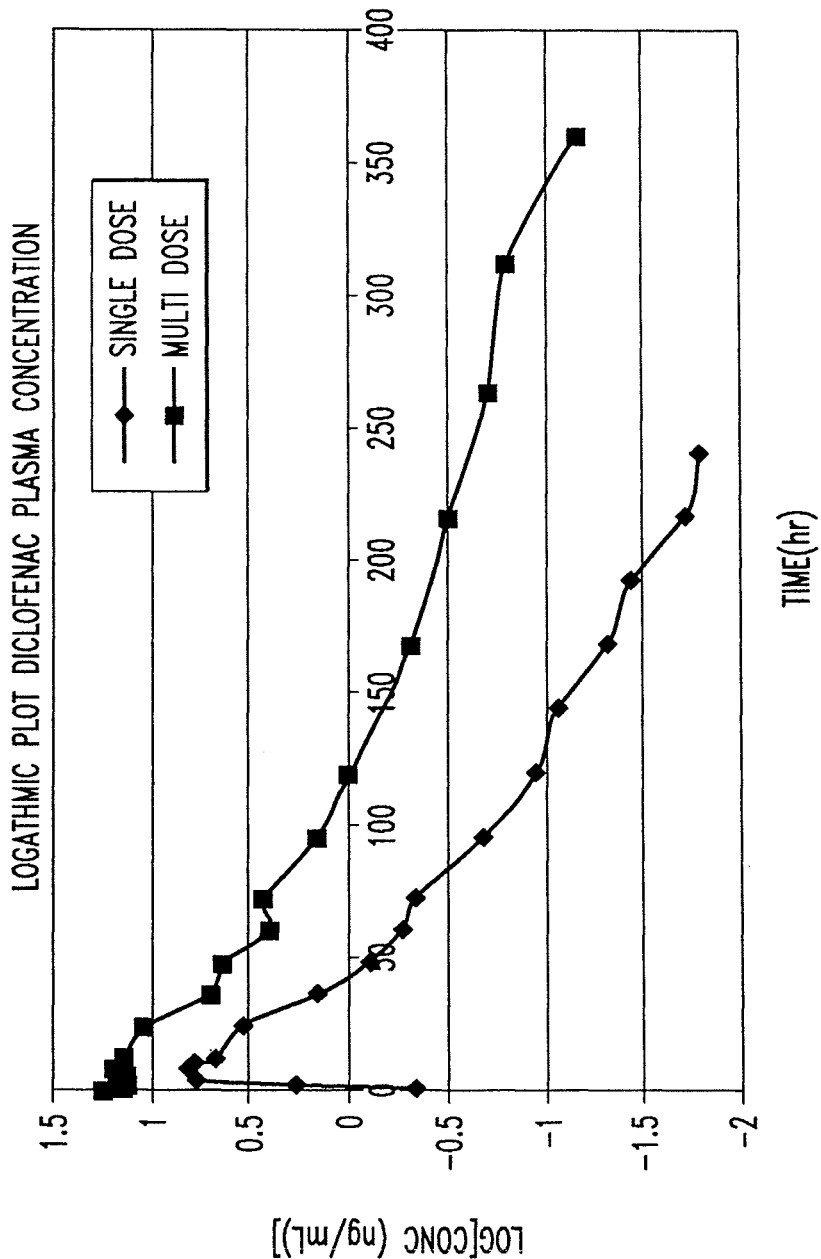
FIG. 8 shows log diclofenac plasma concentration versus time after single and multiple dose application of a topical solution containing 1.5% w/w diclofenac sodium and 45.5% DMSO.

Plots of Diclofenac, DMSO and $DMSO_2$ concentrations are provided in FIGS. 5-7.

The pharmacokinetic analysis was conducted using Win-Nonlin Version 4.0 (Pharsight, Carry, US). The principal statistical software used was SAS®, version 8.00. Results for important pharmacokinetic parameters are provided in the tables below.

| Pharmacokinetic Parameter | PENNSAID ® TOPICAL SOLUTION n = 19 Mean ± SD |
|---|---|
| $AUC_{0-t}$ (ng · hr/mL) | 695.398 ± 348.866 |
| $AUC_{0-inf}$ (ng · hr/mL)† | 745.192 ± 374.740 |
| $C_{max}$ (ng/mL) | 19.415 ± 9.326 |
| $T_{max}$ (hr) | 4.005 ± 6.541 |
| $t_{1/2}$ (hr)† | 78.972 ± 38.133 |
| $K_{el}$ (hr$^{-1}$)† | 0.0105 ± 0.0040 |

†n = 15

Multiple-Dose Pharmacokinetic Parameters for Diclofenac Sodium (for Two-Knee Application)

| Pharmacokinetic Parameter | PENNSAID ® TOPICAL SOLUTION n = 19 Mean ± SD |
|---|---|
| $AUC_{0-t}$ (ug · hr/mL) | 31.887 ± 15.520 |
| $AUC_{0-inf}$ (ug · hr/mL)† | 35.979 ± 15.419 |
| $C_{max}$ (ug/mL) | 1.206 ± 0.575 |
| $T_{max}$ (hr) | 3.842 ± 3.468 |
| $t_{1/2}$ (hr)† | 43.123 ± 22.968 |
| $K_{el}$ (hr$^{-1}$)† | 0.0213 ± 0.0124 |

†n = 13

Multiple-Dose Pharmacokinetic Parameters for Dimethyl Sulfoxide (for Two-Knee Application)

| Pharmacokinetic Parameter | PENNSAID ® TOPICAL SOLUTION n = 19 Mean ± SD |
|---|---|
| $AUC_{0-t}$ (ug · hr/mL) | 1525.292 ± 1065.245 |
| $AUC_{0-inf}$ (ug · hr/mL)† | 2339.190 ± 1276.555 |
| $C_{max}$ (ug/mL) | 18.033 ± 10.587 |
| $T_{max}$ (hr) | 9.397 ± 13.341 |
| $t_{1/2}$ (hr)† | 61.287 ± 18.376 |
| $K_{el}$ (hr$^{-1}$)† | 0.0123 ± 0.0039 |

†n = 11

Multiple-Dose Pharmacokinetic Parameters for Dimethyl Sulfone (for Two-Knee Application)

Quantities reported in the above tables have the meanings provided previously in Example 7. Origin of time (t=0) for calculation of $AUC_{0-t}$ and $AUC_{0-inf}$ is time of the last dose of drug on Day 8.

It will be appreciated that the data provided in Examples 7 and 8 evidence that the systemic exposure to diclofenac caused by use of Topical Diclofenac Solution to treat osteoarthritis of the knee (40 drops per knee QID) is much lower than that caused by a typical oral dose of diclofenac used in treatment of osteoarthritis (e.g. 50 mg TID). For example the label of Voltaren® Gel (http://www.voltarengel.com/pdf/Voltaren-PI-10-19.pdf) reports mean $AUC_{0-24}$=3890 ng·h/mL and mean $C_{max}$ of 2270 ng/mL for subjects taking 50 mg of oral diclofenac TID. Assuming the effects of additional doses of Topical Diclofenac Solution are additive, one would conclude from the $AUC_{0-inf}$ provided in Example 7 that the Topical Diclofenac Solution osteoarthritis dose results in only about 20% of the systemic exposure to the active provided by the oral drug. The fact that Topical Diclofenac Solution is shown to be comparable in efficacy to oral diclofenac sodium for treatment of osteoarthritis (see Example 1) is very surprising in view of these facts, especially as it is widely believed that NSAIDs, such as diclofenac, exert their analgesic effects both locally and centrally. Using the data from Example 8 it also can be computed that $C_{max}$ of orally administered diclofenac is more than one hundred fold higher than $C_{max}$ for Topical Diclofenac Solution.

Example 9

Assessment of Drying Time Following Application of a Topical Formulation Containing Diclofenac Sodium to Normal Subjects The objective of this study was to assess the drying time of a topical diclofenac solution containing 1.5% diclofenac sodium, 45.5% DMSO, ethanol, propylene glycol, glycerine, and water ("Topical Diclofenac Solution") when applied topically to the skin surface of the knee following a single dose application.

Using a pre-designed template, the knee application area (100 cm$^2$ centered just above the patella) was outlined in ink (the choice of knee was assigned by randomization). Each subject received an applied dose, 0.15 mL, of Topical Diclofenac Solution to the 100 cm$^2$ area on his/her knee and spread the test article using his/her fingers to completely cover the application area just up to the margin of the demarcation (this amount of drug product corresponding to a typical areal dose of Topical Diclofenac Solution used in the treatment of osteoarthritis of the knee). The applied dose remained un-occluded throughout the study duration.

Visual and blotted assessments were made at pre-dose, immediately following dose application (approximately 2 minutes post-dose) and at 5, 10, 15, 20, 30, 60, 120, and 240 minutes after dose application to the treated knee. Assessments were conducted on 9 separate 3 cm×3 cm test sites within the 100 cm$^2$ dosed area. The pre-dose assessment was performed on the test site in the center of the dosed area. The 9 post-dose assessments were conducted on the 9 test sites, in sequence starting at one corner. Only one test site was assessed for each post-dose assessment time point.

Four parameters were defined in the protocol to assess drying time. These included the weight of the tissue/vial combination, Visual Appearance Score, Visual Adhesion Score and Visual Adsorption Score as explained further below.

The visual examination of the test sites was scored using the scale below.

Visual Appearance Score:
1. Wet, shiny with a clear look of physical solution being present,
2. Damp, shiny, visible film with no visible solution present,
3. Damp, matte appearance, visible film,
4. Dry, matte appearance, visible film,
5. Dry, no visible film Following the visual assessment, the dosed site was tested for adsorption or adherence to a 3 cm×3 cm square laboratory tissue (e.g. KimWipes). Using forceps, the tissue was removed from a sealed, previously weighed vial and gently placed onto the test site. After five seconds, the tissue was removed using forceps by one corner while monitoring its adhesion to the site. Adherence of the tissue to the test site was scored using the scale below.

Visual Adhesion Score:
1. Distinct adhesion to the full test site,
2. Light to moderate adhesion to all or a portion of the test site,
3. No adhesion to the test site.

The tissue was visually inspected for fluid adsorption to the tissue and the adsorption was scored using the scale below.

Visual Adsorption Score:
1. Demonstrates fluid adsorption to the tissue to the size of the test area,
2. Demonstrates fluid adsorption to the tissue to a size less than the test area,
3. Demonstrates no fluid adsorption to the tissue.

The tissue was placed back into its labeled vial and the vial was sealed to prevent evaporation. Within 2 hours of collection the vial was re-weighed and the weight recorded.

A total of 12 healthy adult male and female subjects participated in the study. The study was successfully completed by all 12 subjects enrolled. Data for these subjects were used in the statistical analysis, except where one subject was removed as a statistical outlier.

The results of this study indicate that dryness occurred as early as 10 minutes post-dose in most subjects, as shown by visual appearance of dryness (7/11 subjects), no adhesion of the tissue to the test site (11/11 subjects) and no fluid adsorption to the tissue (10/12 subjects). A summary of the drying time data for each of the drying time parameters is shown below:

| Parameter | Time, minutes [Mean (95% CI)] |
| --- | --- |
| Visual appearance of dryness | 15.0 (9.6-20.4) |
| No adhesion to the test site | 10.0 (Na) |
| No fluid adsorption to the tissue | 10.4 (8.8-12.1) |
| Time to 10% or Less of Peak Weight Recovered | 14.2 (8.3-20.1) |

Considering the data for all the study parameters, it can be concluded that the mean drying time for Topical Diclofenac Solution following a single dose application was approximately 15 minutes, but there was considerable variability among subjects with dryness occurring as early as 10 minutes in most subjects.

Beyond the 30 minute time point all visual appearance scores were 5 for all subjects, visual adsorption scores were 3, and differences between postdose and predose tissue/vial weights were measured as 0.00 mg. Once the drug product has dried on the surface of the skin it is anticipated that residual unabsorbed diclofenac will be crystallized on the skin surface will not be bioavailable. Therefore a patient being treated with Topical Diclofenac Solution can wash and shower after the product is dried without materially impacting the efficacy of the drug. The results of the study indicate that it is appropriate to instruct a user that a patient using Topical Diclofenac Solution should wait at least 30 minutes after putting Topical Diclofenac Solution on the knee(s) before taking a shower or bath.

Example 10

Comparison of Elimination Constant after Single and Multiple Dose Application of a Topical Solution Containing 1.5% Diclofenac Sodium and 45.5% DMSO It has been discovered that the elimination constant $K_{el}$ (which is inversely related to the half life through $K_{el}=\ln(2)/T_{1/2}$) for the topical diclofenac solution of Examples 7 and 8 is highly statistically significantly different depending on whether the solution is applied as a single dose or as multiple doses. In general it would be reasonable to assume that the effects of multiple doses of the topical solution would have additive effects on the pharmacokinetics with the result that the half-life and $K_{el}$ would be independent of dosage regime. Intriguingly, Examples 7 and 8 demonstrate that the apparent plasma half life of diclofenac is increased after multiple doses of the solution are applied as is evident in the log-linear plot showing average diclofenac plasma concentration after discontinuance of application of drug following the protocols of the previous examples. The table below provides the half life and elimination constant for each subject in the studies (NC indicates that half life was not determined due to difficulties in identifying an exponential tail in the experimental data).

| Multi Dose | | | Single Dose | | |
|---|---|---|---|---|---|
| Subject # | $T_{1/2}$ (hr) | $K_{el}$ (hr$^{-1}$) | Subject # | $T_{1/2}$ (hr) | $K_{el}$ (hr$^{-1}$) |
| 1 | 68.8 | 0.010075 | 1 | 75.96 | 0.009125 |
| 2 | 66.85 | 0.010369 | 2 | NC | NC |
| 3 | NC | NC | 3 | 19.61 | 0.035347 |
| 4 | 43.41 | 0.015967 | 4 | 21.75 | 0.031869 |
| 5 | NC | NC | 5 | NC | NC |
| 6 | 128.94 | 0.005376 | 6 | NC | NC |
| 7 | NC | NC | 7 | 23.63 | 0.029333 |
| 9 | 72.74 | 0.009529 | 8 | NC | NC |
| 10 | 90.29 | 0.007677 | 9 | 21.72 | 0.031913 |
| 11 | NC | NC | 10 | 66.44 | 0.010433 |
| 12 | 151.36 | 0.004579 | 11 | NC | NC |
| 13 | 50.18 | 0.013813 | 12 | 34.21 | 0.020262 |
| 14 | 46.64 | 0.014862 | 13 | 41.65 | 0.016642 |
| 15 | 86.11 | 0.00805 | 14 | 28.13 | 0.024641 |
| 16 | 77.48 | 0.008946 | 15 | 30.29 | 0.022884 |
| 17 | 52.36 | 0.013238 | 16 | 23.23 | 0.029838 |
| 18 | 43.36 | 0.015986 | 17 | 71.69 | 0.009669 |
| 19 | 157.25 | 0.004408 | 18 | 19 | 0.036481 |
| 20 | 48.81 | 0.014201 | | | |
| Max | 157.3 | 0.0160 | Max | 76.0 | 0.0365 |
| Min | 43.4 | 0.0044 | Min | 19.0 | 0.0091 |
| Mean | 79.0 | 0.0105 | Mean | 36.7 | 0.0237 |
| Std Dev | 38.1 | 0.0040 | Std Dev | 20.8 | 0.0098 |

Figure 9:
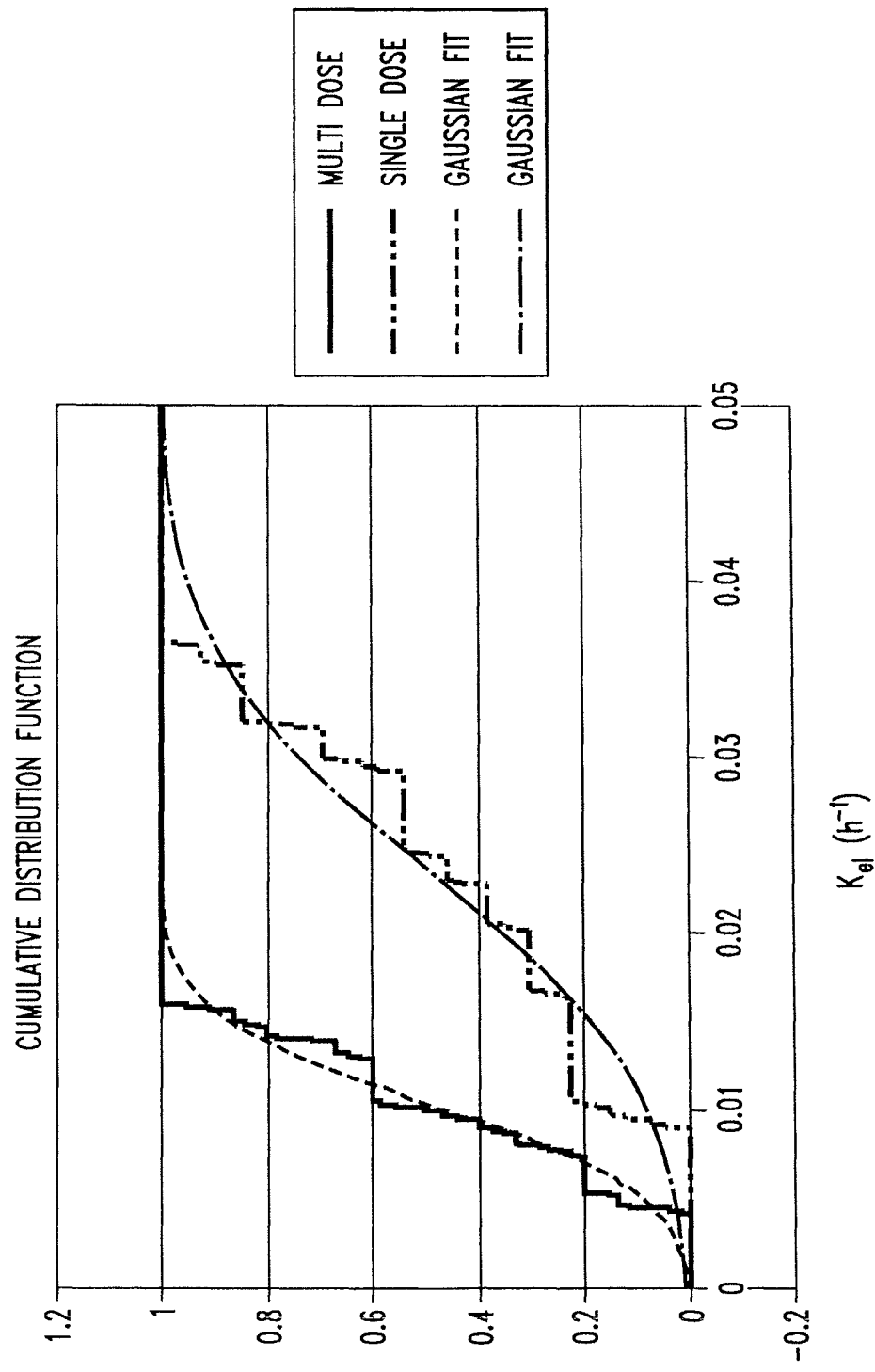
FIG. 9 shows an analysis of elimination rate constant ($K_{el}$) after single and multi dose application of a topical solution containing 1.5% w/w diclofenac sodium and 45.5% DMSO.

The distribution of the elimination constant IQ is well represented by a Normal distribution as shown in FIG. 9, which compares the cumulative distribution function of the $K_{el}$ values from each study with cumulative distribution functions for a Gaussian using mean and standard deviation (Std Dev) values provided in the table above. A t-test was performed and $K_{el}$ was found to be highly significantly different ($p<0.001$) depending on whether a single or multiple dosing regime of the topical solution was applied.

The reasons for the differences in diclofenac half life and $K_{el}$ on dosing regime are at present unknown. In general drugs with longer half lives will tend to show more uniform plasma concentrations as a function of time and may have improved safety profiles by reducing the maximum plasma concentration that a patient experiences and allowing efficacy to be achieved with a lower overall dose. This point is particularly important for patients that will use a relatively high risk drug such as diclofenac on long-term basis to treat a chronic condition such as osteoarthritis. It will therefore be appreciated that the extension of half-life observed with the multiple dosing regime of the topical diclofenac solution containing DMSO is an unexpected but fortuitous property of the solution.

Example 11

A Multi-Dose, Comparative, Exposure Study Under Maximum Use Conditions Per Labeling of Both Pennsaid® Topical Solution (Diclofenac Sodium Topical Solution 1.5% w/w and 45.5% w/w DMSO) and Solaraze® Gel (Diclofenac Sodium 3%)

A study was to conducted compare the exposure under maximum use conditions per labeling of diclofenac sodium following multiple applications of PENNSAID® Topical Solution (diclofenac sodium topical solution) 1.5% w/w and Solaraze® Gel (diclofenac sodium 3%).

The study was a two-period, open-label, non-randomized, crossover study. All subjects applied PENNSAID® to both knees for 1 week during Period 1 and Solaraze® to their actinic keratosis lesions for 4 weeks during Period 2. A 3-week washout period was observed between the last application of Period 1 and the first application of Period 2.

Thirty subjects were enrolled into the study. Thirty subjects completed Period 1 and 27 subjects completed Period 2. Pharmacokinetic and statistical analyses were performed on data obtained from the 27 subjects that completed the entire study.

The study population consisted of male and female subjects diagnosed with actinic keratosis (AK) affecting at least 500 cm2 of skin on the face, head, scalp, neck, shoulders, arms, and/or upper trunk, not necessarily continuous, of which at least 100 cm2 of the total affected area was on the face, head or scalp. Subjects were required to have a total of at least 20 non-hypertrophic AK lesions on all areas combined and a total of at least 6 non-hypertrophic AK lesions on the face, head or scalp.

During Period 1 subjects applied 40 drops (approx. 1.2 mL) q.i.d. of PENNSAID® Topical Solution (diclofenac sodium topical solution) 1.5% w/w (Nuvo Research Inc.) to each knee, 80 drops total per application, on Days 1 to 7 and dosed once on the morning of Day 8.

During Period 2 subjects applied 0.02 g/cm2 b.i.d of Solaraze® Gel (diclofenac sodium 3%) to the area of skin affected by actinic keratosis, up to a maximum of 1000 cm2 area on Days 1 to 27 and once on the morning of Day 28.

Using a validated HPLC method, plasma diclofenac sodium was analyzed from blood samples collected at the following timepoints (relative to first dose of the day):

Period 1 (PENNSAID®):

Day 1: 0.0 hour (pre-dose)

Day 6 and 7: 0.0 hour (pre-dose)

Day 8: 0.0 hour (pre-dose), 0.5, 1.0, 1.5, 2.0, 2.5, 3.0, 3.5, 4.0, 5.0 and 6.0 hour Period 2 (Solaraze®):

Day 1: 0.0 hour (pre-dose)

Day 26 and 27: 0.0 hour (pre-dose)

Day 28: 0.0 hour (pre-dose), 1.0, 1.5, 2.0, 2.5, 3.0, 3.5, 4.0, 5.0, 6.0, 8.0, 10.0 and 12.0 hour Pharmacokinetic parameters for plasma diclofenac sodium were calculated for each treatment period by standard non-compartmental methods: $C_{max(ss)}$, $C_{mm(ss)}$, $C_{avg(ss)}$, $AUC_{T(ss)}$, $AUC_{0-24(ss)}$, $T_{max(ss)}$. For PENNSAID®, $AUC_{T(ss)}$ was calculated over the dosing interval of 0-6 hours, and for Solaraze®, $AUC_{T(ss)}$ was calculated over the dosing interval of 0-12 hours. For each treatment $AUC_{T(ss)}$ was adjusted to a 24-hour exposure parameter, $AUC_{0-24(ss)}$ (calculated as $AUC_{T(ss)} \times 2$ for Solaraze® and $AUC_{T(ss)} \times 4$ for PENNSAID®), so that a comparison between the exposure of each treatment was assessed on a daily basis.

Steady-state of plasma diclofenac was attained within 8 days for PENNSAID® and within 28 days for Solaraze®. The calculated $C_{max(ss)}$, $C_{min(ss)}$, $C_{avg(ss)}$, $AUC_{T(ss)}$ and $AUC_{0-24(ss)}$ of diclofenac were substantially lower and $T_{max(ss)}$ was shorter following the maximum therapeutic dose of PENNSAID® compared to that observed following the application of Solaraze® as per label as summarized in the table below.

| Summary Statistics of Pharmacokinetic Parameters* (mean [SD]) | | | |
|---|---|---|---|
| PK Parameter | | PENNSAID ® N = 30 | Solaraze ® N = 27 |
| $C_{max(ss)}$ | (ng/mL) | 35.0 (28.6) | 125.9 (119.3) |
| $C_{min(ss)}$ | (ng/mL) | 16.7 (10.4) | 30.4 (19.4) |
| $C_{avg(ss)}$ | (ng/mL) | 24.2 (16.3) | 72.3 (63.5) |
| $AUC_{T(ss)}$ | (ng · h/mL) | 144.9 (98.0) | 868.1 (762.2) |

| Summary Statistics of Pharmacokinetic Parameters* (mean [SD]) | | | |
|---|---|---|---|
| PK Parameter | | PENNSAID ® N = 30 | Solaraze ® N = 27 |
| $AUC_{0-24(ss)}$ | (ng · h/mL) | 579.7 (392.2) | 1736.3 (1524.4) |
| $T_{max(ss)}$** | (h) | 1.0 | 2.5 |

*uncorrected for surface area,
**median for $T_{max(ss)}$

The analysis of the PENNSAID®/Solaraze® ratio (and corresponding 90% confidence interval [CI]) of the geometric mean for ln-transformed $C_{max(ss)}$ and $AUC_{0-24(ss)}$ for both uncorrected and corrected for surface area data (i.e. making comparison $C_{max(ss)}$ and $AUC_{0-24(ss)}$ per unit area of skin treated) revealed the rate and extent of bioavailabilty of diclofenac following the maximum therapeutic dose of PENNSAID® were approximately ⅓ that of Solaraze®, with upper confidence limits well below the 80-125% range.

| Mean Relative Bioavailability Pharmacokinetic Parameters* (ln transformed, N = 27) | | | |
|---|---|---|---|
| Parameter | PENNSAID ® | Solaraze ® | Ratio, % (90% CI) |
| Uncorrected | | | |
| $C_{max(ss)}$ | 26.9 | 91.8 | 29.4 (21.7-39.7) |
| $AUC_{0-24(ss)}$ | 474.2 | 1346.2 | 35.2 (27.6-45.0) |
| Corrected for Surface Area | | | |
| $C_{max(ss)}$ | 0.025 | 0.0739 | 34.2 (25.0-46.9) |
| $AUC_{0-24(ss)}$ | 0.39 | 1.24 | 31.5 (24.4-40.7) |

*least square mean

ATTACHMENT

HIGHLIGHTS OF PRESCRIBING INFORMATION
These highlights do not include all the information needed to use PENNSAID® Topical Solution safely and effectively. See full prescribing information for PENNSAID Topical Solution.
PENNSAID Topical Solution (diclofenac sodium topical solution) 1.5% w/w is for topical use only.
Initial U.S. Approval: 1988
WARNING: CARDIOVASCULAR AND GASTROINTESTINAL RISK
See full prescribing information for complete boxed warning.
Cardiovascular Risk
- Non steroidal anti-inflammatory drugs (NSAIDs) may cause an increased risk of serious cardiovascular thrombotic events, myocardial infarction, and stroke, which can be fatal. Patients with cardiovascular disease or risk factors for cardiovascular disease may be at greater risk. ( (5.1)
- PENNSAID Topical Solution is contraindicated for the treatment of peri-operative pain in the setting of coronary artery bypass graft (CABG) surgery. (4)

Gastrointestinal Risk
- NSAIDs, including PENNSAID Topical Solution, cause an increased risk of serious gastrointestinal adverse events including bleeding, ulceration, and perforation of the stomach or intestines, which can be fatal. These events can occur at any time during use and without warning symptoms. Elderly patients are at greater risk for serious gastrointestinal events. (5.2)

----------INDICATIONS AND USAGE----------
PENNSAID Topical Solution is a nonsteroidal anti-inflammatory drug (NSAID) indicated for the treatment of signs and symptoms of osteoarthritis of the knee(s). (1)

----------DOSAGE AND ADMINISTRATION----------
For the relief of the signs and symptoms of osteoarthritis of the knee(s), the recommended dose is 40 drops on each painful knee, 4 times a day. (2)
- Apply PENNSAID Topical Solution to clean, dry skin. (2.1)
- Dispense PENNSAID Topical Solution 10 drops at a time either directly onto the knee or first into the hand and then onto the knee. Spread PENNSAID Topical Solution evenly around front, back and sides of the knee. Repeat this procedure until 40 drops have been applied and the knee is completely covered with solution. (2.1)
- Wash hands completely after administering the product.
- Wait until the area is completely dry before covering with clothing or applying sunscreen, insect repellent, cosmetics, topical medications, or other substances.
- Do not get Pennsaid in your eyes, nose or mouth.

----------DOSAGE FORMS AND STRENGTHS----------
- 1.5% w/w topical solution (3)

---------------------------CONTRAINDICATIONS---------------------------
- Known hypersensitivity to diclofenac sodium. (4)
- History of asthma, urticaria, or allergic-type reactions after taking aspirin or other NSAIDs. (4)
- Use in the perioperative period of coronary artery bypass graft (CABG) surgery. (4)

------------------------WARNINGS AND PRECAUTIONS -------------------------
- Serious and potentially fatal cardiovascular thrombotic events, myocardial infarction, and stroke can occur with NSAID treatment. Use the lowest effective dose of PENNSAID Topical Solution in patients with known CV disease or risk factors for CV disease. (5.1)
- NSAIDs can cause serious gastrointestinal (GI) adverse events including inflammation, bleeding, ulceration, and perforation. Prescribe PENNSAID Topical Solution with caution in those with a prior history of ulcer disease or gastrointestinal bleeding. (5.2)
- Elevation of one or more liver tests may occur during therapy with NSAIDs. Discontinue PENNSAID Topical Solution immediately if abnormal liver tests persist or worsen. (5.3)
- Hypertension can occur with NSAID treatment. Monitor blood pressure closely with PENNSAID Topical Solution treatment. (5.4)
- Use PENNSAID Topical Solution with caution in patients with fluid retention or heart failure. (5.5)
- Long-term administration of NSAIDs can result in renal papillary necrosis and other renal injury. Use PENNSAID Topical Solution with caution in patients at greatest risk of this reaction, including the elderly, those with impaired renal function, heart failure, liver dysfunction, and those taking diuretics and ACE inhibitors. (5.6)
- Anaphylactoid reactions may occur in patients with the aspirin triad or in patients without prior exposure to PENNSAID Topical Solution.E (5.7)
- NSAIDs can cause serious skin adverse events such as exfoliative dermatitis, Stevens-Johnson Syndrome (SJS), and toxic epidermal necrolysis (TEN), which can be fatal. (5.8)
- Not for use during pregnancy (5.9)
- Do not administer to patients with aspirin sensitive asthma and use with caution in patients with preexisting asthma. (5.10)
- Avoid exposure of treated knee(s) to natural or artificial sunlight (5.11)
- Avoid contact of PENNSAID Topical Solution with eyes and mucosa (5.12)
- Avoid concurrent use with oral NSAIDs (5.13)

-----------------------------ADVERSE REACTIONS-----------------------------
The most common adverse events with PENNSAID Topical Solution are application site reactions. (6.1)

To report SUSPECTED ADVERSE REACTIONS, contact Mallinckrodt Brand Pharmaceuticals, Inc. at 1-800-xxx-xxxx or FDA at 1-800-FDA-1088 or www.fda.gov/medwatch.

------------------------DRUG INTERACTIONS-----------------------
- Concomitant administration of diclofenac and aspirin is not generally recommended because of the potential of increased adverse effects including increased GI bleeding. (7.1)
- Concomitant use of anticoagulants and diclofenac have a risk of serious GI bleeding higher than users of either drug alone. (7.2)

-----------------USE IN SPECIFIC POPULATIONS-----------------
- Pregnancy: Not recommended for use during pregnancy. (8.1)
- Nursing Mothers: Use with caution, as it is not known if diclofenac is excreted in human milk. (8.3)

See 17 for PATIENT COUNSELING INFORMATION and Medication Guide.
Revised: 02/2009

FULL PRESCRIBING INFORMATION: CONTENTS\*
WARNING: CARDIOVASCULAR AND GASTROINTESTINAL RISK
INDICATIONS AND USAGE
DOSAGE AND ADMINISTRATION
2.1 General Instructions
2.2 Special Precautions
DOSAGE FORMS AND STRENGTHS
CONTRAINDICATIONS
WARNINGS AND PRECAUTIONS
5.1 Cardiovascular Thrombotic Events
5.2 Gastrointestinal Effects – Risk of GI Ulceration, Bleeding, and Perforation
5.3 Hepatic Effects
5.4 Hypertension
5.5 Congestive Heart Failure and Edema
5.6 Renal Effects
5.7 Anaphylactoid Reactions
5.8 Skin Reactions
5.9 Pregnancy
5.10 Preexisting Asthma
5.11 Sun Exposure
5.12 Eye Exposure
5.13 Oral Nonsteroidal Anti-inflammatory Drugs
5.14 Corticosteroid Treatment
5.15 Inflammation
5.16 Hematological Effects
5.17 Monitoring ADVERSE REACTIONS
6.1 Clinical Studies Experience
6.2 Postmarketing Experience
DRUG INTERACTIONS
7.1 Aspirin
7.2 Anticoagulants
7.3 ACE–Inhibitors
7.4 Diuretics
7.5 Lithium
7.6 Methotrexate
7.7 Cyclosporine
7.8 Oral Nonsteroidal Anti-inflammatory Drugs
7.9 Topical Treatments
USE IN SPECIFIC POPULATIONS
8.1 Pregnancy
8.2 Labor and Delivery
8.3 Nursing Mothers
8.4 Pediatric Use
8.5 Geriatric Use
10. OVERDOSAGE
11. DESCRIPTION
12. CLINICAL PHARMACOLOGY
12.1 Mechanism of Action
12.2 Pharmacodynamics
12.3 Pharmacokinetics
12.4 Platelets
NONCLINICAL TOXICOLOGY
13.1 Carcinogenesis, Mutagenesis, Impairment of Fertility
13.2 Animal Toxicology and/or Pharmacology
14. CLINICAL STUDIES
14.1 Pivotal Studies in Osteoarthritis of the Knee
16. HOW SUPPLIED/STORAGE AND HANDLING
17. PATIENT COUNSELING INFORMATION
17.1 Medication Guide
17.2 Cardiovascular Effects
17.3 Gastrointestinal Effects
17.4 Hepatotoxicity
17.5 Adverse Skin Reactions
17.6 Weight Gain and Edema
17.7 Anaphylactoid Reactions
17.8 Effects during Pregnancy
17.9 Eye Exposure
Sections or subsections omitted from the full prescribing information are not listed.

FULL PRESCRIBING INFORMATION

> WARNING: CARDIOVASCULAR AND GASTROINTESTINAL RISK
> Cardiovascular Risk
> - Nonsteroidal anti-inflammatory drugs (NSAIDs) may cause an increased risk of serious cardiovascular thrombotic events, myocardial infarction, and stroke, which can be fatal. This risk may increase with duration of use. Patients with cardiovascular disease or risk factors for cardiovascular disease may be at greater risk *[see Warnings and Precautions (5.1)]*.
> - PENNSAID Topical Solution is contraindicated in the peri-operative setting of coronary artery bypass graft (CABG) surgery *[see Contraindications (4)]*.
>
> Gastrointestinal Risk
> - NSAIDs cause an increased risk of serious gastrointestinal adverse events including bleeding, ulceration, and perforation of the stomach or intestines, which can be fatal. These events can occur at any time during use and without warning symptoms. Elderly patients are at greater risk for serious gastrointestinal events *[see Warnings and Precautions (5.2)]*.

1. INDICATIONS AND USAGE

PENNSAID Topical Solution is a nonsteroidal anti-inflammatory drug (NSAID) indicated for the treatment of signs and symptoms of osteoarthritis of the knee(s).

2. DOSAGE AND ADMINISTRATION

2.1 General Instructions

For the relief of the signs and symptoms of osteoarthritis of the knee(s), the recommended dose is 40 drops per knee, 4 times a day.

Apply PENNSAID Topical Solution to clean, dry skin.

To avoid spillage, dispense PENNSAID 10 drops at a time either directly onto the knee or first into the hand and then onto the knee. Spread PENNSAID Topical Solution evenly around front, back and sides of the knee. Repeat this procedure until 40 drops have been applied and the knee is completely covered with solution.

To treat the other knee, if symptomatic, repeat the procedure.

Application of PENNSAID Topical Solution in an amount exceeding or less than the recommended dose has not been studied and is therefore not recommended.

2.2 Special Precautions

- Avoid showering/bathing for at least 30 minutes after the application of PENNSAID Topical Solution to the treated knee.
- Wash and dry hands after use.
- Do not apply PENNSAID Topical Solution to open wounds.
- Avoid contact of PENNSAID Topical Solution with eyes and mucous membranes.
- Do not apply external heat and/or occlusive dressings to treated knees.
- Avoid wearing clothing over the PENNSAID Topical Solution-treated knee until the treated knee is dry.
- Protect the treated knee(s) from sunlight.
- Wait until the treated area is dry before applying sunscreen, insect repellant, lotion, moisturizer, cosmetics, or other topical medication to the same knee you have just treated with PENNSAID Topical Solution.

3. DOSAGE FORMS AND STRENGTHS

1.5% w/w topical solution

4. CONTRAINDICATIONS

PENNSAID Topical Solution is contraindicated in patients with a known hypersensitivity to diclofenac sodium or any other component of PENNSAID Topical Solution.

PENNSAID Topical Solution is contraindicated in patients who have experienced asthma, urticaria, or allergic-type reactions after taking aspirin or other NSAIDs. Severe, rarely fatal, anaphylactic-like reactions to NSAIDs have been reported in such patients *[see Warnings and Precautions (5.7, 5.10)]*.

PENNSAID Topical Solution is contraindicated in the setting of coronary artery bypass graft (CABG) surgery *[see Warnings and Precautions (5.1)]*.

5. WARNINGS AND PRECAUTIONS

5.1 Cardiovascular Thrombotic Events

Clinical trials of several oral COX-2 selective and nonselective NSAIDs of up to three years duration have shown an increased risk of serious cardiovascular (CV) thrombotic events, myocardial infarction (MI), and stroke, which can be fatal. All NSAIDs, including PENNSAID and COX-2 selective and nonselective orally administered NSAIDS, may have a similar risk. Patients with known CV disease or risk factors for CV disease may be at greater risk. To minimize the potential risk for an adverse CV event in patients treated with an NSAID, use the lowest effective dose for the shortest duration possible. Physicians and patients should remain alert for the development of such events, even in the absence of previous CV symptoms. Inform patients about the signs and/or symptoms of serious CV events and the steps to take if they occur.

Two large, controlled, clinical trials of an orally administered COX-2 selective NSAID for the treatment of pain in the first 10-14 days following CABG surgery found an increased incidence of myocardial infarction and stroke *[see Contraindications (4)]*.

There is no consistent evidence that concurrent use of aspirin mitigates the increased risk of serious CV thrombotic events associated with NSAID use. The concurrent use of aspirin and NSAIDs, such as diclofenac, does increase the risk of serious GI events *[see Warnings and Precautions (5.2)]*.

5.2 Gastrointestinal Effects – Risk of GI Ulceration, Bleeding, and Perforation NSAIDs, including diclofenac, can cause serious gastrointestinal (GI) adverse events including bleeding, ulceration, and perforation of the stomach, small intestine, or large intestine, which can be fatal. These serious adverse events can occur at any time, with or without warning symptoms, in patients treated with NSAIDs. Only one in five patients who develop a serious upper GI adverse event on NSAID therapy is symptomatic. Upper GI ulcers, gross bleeding, or perforation caused by NSAIDs occur in approximately 1% of patients treated for 3-6 months, and in about 2-4% of patients treated for one year. These trends continue with longer duration of use, increasing the likelihood of developing a serious GI event at some time during the course of therapy. However, even short-term therapy is not without risk.

Prescribe NSAIDs, including Pennsaid, with extreme caution in those with a prior history of ulcer disease or gastrointestinal bleeding. Patients with a prior history of peptic ulcer disease and/or gastrointestinal bleeding who use NSAIDs have a greater than 10-fold increased risk for developing a GI bleed compared to patients with neither of these risk factors. Other factors that increase the risk of GI bleeding in patients treated with NSAIDs include concomitant use of oral corticosteroids or anticoagulants, longer duration of NSAID therapy, smoking, use of alcohol, older age, and poor general health status. Most spontaneous reports of fatal GI events are in elderly or debilitated patients and therefore, use special care when treating this population.

To minimize the potential risk for an adverse GI event, use the lowest effective dose for the shortest possible duration. Remain alert for signs and symptoms of GI ulceration and bleeding during diclofenac therapy and promptly initiate additional evaluation and treatment if a serious GI adverse event is suspected. For high-risk patients, consider alternate therapies that do not involve NSAIDs.

5.3 Hepatic Effects

Borderline elevations (less than 3 times the upper limit of the normal [ULN] range) or greater elevations of transaminases occurred in about 15% of oral diclofenac-treated patients in clinical trials of indications other than acute pain. Of the markers of hepatic function, ALT (SGPT) is recommended for the monitoring of liver injury.

In clinical trials of a oral diclofenac - misoprostol combination product, meaningful elevations (i.e., more than 3 times the ULN) of AST (SGOT) occurred in about 2% of approximately 5,700 patients at some time during diclofenac treatment (ALT was not measured in all studies).

In an open-label, controlled trial of 3,700 patients treated for 2–6 months, patients with oral diclofenac were monitored first at 8 weeks and 1,200 patients were monitored again at 24 weeks. Meaningful elevations of ALT and/or AST occurred in about 4% of the 3,700 patients and included marked elevations (>8 times the ULN) in about 1% of the 3,700 patients. In this open-label study, a higher incidence of borderline (less than 3 times the ULN), moderate (3–8 times the ULN), and marked (>8 times the ULN) elevations of ALT or AST was observed in patients receiving diclofenac when compared to other NSAIDs. Elevations in transaminases were seen more frequently in patients with osteoarthritis than in those with rheumatoid arthritis. Almost all meaningful elevations in transaminases were detected before patients became symptomatic.

Abnormal tests occurred during the first 2 months of therapy with oral diclofenac in 42 of the 51 patients in all trials who developed marked transaminase elevations. In postmarketing reports, cases of drug-induced hepatotoxicity have been reported in the first month, and in some cases, the first 2 months of NSAID therapy.

Postmarketing surveillance has reported cases of severe hepatic reactions, including liver necrosis, jaundice, fulminant hepatitis with and without jaundice, and liver failure. Some of these reported cases resulted in fatalities or liver transplantation.

In a European retrospective population-based, case-controlled study, 10 cases of oral diclofenac associated drug-induced liver injury with current use compared with non-use of diclofenac were associated with a statistically significant 4-fold adjusted odds ratio of liver injury. In this particular study, based on an overall number of 10 cases of liver injury associated with diclofenac, the adjusted odds ratio increased further with female gender, doses of 150 mg or more, and duration of use for more than 90 days.

Measure transaminases (ALT and AST) periodically in patients receiving long-term therapy with diclofenac, because severe hepatotoxicity may develop without a prodrome of distinguishing symptoms. The optimum times for making the first and subsequent transaminase measurements are not known. Based on clinical trial data and postmarketing experiences, monitor transaminases within 4 to 8 weeks after initiating treatment with diclofenac. However, severe hepatic reactions can occur at any time during treatment with diclofenac. If abnormal liver tests persist or worsen, if clinical signs and/or symptoms consistent with liver disease develop, or if systemic manifestations occur (e.g., eosinophilia, rash, abdominal pain, diarrhea, dark urine, etc.), discontinue PENNSAID immediately.

To minimize the possibility that hepatic injury will become severe between transaminase measurements, inform patients of the warning signs and symptoms of hepatotoxicity (e.g., nausea, fatigue, lethargy, diarrhea, pruritus, jaundice, right upper quadrant tenderness, and "flulike" symptoms), and the appropriate action to take if these signs and symptoms appear.

To minimize the potential risk for an adverse liver-related event in patients treated with PENNSAID, use the lowest effective dose for the shortest duration possible. Exercise caution when prescribing PENNSAID with concomitant drugs that are known to be potentially hepatotoxic (e.g. acetaminophen, certain antibiotics, antiepileptics). Caution patients to avoid taking unprescribed acetaminophen while using Pennsaid.

5.4 Hypertension

NSAIDs, including diclofenac, can lead to new onset or worsening of preexisting hypertension, either of which may contribute to the increased incidence of CV events. Use NSAIDs, including Pennsaid, with caution in patients with hypertension. Monitor blood pressure (BP) closely during the initiation of NSAID treatment and throughout the course of therapy.

Patients taking ACE inhibitors, thiazides or loop diuretics may have impaired response to these therapies when taking NSAIDs.

5.5 Congestive Heart Failure and Edema

Fluid retention and edema have been observed in some patients treated with NSAIDs, including PENNSAID Topical Solution. Use PENNSAID Topical Solution with caution in patients with fluid retention or heart failure.

5.6 Renal Effects

Use caution when initiating treatment with Pennsaid in patients with considerable dehydration.

Long-term administration of NSAIDs has resulted in renal papillary necrosis and other renal injury. Renal toxicity has also been seen in patients in whom renal prostaglandins have a compensatory role in the maintenance of renal perfusion. In these patients, administration of an NSAID may cause a dose-dependent reduction in prostaglandin formation and, secondarily, in renal blood flow, which may precipitate overt renal decompensation. Patients at greatest risk of this reaction are those with impaired renal function, heart failure, liver dysfunction, those taking diuretics and ACE inhibitors, and the elderly. Discontinuation of NSAID therapy is usually followed by recovery to the pretreatment state.

No information is available from controlled clinical studies regarding the use of PENNSAID Topical Solution in patients with advanced renal disease. Therefore, treatment with PENNSAID Topical Solution is not recommended in patients with advanced renal disease. If PENNSAID Topical Solution therapy is initiated, close monitoring of the patient's renal function is advisable.

5.7 Anaphylactoid Reactions

As with other NSAIDs, anaphylactoid reactions may occur in patients without prior exposure to PENNSAID Topical Solution. Do not prescribe PENNSAID Topical Solution to patients with the aspirin triad. This symptom complex typically occurs in asthmatic patients who experience rhinitis with or without nasal polyps, or who exhibit severe, potentially fatal bronchospasm after taking aspirin or other NSAIDs *[see Contraindications (4) and Warnings and*

*Precautions (5.10)]*. Seek emergency help in cases where an anaphylactoid reaction occurs.

5.8 Skin Reactions

Do not apply PENNSAID Topical Solution to open skin wounds, infections, inflammations, or exfoliative dermatitis, as it may affect absorption and tolerability of the drug.

NSAIDs, including PENNSAID Topical Solution, can cause serious skin adverse events such as exfoliative dermatitis, Stevens-Johnson Syndrome (SJS), and toxic epidermal necrolysis (TEN), which can be fatal. These serious events may occur without warning. Inform patients about the signs and symptoms of serious skin manifestations, and discontinue use of the drug at the first appearance of skin rash or any other signs of hypersensitivity.

5.9 Pregnancy

PENNSAID Topical Solution should not be used by pregnant or nursing women or those intending to become pregnant.

5.10 Preexisting Asthma

Patients with asthma may have aspirin-sensitive asthma. The use of aspirin in patients with aspirin-sensitive asthma has been associated with severe bronchospasm, which can be fatal. Since cross-reactivity, including bronchospasm, between aspirin and other nonsteroidal anti-inflammatory drugs has been reported in such aspirin-sensitive patients, do not administer PENNSAID Topical Solution to patients with this form of aspirin sensitivity and use with caution in patients with preexisting asthma.

5.11 Sun Exposure

Instruct patients to avoid exposure to natural or artificial sunlight on treated knee(s) because studies in animals indicated topical diclofenac treatment resulted in an earlier onset of ultraviolet light-induced skin tumors. The potential effects of PENNSAID Topical Solution on skin response to ultraviolet damage in humans are not known.

5.12 Eye Exposure

Avoid contact of PENNSAID Topical Solution with eyes and mucosa. Advise patients that if eye contact occurs, immediately wash out the eye with water or saline and consult a physician if irritation persists for more than an hour.

5.13 Oral Nonsteroidal Anti-inflammatory Drugs

Concomitant use of oral NSAIDs with PENNSAID Topical Solution resulted in a higher rate of rectal hemorrhage, more frequent abnormal creatinine, urea and hemoglobin. Therefore, do not use combination therapy with PENNSAID Topical Solution and an oral NSAID unless the benefit outweighs the risk and conduct periodic laboratory evaluations.

5.14 Corticosteroid treatment

PENNSAID Topical Solution cannot be expected to substitute for corticosteroids or to treat corticosteroid insufficiency. Abrupt discontinuation of corticosteroids may lead to exacerbation of corticosteroid-response illness. For patients on prolonged corticosteroid therapy, taper slowly if a decision is made to discontinue corticosteroids.

5.15 Inflammation

The pharmacological activity of PENNSAID Topical Solution in reducing inflammation, and possibly fever, may diminish the utility of these diagnostic signs in detecting complications of presumed noninfectious, painful conditions.

5.16 Hematological Effects

The effects of PENNSAID Topical Solution on platelet function were studied in 10 healthy subjects administered 80 drops four times a day for 7 days. There was no significant change in platelet aggregation following one week of treatment *[see Clinical Pharmacology (12.4)]*.

Anemia is sometimes seen in patients receiving NSAIDs. This may be due to fluid retention, occult or gross GI blood loss, or an incompletely described effect upon erythropoiesis. Check hemoglobin or hematocrit of patients on PENNSAID Topical Solution if they exhibit any signs or symptoms of anemia or blood loss.

NSAIDs inhibit platelet aggregation and have been shown to prolong bleeding time in some patients. Unlike aspirin, their effect on platelet function is quantitatively less, of shorter duration and reversible. Carefully monitor patients receiving PENNSAID Topical Solution who may be adversely affected by alterations in platelet function, such as those with coagulation disorders or patients receiving anticoagulants.

5.17 Monitoring

Because serious GI tract ulcerations and bleeding can occur without warning symptoms in patients taking NSAIDs, monitor patients for signs or symptoms of GI bleeding. Check CBC and a chemistry profile periodically in patients on long-term treatment with NSAIDs. Discontinue PENNSAID Topical Solution if abnormal liver tests or renal tests persist or worsen.

6. ADVERSE REACTIONS

6.1 Clinical Studies Experience

Because clinical trials are conducted under widely varying conditions, adverse reaction rates observed in the clinical trials of a drug cannot be directly compared to rates in the clinical trials of another drug and may not reflect the rates observed in practice.

The data described below reflect exposure to PENNSAID Topical Solution of 911 patients treated between 4 and 12 weeks (mean duration of 49 days) in seven Phase 3 controlled trials, as well as exposure of 793 patients treated in an open-label study, including 463 patients treated for at least 6 months, and 144 patients treated for at least 12 months. The population mean age was approximately 60 years, 89% of patients were Caucasians, 64% were females, and all patients had primary osteoarthritis. The most common adverse events with PENNSAID Topical Solution were application site skin reactions. These events were the most common reason for withdrawing from the studies.

*Application site reactions:*

In controlled trials, the most common treatment-related adverse events in patients receiving PENNSAID Topical Solution were application site skin reactions. Application site reactions were characterized by one or more of the following: dryness, erythema, induration, vesicles, paresthesia, pruritus, vasodilation, acne, and urticaria. The most frequent of these reactions were dry skin (32%), contact dermatitis characterized by skin erythema and induration (9%), contact dermatitis with vesicles (2%) and pruritus (4%). In one controlled trial, a higher rate of contact dermatitis with vesicles (4%) was observed after treatment of 152 subjects with the combination of PENNSAID Topical Solution and oral diclofenac. In the open label uncontrolled long-term safety study, contact dermatitis occurred in 13% and contact dermatitis with vesicles in 10% of patients, generally within the first 6 months of exposure, leading to a withdrawal rate for an application site event of 14%.

*Adverse events common to the NSAID class:*

In controlled trials, subjects treated with PENNSAID Topical Solution experienced some adverse events associated with the NSAID class more frequently than subjects using placebo (constipation, diarrhea, dyspepsia, nausea, flatulence, abdominal pain, edema; see Table 1). The combination of PENNSAID Topical Solution and oral diclofenac, compared to oral diclofenac alone, resulted in a higher rate of rectal hemorrhage (3% vs. less than 1%), and more frequent abnormal creatinine (12% vs. 7%), urea (20% vs. 12%), and hemoglobin (13% vs. 9%), but no difference in elevation of liver transaminases.

Table 1 lists all adverse reactions occurring in ≥1% of patients receiving PENNSAID Topical Solution, where the rate in the PENNSAID Topical Solution group exceeded placebo, from seven controlled studies conducted in patients with osteoarthritis. Since these trials were of different durations, these percentages do not capture cumulative rates of occurrence.

Table 1: Adverse Reactions occurring in ≥1% of patients treated with PENNSAID® Topical Solution in placebo and oral diclofenac-controlled trials.

| Treatment Group: | PENNSAID® Topical Solution N=911 | Topical Placebo N=332 |
|---|---|---|
| Adverse Reaction[†] | N (%) | N (%) |
| Dry Skin (Application Site) | 292 (32) | 17 (5) |
| Contact Dermatitis (Application Site) | 83 (9) | 6 (2) |
| Dyspepsia | 72 (8) | 13 (4) |
| Abdominal Pain | 54 (6) | 10 (3) |
| Flatulence | 35 (4) | 1 (<1) |
| Pruritus (Application Site) | 34 (4) | 7 (2) |
| Diarrhea | 33 (4) | 7 (2) |
| Nausea | 33 (4) | 3 (1) |
| Pharyngitis | 40 (4) | 13 (4) |
| Constipation | 29 (3) | 1 (<1) |
| Edema | 26 (3) | 0 |
| Rash (Non-Application Site) | 25 (3) | 5 (2) |
| Infection | 25 (3) | 8 (2) |
| Ecchymosis | 19 (2) | 1 (<1) |
| Dry Skin (Non-Application Site) | 19 (2) | 1 (<1) |
| Contact Dermatitis, vesicles (Application Site) | 18 (2) | 0 |
| Paresthesia (Non-Application Site) | 14 (2) | 3 (<1) |
| Accidental Injury | 22 (2) | 7 (2) |
| Pruritus (Non-Application Site) | 15 (2) | 2 (<1) |
| Sinusitis | 10 (1) | 2 (<1) |
| Halitosis | 11 (1) | 1 (<1) |
| Application Site Reaction (not otherwise specified) | 11 (1) | 3 (<1) |

[†]Preferred Term according to COSTART

6.2 Postmarketing Experience

In non-US post-marketing surveillance, the following adverse reactions have been reported during post-approval use of PENNSAID Topical Solution. Because these reactions are reported voluntarily from a population of uncertain size, it is not always possible to reliably estimate their frequency or establish a causal relationship to drug exposure.

*Body as a whole:* abdominal pain, accidental injury, allergic reaction, asthenia, back pain, body odor, chest pain, edema, face edema, halitosis, headache, lack of drug effect, neck rigidity, pain

*Cardiovascular:* palpitation, cardiovascular disorder

*Digestive:* diarrhea, dry mouth, dyspepsia, gastroenteritis, decreased appetite, mouth ulceration, nausea, rectal hemorrhage, ulcerative stomatitis

*Metabolic and Nutritional:* creatinine increased

*Musculoskeletal:* leg cramps, myalgia

*Nervous:* depression, dizziness, drowsiness, lethargy, paresthesia, paresthesia at application site

*Respiratory:* asthma, dyspnea, laryngismus, laryngitis, pharyngitis

*Skin and Appendages: At the Application Site:* contact dermatitis, contact dermatitis with vesicles, dry skin, pruritus, rash; *Other Skin and Appendages Adverse Reactions:* eczema, rash, pruritus, skin discoloration, urticaria

*Special senses:* abnormal vision, blurred vision, cataract, ear pain, eye disorder, eye pain, taste perversion

7. DRUG INTERACTIONS

Drug interactions with the use of PENNSAID Topical Solution have not been studied. The following drug interactions [sections 7.1 to 7.7] are noted for oral diclofenac sodium.

7.1 Aspirin

When diclofenac is administered with aspirin, the binding of diclofenac to protein is reduced, although the clearance of free diclofenac is not altered. The clinical significance of this interaction is not known; however, as with other NSAIDs, concomitant administration of diclofenac and aspirin is not generally recommended because of the potential of increased adverse effects.

7.2 Anticoagulants

The effects of anticoagulants such as warfarin and NSAIDs on GI bleeding are synergistic, such that users of both drugs together have a risk of serious GI bleeding higher than users of either drug alone.

7.3 ACE-Inhibitors

NSAIDs may diminish the antihypertensive effect of angiotensin converting enzyme (ACE) inhibitors. Consider this interaction in patients taking NSAIDs concomitantly with ACE-inhibitors.

7.4 Diuretics

Clinical studies, as well as post-marketing observations, have shown that NSAIDs can reduce the natriuretic effect of furosemide and thiazides in some patients. The response has been attributed to inhibition of renal prostaglandin synthesis. During concomitant therapy with NSAIDs, observe the patient closely for signs of renal failure *[see Warnings and Precautions (5.6)]*, as well as to assure diuretic efficacy.

7.5 Lithium

NSAIDs have produced an elevation of plasma lithium levels and a reduction in renal lithium clearance. The mean minimum lithium concentration increased 15% and the renal clearance was decreased by approximately 20%. These effects have been attributed to inhibition of renal prostaglandin synthesis by the NSAID. Thus, when NSAIDs, including diclofenac, and lithium are administered concurrently, observe patients carefully for signs of lithium toxicity.

7.6 Methotrexate

NSAIDs have been reported to competitively inhibit methotrexate accumulation in rabbit kidney slices. This may indicate that they could enhance the toxicity of methotrexate. Use caution when NSAIDs, including diclofenac, are administered concomitantly with methotrexate.

7.7 Cyclosporine

Diclofenac, like other NSAIDs, may affect renal prostaglandins and increase the toxicity of certain drugs. Therefore, concomitant therapy with diclofenac may increase cyclosporine's nephrotoxicity. Use caution when diclofenac is administered concomitantly with cyclosporine.

7.8 Oral Nonsteroidal Anti-inflammatory Drugs

Concomitant use of oral NSAIDs with PENNSAID Topical Solution has been evaluated in one Phase 3 controlled trial and in combination with oral diclofenac, compared to oral diclofenac alone, resulted in a higher rate of rectal hemorrhage (3% vs. less than 1%), and more frequent abnormal creatinine (12% vs. 7%), urea (20% vs. 12%) and hemoglobin (13% vs. 9%). Therefore, do not use combination therapy with PENNSAID Topical Solution and an oral NSAID unless the benefit outweighs the risk and conduct periodic laboratory evaluations.

7.9 Topical Treatments

Instruct patients that before applying sunscreen, insect repellant, lotion, moisturizer, cosmetics, or other topical medication to the same skin surface of the knee treated with PENNSAID Topical Solution, they must wait until the treated area is completely dry.

8. USE IN SPECIFIC POPULATIONS

8.1 Pregnancy

Pregnancy Category C prior to 30 weeks gestation; Category D starting 30 weeks gestation.

*Teratogenic Effects:*

There are no adequate and well-controlled studies of PENNSAID Topical Solution in pregnant women. PENNSAID Topical Solution should not be used by pregnant women as its safe use has not been adequately determined and starting at 30 weeks gestation, diclofenac and other NSAIDs should be avoided by pregnant women as premature closure of the ductus arteriosus in the fetus may occur. Developmental studies in animals demonstrated that diclofenac sodium administration did not produce teratogenicity despite the induction of maternal toxicity and fetal toxicity in mice at doses up to 20 mg/kg/day (0.6-fold the maximum recommended human dose [MRHD] of 154 mg/day based on body surface area comparison), and in rats and rabbits at doses up to 10 mg/kg/day (approximately 0.6-fold and 1.3-fold the MRHD, respectively). Published reproductive and developmental studies of dimethyl sulfoxide (DMSO, the solvent used in PENNSAID Topical Solution) are equivocal as to potential teratogenicity.

*Nonteratogenic effects*

In rats, maternally toxic doses of diclofenac were associated with dystocia, prolonged gestation, reduced fetal weights and growth, and reduced fetal survival.

8.2 Labor and Delivery

The effects of PENNSAID Topical Solution on labor and delivery in pregnant women are unknown. In rat studies maternal exposure to diclofenac, as with other NSAID drugs, known to inhibit prostaglandin synthesis, increased the incidence of dystocia, delayed parturition, and decreased offspring survival.

8.3 Nursing Mothers

It is not known whether this drug is excreted in human milk; however, there is a case report in the literature indicating that diclofenac can be detected at low levels in breast milk. Because many drugs are excreted in human milk and because of the potential for serious adverse reactions in nursing infants from PENNSAID Topical Solution, a decision should be made whether to discontinue nursing or to discontinue the drug, taking into account the importance of the drug to the mother.

8.4 Pediatric Use

Safety and effectiveness in pediatric patients have not been established.

8.5 Geriatric Use

Of the 911 patients treated with PENNSAID Topical Solution in seven controlled, Phase 3 clinical trials, 444 subjects were 65 years of age and over. There was no age-related difference in the incidence of adverse events. Of the 793 patients treated with PENNSAID Topical Solution in one open-labeled safety trial, 334 subjects were 65 years of age and over including 107 subjects 75 and over. There was no difference in the incidence of adverse events with long-term exposure to PENNSAID Topical Solution for this elderly population. As with any NSAID, use caution in treating the elderly (65 years and older) and it may be useful to monitor renal function since they are more likely to have decreased baseline renal function.

10. OVERDOSAGE

There have been no known experiences of overdose with PENNSAID Topical Solution.

Symptoms following acute NSAID overdose are usually limited to lethargy, drowsiness, nausea, vomiting, and epigastric pain, which are generally reversible with supportive care. Gastrointestinal bleeding can occur. Hypertension, acute renal failure, respiratory depression and coma may occur, but are rare. Anaphylactoid reactions have been reported with therapeutic ingestion of NSAIDs, and may occur following an overdose.

Manage patients using symptomatic and supportive care following an NSAID overdose. There are no specific antidotes. Emesis is not recommended due to a possibility of aspiration and subsequent respiratory irritation by DMSO contained in PENNSAID Topical Solution. Activated charcoal (60 to 100 g in adults, 1 to 2 g/kg in children) and/or osmotic cathartic may be indicated in patients seen within 4 hours of ingestion with symptoms or following a large overdose (5 to 10 times the usual dose). Forced diuresis, alkalinization of urine, hemodialysis, or hemoperfusion may not be useful due to high protein binding.

For additional information about overdose treatment, call a poison control center (1-800-222-1222).

11. DESCRIPTION

PENNSAID Topical Solution is a clear, colorless to faintly pink-orange solution for topical application.

PENNSAID Topical Solution contains 1.5% w/w diclofenac sodium, a benzene-acetic acid derivative that is a nonsteroidal anti-inflammatory drug (NSAID), designated chemically as 2-[(2,6-dichlorophenyl) amino] benzeneacetic acid, monosodium salt. The molecular weight is 318.14. Its molecular formula is

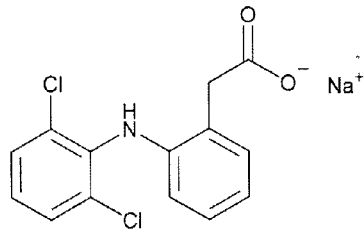

$C_{14}H_{10}Cl_2NNaO_2$ and it has the following structural formula:

Each 1 mL of solution contains 16.05 mg of diclofenac sodium. In addition, PENNSAID Topical Solution contains the following inactive ingredients: dimethyl sulfoxide USP (DMSO, 45.5% w/w), propylene glycol, alcohol, glycerin and purified water.

12. CLINICAL PHARMACOLOGY

12.1 Mechanism of Action

The mechanism of action of diclofenac is similar to that of other nonsteroidal anti-inflammatory drugs. Diclofenac inhibits the enzyme, cyclooxygenase (COX), an early component of the arachidonic acid cascade, resulting in the reduced formation of prostaglandins, thromboxanes and prostacylin. It is not completely understood how reduced synthesis of these compounds results in therapeutic efficacy.

12.2 Pharmacodynamics

Diclofenac, the active component of PENNSAID Topical Solution has anti-inflammatory, anti-nociception, and antipyretic effects.

12.3 Pharmacokinetics

After topical administration to healthy human volunteers of single and multiple maximum doses of PENNSAID Topical Solution, 40 drops (approximately 1.2 mL) to each knee (80 drops total dose), the following diclofenac pharmacokinetic parameters were obtained: (see Table 2).

Table 2: Single-dose (80 drops) and Multiple Dose (80 drops four times daily for 7 days) PENNSAID Topical Solution Pharmacokinetic Parameters

| Pharmacokinetic Parameters | Diclofenac sodium | |
|---|---|---|
| | Normal Adults [N=18] (Age: 18-55 years) | Normal Adults [N=19] (Age: 18-55 years) |
| | Single Dose | Multiple Dose Four times daily for 7 days |
| $AUC_{0-t}$ | 177.5 ± 72.6 ng.h/mL | 695.4 ± 348.9 ng.h/mL |
| $AUC_{0-inf}$ | 196.3 ± 68.5 ng.h/mL | 745.2 ± 374.7 ng.h/mL |
| Plasma $C_{max}$ | 8.1 ± 5.9 ng/mL | 19.4 ± 9.3 ng/mL |
| Plasma $T_{max}$ (h) | 11.0 ± 6.4 | 4.0 ± 6.5 |
| Plasma $t_{1/2}$ (h) | 36.7 ± 20.8 | 79.0 ± 38.1 |
| $K_{el}$ $(h^{-1})$ | 0.024 ± 0.010 | 0.011 ± 0.004 |
| CL/F (L/h) | 244.7 ± 84.7[1] | -- |

[1]Apparent total body clearance

Absorption

Diclofenac systemic exposure from PENNSAID application (4 times daily for 1 week) was approximately 1/3 of the diclofenac systemic exposure from the Solaraze (diclofenac topical gel) application (twice daily for 4 weeks).

Distribution

Diclofenac is more than 99% bound to human serum proteins, primarily to albumin.

Diclofenac diffuses into and out of the synovial fluid. Diffusion into the joint occurs when plasma levels are higher than those in the synovial fluid, after which the process reverses and synovial fluid levels are higher than plasma levels. It is not known whether diffusion into the joint plays a role in the effectiveness of diclofenac.

Metabolism

Five diclofenac metabolites have been identified in human plasma and urine. The metabolites include 4'-hydroxy-, 5-hydroxy-, 3'-hydroxy-, 4',5-dihydroxy- and 3'-hydroxy-4'-methoxy diclofenac. The major diclofenac metabolite, 4'-hydroxydiclofenac, has very weak pharmacologic activity. The formation of 4'-hydroxy diclofenac is primarily mediated by CPY2C9. Both diclofenac and its oxidative metabolites undergo glucuronidation or sulfation followed by biliary excretion. Acylglucuronidation mediated by UGT2B7 and oxidation mediated by CPY2C8 may also play a role in diclofenac metabolism. CYP3A4 is responsible for the formation of minor metabolites, 5-hydroxy and 3'-hydroxy- diclofenac.

Excretion

Diclofenac is eliminated through metabolism and subsequent urinary and biliary excretion of the glucuronide and the sulfate conjugates of the metabolites.

Little or no free unchanged diclofenac is excreted in the urine.

*Special Populations*

*Pediatric:* The pharmacokinetics of PENNSAID has not been investigated in pediatric patients.

*Race:* Pharmacokinetic differences due to race have not been studied.

12.4 Platelets

The effect of PENNSAID Topical Solution on platelet function was evaluated in 10 healthy human volunteers as a sub-study of a multiple-dose pharmacokinetic study [*see Pharmacokinetics (12.3)*]. Average (range) platelet aggregation time following stimulation with adenosine diphosphate, collagen, epinephrine and arachidonic acid was 101.3% (73.3–128.1), 99.8% (69.6–112.9), 109.9% (66.2–178.1) and 99.0% (15.5–126.6) of baseline value, respectively. These results indicate that there was no effect on platelet aggregation after application of the maximum clinical dose for 7 days [*see Pharmacokinetics (12.3)*].

13. NONCLINICAL TOXICOLOGY

13.1 Carcinogenesis, Mutagenesis, Impairment of Fertility.

Carcinogenicity studies in mice and rats administered diclofenac sodium as a dietary constituent for 2 years resulted in no significant increases in tumor incidence at does up to 2 mg/kg/day corresponding to approximately 0.35- and 0.7-fold (mouse and rat, respectively) of the maximum recommended human topical dose (MRHD) of PENNSAID Topical Solution (based on apparent bioavailability and body surface area comparison).

In a dermal carcinogenicity study conducted in albino mice, daily topical applications of diclofenac sodium for two years at concentrations up to-0.035% diclofenac sodium (a 43-fold lower diclofenac sodium concentration than present in PENNSAID Topical Solution) did not increase neoplasm incidence.

In a photococarcinogenicity study conducted in hairless mice, topical application of diclofenac sodium at doses up to 0.035% diclofenac sodium (a 43-fold lower diclofenac sodium concentration than present in PENNSAID Topical Solution) resulted in an earlier median time of onset of tumors.

Mutagenesis: Diclofenac was not mutagenic or clastogenic in a battery of genotoxicity tests that included the bacterial reverse mutation assay, *in vitro* mouse lymphoma point mutation assay, chromosomal aberration studies in Chinese hamster ovarian cells *in vitro*, and *in vivo* rat chromosomal aberration assay of bone marrow cells.

Impairment of Fertility: Fertility studies have not been conducted with Pennsaid Topical Solution. Diclofenac sodium administered to male and female rats at doses up to 4 mg/kg/day (1.4-fold of the MRHD of PENNSAID Topical Solution based on apparent bioavailability and body surface area comparison) did not affect fertility. Studies have not been conducted to determine the safety of DMSO on fertility.

13.2 Animal Toxicology and/or Pharmacology

Ocular Effects

No adverse effects were observed using indirect ophthalmoscopy after multiple-daily dermal application to rats for 26 weeks and minipigs for 52 weeks of DMSO at twice the concentration found in PENNSAID Topical Solution. Published studies of dermal or oral administration of DMSO to rabbits, dogs and pigs described refractive changes of lens curvature and cortical fibers indicative of myopic changes and/or incidences of lens opacity or discoloration when evaluated using slit-lamp biomicroscopy examination, although no ocular abnormalities were observed in rhesus monkeys during daily oral or dermal treatment with DMSO for 9 to 18 months.

14. CLINICAL STUDIES

14.1 Pivotal Studies in Osteoarthritis of the Knee

The use of PENNSAID Topical Solution for the treatment of the signs and symptoms of osteoarthritis of the knee was evaluated in two double-blind controlled trials conducted in the US and Canada, involving patients treated with PENNSAID Topical Solution at a dose of 40 drops four times a day for 12 weeks. PENNSAID Topical Solution was compared to topical placebo (2.3% DMSO with other excipients) and/or topical vehicle solution (45.5% w/w DMSO with other excipients), applied directly to the study knee. In both trials, PENNSAID Topical Solution treatment resulted in statistically significant clinical improvement compared to placebo and/or vehicle, in all three primary efficacy variables—pain, physical function (Western Ontario and McMaster Universities LK3.1 OA Index (WOMAC) pain and physical function dimensions) and Patient Overall Health Assessment (POHA)/Patient Global Assessment (PGA). Numerical results are summarized in Tables 3 and 4.

Table 3: Change in treatment outcomes after 12 weeks of treatment in one study of efficacy of PENNSAID® Topical Solution

| Efficacy Variable | Study I Mean baseline score and mean change in efficacy variables after 12 weeks of treatment | | | |
|---|---|---|---|---|
| | Mean Baseline score | PENNSAID® N=154 | Topical placebo[1] N=155 | Topical vehicle[2] N=161 |
| WOMAC pain score (Likert 3.1, 0–20) | 13 | -6.0 | -4.7 | -4.7 |
| WOMAC physical function (Likert 3.1, 0–68) | 42 | -15.7 | -12.3 | -12.1 |
| POHA (0–4) | 2.3 | -1.0 | -0.4 | -0.6 |
| [1]placebo formulation included 2.3% DMSO [2]vehicle formulation included 45.5% DMSO | | | | |

Table 4: Change in treatment outcomes after 12 weeks of treatment in one study of efficacy of PENNSAID Topical Solution

| Efficacy Variable | Study II Mean baseline score and mean change in efficacy variables after 12 weeks of treatment | | |
|---|---|---|---|
| | Mean Baseline score | PENNSAID N=164 | Topical vehicle[1] N=162 |
| WOMAC pain score (Likert 3.1, 0–20) | 13 | -5.9 | -4.4 |
| WOMAC physical function (Likert 3.1, 0–68) | 42 | -15.3 | -10.3 |
| PGA (0–4) | 3.1 | -1.3 | -1.0 |

[1] vehicle formulation included 45.5% DMSO

16. HOW SUPPLIED/STORAGE AND HANDLING

PENNSAID Topical Solution is supplied as a clear, colorless to faintly pink-orange solution containing 16.05 mg of diclofenac sodium per mL of solution, in a white high density polyethylene bottle with a white low-density dropper cap.

16.1 NDC Number & Size 15 mL bottle (physician sample)  NDC# 23635-310-11

60 mL bottle  NDC # 23635-310-60

150 mL bottle  NDC # 23635-310-15

16.2 Storage

Store at 25°C (77°F); excursions permitted to 15-30°C (59-86°F) [See USP Controlled Room Temperature].

17. PATIENT COUNSELING INFORMATION

See Medication Guide.

17.1 Medication Guide

Inform patients of the following information before initiating therapy with an NSAID and periodically during the course of ongoing therapy. Encourage patients to read the NSAID Medication Guide that accompanies each prescription dispensed prior to using PENNSAID Topical Solution.

17.2 Cardiovascular effects

PENNSAID Topical Solution, like other NSAIDs, may cause serious CV side effects, such as MI or stroke, which may result in hospitalization and even death. Although serious CV events can occur without warning symptoms, instruct patients to be alert for the signs and symptoms of chest pain, shortness of breath, weakness, slurring of speech, and to ask for medical advice when observing any indicative sign or symptoms. Inform patients of the importance of this follow-up *[see Warnings and Precautions (5.1)]*.

17.3 Gastrointestinal effects

PENNSAID Topical Solution, like other NSAIDs, may cause GI discomfort and, rarely, serious GI side effects, such as ulcers and bleeding, which may result in hospitalization and even death. Although serious GI tract ulcerations and bleeding can occur without warning symptoms, inform patients to be alert for the signs and symptoms of ulceration and bleeding, and to ask for medical advice when observing any indicative sign or symptoms including epigastric pain, dyspepsia, melena, and hematemesis. Instruct patients of the importance of this follow-up *[see Warnings and Precautions (5.2)]*.

17.4 Hepatoxicity

Inform patients of the warning signs and symptoms of hepatotoxicity (e.g., nausea, fatigue, lethargy, pruritus, jaundice, right upper quadrant tenderness, and "flu-like" symptoms). If these occur, instruct patients to stop therapy with PENNSAID Topical Solution and seek immediate medical therapy *[see Warnings and Precautions (5.3)]*.

17.5 Adverse Skin Reactions

PENNSAID Topical Solution, like other NSAIDs, can cause serious systemic skin side effects such as exfoliative dermatitis, SJS, and TEN, which may result in hospitalizations and even death. Although serious systemic skin reactions may occur without warning, instruct patients to be alert for the signs and symptoms of skin rash and blisters, fever, or other signs of hypersensitivity such as itching, and to ask for medical advice when observing any indicative signs or symptoms. *[see Warnings and Precautions (5.8)]*.

Advise patients to stop PENNSAID Topical Solution immediately if they develop any type of generalized rash and contact their physicians as soon as possible.

PENNSAID Topical Solution can cause a localized skin reaction at the application site. Advise patients to contact their physicians as soon as possible if they develop any type of localized application site rash.

Instruct patients not to apply PENNSAID Topical Solution to open skin wounds, infections, inflammations, or exfoliative dermatitis, as it may affect absorption and reduce tolerability of the drug.

Instruct patients to wait until the area treated with Pennsaid topical solution is completely dry before applying sunscreen, insect repellant, lotion, moisturizer, cosmetics, or other topical medication.

Instruct patients to minimize or avoid exposure of treated knee(s) to natural or artificial sunlight.

17.6 Weight gain and edema

Instruct patients to promptly report to their physician signs or symptoms of unexplained weight gain or edema following treatment with PENNSAID Topical Solution *[see Warnings and Precautions (5.5)]*.

17.7 Anaphylactoid reactions

Inform patients of the signs of an anaphylactoid reaction (e.g., difficulty breathing, swelling of the face or throat). If these occur, instruct patients to seek immediate emergency help *[see Warnings and Precautions (5.7)]*.

17.8 Effects during pregnancy

Instruct patients who are pregnant or intending to become pregnant not to use Pennsaid Topical Solution. [see Use in Specific Populations (8.1) and Impairment of Fertility (13.1)]

17.9 Eye Exposure

Instruct patients to avoid contact of PENNSAID Topical Solution with the eyes and mucosa. Advise patients that if eye contact occurs, immediately wash out the eye with water or saline and consult a physician if irritation persists for more than an hour.

Revised –02/2009r

Manufactured for:

Mallinckrodt Brand Pharmaceuticals, Inc.

Hazelwood, MO 63042 USA

Manufactured By:

Nuvo Manufacturing (a division of Nuvo Research Inc.)

Varennes, Quebec, Canada J3X 1P7

Medication Guide
For
Non-steroidal Anti-Inflammatory Drugs (NSAIDS)

(See the end of this Medication Guide for a list of prescription NSAID medicines.)

What is the most important information I should know about medicines called Non-Steroidal Anti-Inflammatory Drugs (NSAIDs)?

NSAID medicines may increase the chance of a heart attack or stroke that can lead to death. This chance increases:

- with longer use of NSAID medicines
- in people who have heart disease

NSAID medicines should never be used right before or after a heart surgery called a "coronary artery bypass graft (CABG)."

NSAID medicines can cause ulcers and bleeding in the stomach and intestines at any time during treatment. Ulcers and bleeding:

- can happen without warning symptoms
- may cause death

The chance of a person getting an ulcer or bleeding increases with:

- taking medicines called "corticosteroids" and "anticoagulants"
- longer use
- smoking
- drinking alcohol
- older age
- having poor health

NSAID medicines should only be used:

- exactly as prescribed
- at the lowest dose possible for your treatment
- for the shortest time needed

What are Non-Steroidal Anti-Inflammatory Drugs (NSAIDs)?

NSAID medicines are used to treat pain and redness, swelling, and heat (inflammation) from medical conditions such as:

- different types of arthritis
- menstrual cramps and other types of short-term pain

Who should not take a Non-Steroidal Anti-Inflammatory Drug (NSAID)?

Do not take an NSAID medicine:

- if you had an asthma attack, hives, or other allergic reaction with aspirin or any other NSAID medicine
- for pain right before or after heart bypass surgery

Tell your healthcare provider:

- about all of your medical conditions.
- about all of the medicines you take. NSAIDs and some other medicines can interact with each other and cause serious side effects. Keep a list of your medicines to show to your healthcare provider and pharmacist.
- if you are pregnant. NSAID medicines should not be used by pregnant women late in their pregnancy.
- if you are breastfeeding. Talk to your doctor.

What are the possible side effects of Non-Steroidal Anti-Inflammatory Drugs (NSAIDs)?

| Serious side effects include: | Other side effects include: |
| --- | --- |
| • heart attack | • stomach pain |
| • stroke | • constipation |
| • high blood pressure | • diarrhea |
| • heart failure from body swelling (fluid retention) | • gas |
| • kidney problems including kidney failure | • heartburn |
| • bleeding and ulcers in the stomach and intestine | • nausea |
| • low red blood cells (anemia) | • vomiting |
| • life-threatening skin reactions | • dizziness |
| • life-threatening allergic reactions | |
| • liver problems including liver failure | |
| • asthma attacks in people who have asthma | |

Get emergency help right away if you have any of the following symptoms:

- shortness of breath or trouble breathing
- chest pain
- weakness in one part or side of your body
- slurred speech
- swelling of the face or throat

Stop your NSAID medicine and call your healthcare provider right away if you have any of the following symptoms:

- nausea
- more tired or weaker than usual
- itching
- your skin or eyes look yellow
- stomach pain
- flu-like symptoms
- vomit blood
- there is blood in your bowel movement or it is black and sticky like tar
- unusual weight gain
- skin rash or blisters with fever
- swelling of the arms and legs, hands and feet These are not all the side effects with NSAID medicines. Talk to your healthcare provider or pharmacist for more information about NSAID medicines.

Other information about Non-Steroidal Anti-Inflammatory Drugs (NSAIDs):

- Aspirin is an NSAID medicine but it does not increase the chance of a heart attack. Aspirin can cause bleeding in the brain, stomach, and intestines. Aspirin can also cause ulcers in the stomach and intestines.
- Some of these NSAID medicines are sold in lower doses without a prescription (over-the-counter). Talk to your healthcare provider before using over-the-counter NSAIDs for more than 10 days.

<u>NSAID medicines that need a prescription</u>

| Generic Name | Tradename |
|---|---|
| Celecoxib | Celebrex |
| Diclofenac | Flector, Cataflam, Voltaren, Arthrotec™ (combined with misoprostol), PENNSAID Topical Solution |
| Diflunisal | Dolobid |
| Etodolac | Lodine, LodineXL |
| Fenoprofen | Nalfon, Nalfon200 |
| Flurbirofen | Ansaid |
| Ibuprofen | Motrin, Tab-Profen, Vicoprofen* (combined with hydrocodone), Combunox™ (combined with oxycodone) |
| Indomethacin | Indocin, IndocinSR, Indo-Lemmon™, Indomethagan™ |
| Ketoprofen | Oruvail |
| Ketorolac | Toradol |
| Mefenamic Acid | Ponstel |
| Meloxicam | Mobic |
| Nabumetone | Relafen |
| Naproxen | Naprosyn, Anaprox, AnaproxDS, EC-Naproxyn, Naprelan, Naprapac (copackaged with lansoprazole) |
| Oxaprozin | Daypro |
| Piroxicam | Feldene |
| Sulindac | Clinoril |
| Tolmetin | Tolectin, Tolectin DS, Tolectin600 |

*Vicoprofen contains the same dose of ibuprofen as over-the-counter (OTC) NSAID, and is usually used for less than 10 days to treat pain. The OTC NSAID label warns that long term continuous use may increase the risk of heart attack or stroke.

*This Medication Guide has been approved by the U.S. Food and Drug Administration.*

Revised: Month Year

Patient Instructions for Use
PENNSAID [pen/sed]
(diclofenac sodium)
Topical Solution Your doctor has prescribed PENNSAID® Topical Solution to treat your pain from osteoarthritis in your knee(s) and help you manage your daily activities better.

Before you use PENNSAID® Topical Solution:

- Apply PENNSAID® Topical Solution exactly as your doctor tells you. Do not apply PENNSAID® Topical Solution anywhere on your body other than where your doctor tells you.

- Apply PENNSAID® Topical Solution on clean, dry skin that does not have any cuts, infections or rashes.

- Use PENNSAID® Topical Solution 4 times each day on your knee(s).

- Do not get PENNSAID® Topical Solution in your eyes, nose or mouth. Only use PENNSAID® Topical Solution on your skin (topical use). If you get PENNSAID® Topical Solution in your eyes, rinse your eyes right away with water or saline. Call your doctor if your eyes are irritated for more than one hour.

Steps for using PENNSAID® Topical Solution:

Step 1. Wash your hands with soap and water before and after applying PENNSAID® Topical Solution.

Step 2. Your total dose for each knee is 40 drops of PENNSAID® Topical Solution. You will use 10 drops at a time. Put 10 drops of PENNSAID® Topical Solution either on your hand or directly on your knee.

Figure 10A:
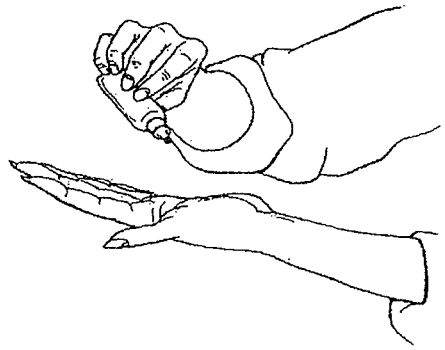
FIG. 10A shows diagram of FIG. 1. Dispense 10 drops of PENNSAID® at a time.

See Figure 10A.

Figure 1. Dispense 10 drops of PENNSAID® at a time

Step 3. Spread PENNSAID® Topical Solution evenly on the front, back and sides of your knee. Repeat this step 4 times so that your knee is completely covered with a total of 40 drops of PENNSAID® Topical Solution.

Figure 10B:
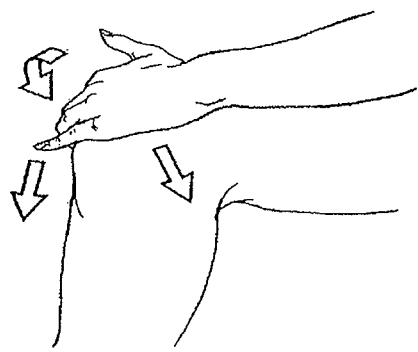
FIG. 10B shows diagram of FIG. 2. Spread PENNSAID® evenly on the front, and sides of your knee.
Figure 10C:
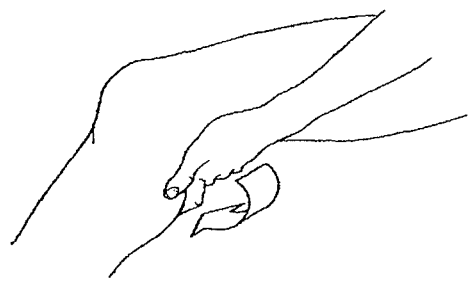
FIG. 10C shows diagram of FIG. 3. Spread PENNSAID® evenly on the back of your knee.

See Figures 10B & 10C.

Figure 2. Spread PENNSAID® evenly on the front, and sides of your knee

Figure 3:
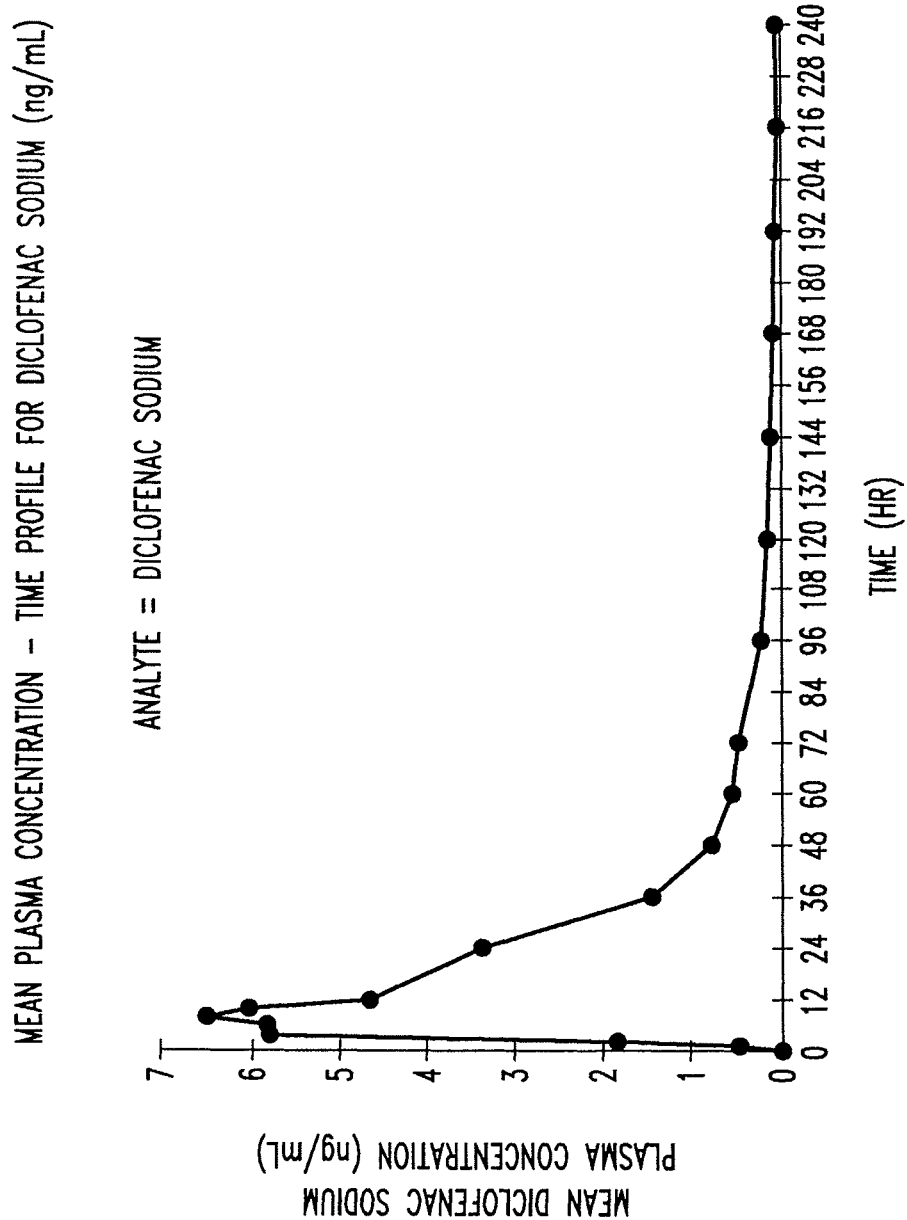
FIG. 3 shows mean plasma concentration-time profile for diclofenac sodium (ng/mL).
Figure 4:
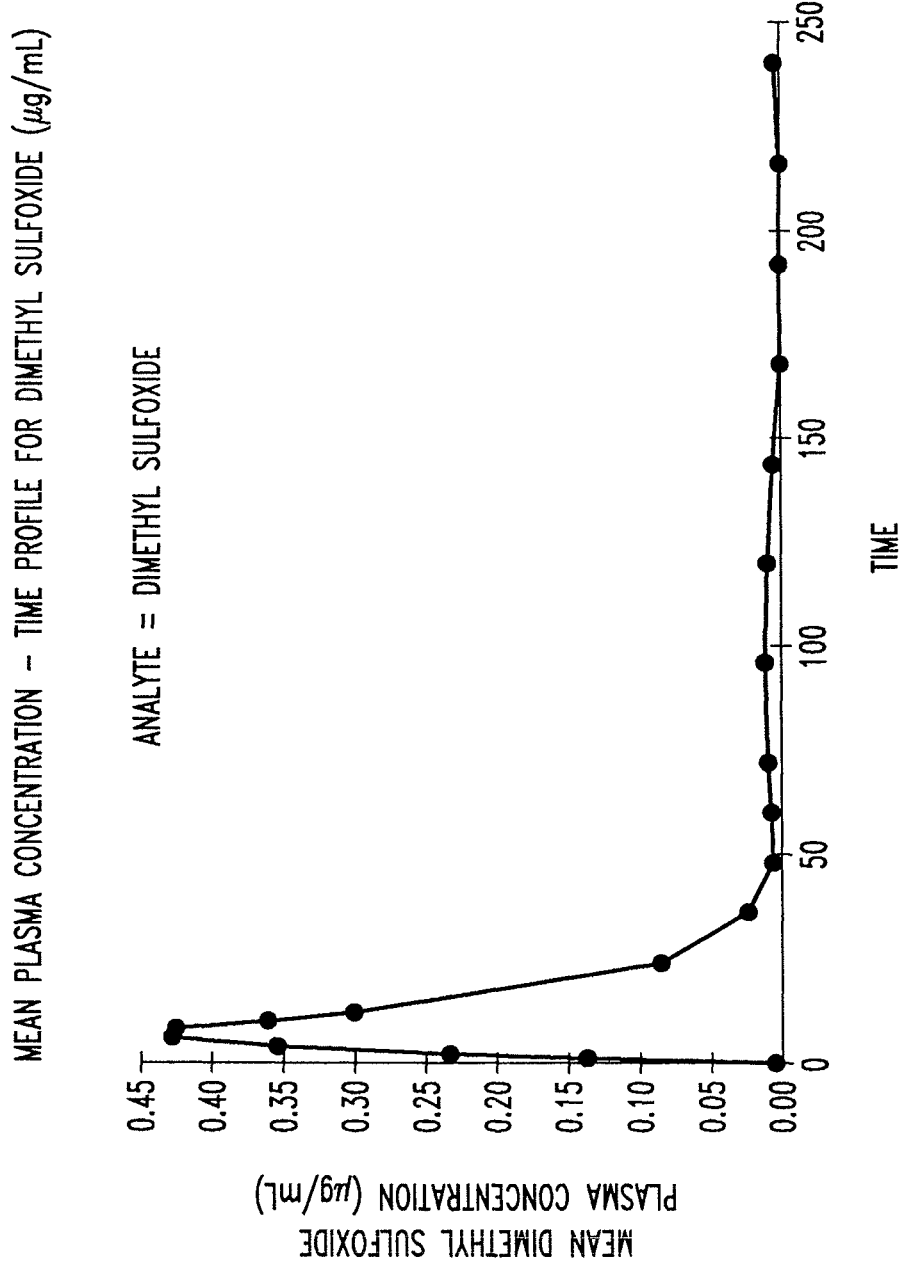
FIG. 4 shows mean plasma concentration-time profile for dimethyl sulfoxide (μg/mL).

Figure 3. Spread PENNSAID® evenly on the back of your knee

Step 4. Repeat steps 2 and 3 for the other knee if needed.

After you use PENNSAID® Topical Solution:

Do not

- cover your knee with clothing until your knee is completely dry
- put sunscreen, insect repellant, lotion, moisturizer, cosmetics, or other topical medicines on your knee until it is completely dry
- take a shower or a bath for at least 30 minutes after you put PENNSAID® Topical Solution on your knee(s).
- use heating pads or apply bandages to the skin where you have applied PENNSAID® Topical Solution.
- expose your skin to sunlight or artificial light (tanning booths) where you have put PENNSAID® Topical Solution.

How should I store PENNSAID® Topical Solution?:

- Store PENNSAID® Topical Solution between 59°F to 86°F (15°C to 30°C).

Keep PENNSAID® Topical Solution and all medicines out of the reach of children.

\* \* \*

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

We claim:

1. A method for applying topical agents to a knee of a patient with pain, the method comprising:
   (a) a patient obtaining a topical diclofenac preparation;
   (b) the patient being informed to:
      i) apply a first medication consisting of the topical diclofenac preparation to an area of the knee of said patient to treat osteoarthritis of the knee of said patient, wherein the topical diclofenac preparation comprises a therapeutically effective amount of diclofenac, or a pharmaceutically acceptable salt thereof, and 40-50% w/w dimethyl sulfoxide;
      ii) wait for the treated area to dry;
      iii) subsequently apply a sunscreen, an insect repellant or a second medication consisting of a topical medication, which is other than said first medication, to said treated area after said treated area is dry, wherein said subsequent application occurs during a course of treatment of said patient with said topical diclofenac preparation, and then
   (c) the patient carrying-out steps i-iii as informed.

2. The method according to claim 1, wherein said diclofenac preparation comprises about 45.5% w/w dimethyl sulfoxide.

3. The method according to claim 1, wherein said therapeutically effective amount of diclofenac, or a pharmaceutically acceptable salt thereof, is 2% w/w diclofenac sodium.

4. The method according to claim 1, wherein said diclofenac preparation further comprises ethanol, propylene glycol, and water.

5. The method according to claim 1, wherein said diclofenac, or a pharmaceutically acceptable salt thereof, comprises a pharmaceutically acceptable salt of diclofenac selected from a sodium salt, a potassium salt, a diethylamine salt, or an epolamine salt.

6. The method according to claim 5, wherein said diclofenac, or a pharmaceutically acceptable salt thereof, comprises diclofenac sodium.

7. The method according to claim 1, wherein said second medication is an NSAID.

8. The method according to claim 1, wherein the second medication other than said first medication is a corticosteroid.

9. The method according to claim 1, wherein the signs and symptoms of osteoarthritis are treated.

10. A method for applying topical agents to a knee of a patient with pain, said method comprising:
(a) providing a topical diclofenac preparation;
(b) providing information to:
i) apply a first medication consisting of the topical diclofenac preparation to an area of the knee of said patient to treat osteoarthritis of the knee of said patient, wherein the topical diclofenac preparation comprises a therapeutically effective amount of diclofenac, or a pharmaceutically acceptable salt thereof, and 40-50% w/w dimethyl sulfoxide;
ii) wait for the treated area to dry;
iii) subsequently apply a sunscreen, an insect repellant or a second medication consisting of a topical medication, which is other than said first medication, to said treated area after said treated area is dry, wherein said subsequent application occurs during a course of treatment of said patient with said topical diclofenac preparation; and then
(c) the patient conducting steps i-iii in accordance with published material.

11. The method according to claim 10, wherein said therapeutically effective amount of diclofenac is 2% w/w diclofenac sodium.

12. A method for applying topical agents to a knee of a patient with pain, said method comprising:
(a) providing a topical diclofenac preparation to the patient
(b) informing the patient to:
i) apply a first medication consisting of the topical diclofenac preparation to an area of the knee of said patient to treat osteoarthritis of the knee of said patient, wherein the topical diclofenac preparation comprises a therapeutically effective amount of diclofenac, or a pharmaceutically acceptable salt thereof, and 40-50% w/w dimethyl sulfoxide;
ii) wait for the treated area to dry;
iii) subsequently apply a sunscreen, an insect repellant or a second medication consisting of a topical medication, which is other than said first medication, to said treated area after said treated area is dry, wherein said subsequent application occurs during a course of treatment of said patient with said topical diclofenac preparation and then
(c) administering the first medication to the knee conducting steps i-iii in accordance with a medium providing information.

13. The method according to claim 12, wherein said therapeutically effective amount of diclofenac is 2% w/w diclofenac sodium.

14. A method for applying topical agents to a knee of a patient with pain, the method comprising:
applying a first medication consisting of the topical diclofenac preparation to an area of the knee of said patient to treat the signs and symptoms of osteoarthritis of the knee of said patient, wherein the topical diclofenac preparation comprises a therapeutically effective amount of diclofenac, or a pharmaceutically acceptable salt thereof, and 40-50% w/w dimethyl sulfoxide;
waiting for the treated area to dry; and
subsequently applying a second medication consisting of a topical medication, which is other than said first medication and is selected from the group consisting of an NSAID, tretinoin, minoxidil, and a corticosteroid, to said treated area after said treated area is dry, wherein said subsequent application occurs during a course of treatment of said patient with said topical diclofenac preparation,
wherein applying, waiting and subsequently applying are performed in accordance with written instructions.

15. The method according to claim 14, wherein said diclofenac preparation comprises about 45.5% w/w dimethyl sulfoxide.

16. The method according to claim 14, wherein said therapeutically effective amount of diclofenac is 2% w/w diclofenac sodium.

17. The method according to claim 14, wherein said diclofenac preparation further comprises ethanol, propylene glycol, and water.

18. The method according to claim 10, wherein the second medication other than said first medication is a corticosteroid.

19. The method according to claim 10, wherein the second medication other than said first medication is an NSAID.

20. The method according to claim 12, wherein the second medication other than said first medication is a corticosteroid.

21. The method according to claim 12, wherein the second medication other than said first medication is an NSAID.

22. The method according to claim 14, wherein the second medication other than said first medication is a corticosteroid.

23. The method according to claim 14, wherein the second medication other than said first medication is an NSAID.

24. The method of claim 1, wherein the informing step is by written instruction.

25. The method of claim 24, wherein the written instruction is a product insert.

26. The method of claim 10, wherein the published material is a product insert.

27. The method of claim 12, wherein the medium to provide information is a member selected from the group consisting of a flyer, an advertisement, a product insert, printed labeling, an internet web site, an internet web page, an internet pop-up window, a radio or television broadcast, a compact disk, a DVD, a podcast, an audio recording, or other recording or electronic medium.

28. The method of claim 27, wherein the medium is a product insert.

* * * * *